US007632972B2

(12) United States Patent
Hergenrother et al.

(10) Patent No.: US 7,632,972 B2
(45) Date of Patent: Dec. 15, 2009

(54) COMPOUNDS AND METHODS FOR TREATMENT OF CANCER AND MODULATION OF PROGRAMMED CELL DEATH FOR MELANOMA AND OTHER CANCER CELLS

(75) Inventors: Paul J. Hergenrother, Champaign, IL (US); Vitaliy Nesterenko, Rantoul, IL (US); Karson Putt, Urbana, IL (US); Brittany Joy Allen, Champaign, IL (US); Robin Shane Dothager, Gifford, IL (US); Benjamin James Leslie, Urbana, IL (US)

(73) Assignee: The Board of Trustees of the University of Illionis, Urbana, IL (US)

( * ) Notice: Subject to any disclaimer, the term of this patent is extended or adjusted under 35 U.S.C. 154(b) by 200 days.

(21) Appl. No.: 10/976,186

(22) Filed: Oct. 27, 2004

(65) Prior Publication Data
US 2005/0197511 A1    Sep. 8, 2005

Related U.S. Application Data

(60) Provisional application No. 60/603,246, filed on Aug. 20, 2004, provisional application No. 60/516,556, filed on Oct. 30, 2003.

(51) Int. Cl.
*C07C 233/05* (2006.01)
*A61K 31/165* (2006.01)
(52) U.S. Cl. .................. 564/190; 564/189; 514/624
(58) Field of Classification Search .............. 564/189, 564/190; 514/624
See application file for complete search history.

(56) References Cited

U.S. PATENT DOCUMENTS

| | | | | |
|---|---|---|---|---|
| 3,360,432 A | * | 12/1967 | Spano et al. | 514/624 |
| 4,301,021 A | * | 11/1981 | Breant | 424/65 |
| 5,118,845 A | * | 6/1992 | Peck et al. | 564/215 |
| 5,569,673 A | | 10/1996 | Morre et al. | |
| 5,708,020 A | * | 1/1998 | Langlois et al. | 514/469 |
| 5,852,194 A | * | 12/1998 | Lantzsch | 546/250 |
| 6,121,488 A | * | 9/2000 | Nikam | 506/27 |
| 6,444,638 B2 | | 9/2002 | Schwartz et al. | |
| 6,548,536 B2 | | 4/2003 | Hara et al. | |
| 6,605,589 B1 | | 8/2003 | Uckun et al. | |
| 6,608,026 B1 | | 8/2003 | Wang et al. | |
| 6,627,623 B2 | | 9/2003 | Ho et al. | |
| 2003/0148966 A1 | | 8/2003 | Jayaram et al. | |
| 2003/0176506 A1 | | 9/2003 | Dawson et al. | |
| 2003/0198949 A1 | | 10/2003 | Goldmakher et al. | |

FOREIGN PATENT DOCUMENTS

FR          1520070      *   4/1968

OTHER PUBLICATIONS

McQuade et al, J. Am. Chem. Soc., 1997, 119, 8528-8532.*

Kuehne et al, Journal of Organic Chemistry, 1977, 42(12) 2082-2087.*
Shiina et al, Tetrahedron Letters, 44 (2003) 1951-1955.*
Kunishima, M. et al., "Formation of carboxamides by direct condensation of carboxylic acids and amines in alcohols using a new alcohol- and water- soluble condensing agent: DMT-MM," Tetrahedron 47:1551-1558, 2001.
Kunishima, M. et al., "Approach to green chemistry of DMT-MM: recovery and recycle of coproduct to chloromethane-free DMT-MM," Tetrahedron Letters 43:3323-3326, 2002.
PCT International Search Report for International Application No. PCT/US04/35746, dated Jun. 27, 2005, 4 pages.
Adjei, A. A. et al., "Novel Anticancer Agents in Clinical Development," Cancer Biol. Ther. S1:S5-S15, 2003 (abstract).
Alley, M. C. et al., "Feasibility of Drug Screening with Panels of Human Tumor Cell Lines Using a Microculture Tetrazolium Assay," Cancer Research 48:589-601, Feb. 1, 1988.
Anderson, C. M. et al., "Systemic Treatment for Advanced Cutaneous Melanoma" Oncology, 9:1149-1154, 1995 (abstract).
Blake, C. A. et al., "Estrogen Can Protect Splenocytes from the Toxic Effects of the Environmental Pollutant 4-*tert*-Octylphenol," Endocrine 6(3):243-249, Jun. 1997.
Blatt, N. B. et al., "Signaling Pathways and Effector Mechanisms Pre-Programmed Cell Death," Bioorg. Med. Chem. 9:1371-1384, 2001.
Boyd, M. R. et al., "Some Practical Considerations and Applications of the National Cancer Institute In Vitro Anticancer Drug Discovery Screen," Drug Dev. Res. 34:91-109, 1995.
Bundgaard, H., "(C) Means to Enhance Penetration: (1) Prodrugs as a Means to Improve the Delivery of Peptide Drugs," Adv. Drug Deliv. Rev. 8:1-38, 1992.
Bundgaard, H., "Design of Prodrugs," In: *Methods in Ezymology*, K. Widder et al., Eds., Academic Press, Elsevier, pp. 309-396, 1985.
Bundgaard, H., "Design and Application of Prodrugs," Chapter 5, In: *A Textbook of Drug Design and Development*, Krosgaard et al., Eds., pp. 113-191, 1991.
Cannon-Albright, L. A. et al., "Assignment of a Locus for Familial Melanoma, MLM, to Chromosome 9p13-p22," Science 258:1148-1152, Nov. 13, 1992.
Cossarizza, A. et al., "Analysis of Mitochondria During Cell Death," Methods Cell Biol. 63:467-486, 2001.
de Graaff, M. et al., "In Vitro Antagonistic Cytotoxic Interactions Between Platinum Drugs and Taxanes on Bone Marrow Progenitor Cell CFU-GM," Anti-Cancer Drugs 10:213-218, 1999.

(Continued)

*Primary Examiner*—Shailendra Kumar
(74) *Attorney, Agent, or Firm*—Greenlee, Winner and Sullivan, P.C.

(57) ABSTRACT

Compounds and related methods for synthesis, and the use of compounds and combination therapies for the treatment of cancer and modulation of apoptosis in cells are disclosed. The generation of synthetic combinatorial libraries and the evaluation of library member compounds regarding induction of apoptosis selectively in cancer cells are disclosed. Compounds, methods of making the compounds, and therapeutic methods with application against breast cancer cells, melanoma cancer cells, colon cancer cells, and other cancer cells are described.

34 Claims, 31 Drawing Sheets

OTHER PUBLICATIONS

Fountain, J. W. et al., "Homozygous Deletions Within Human Chromosome Band 9p21 in Melanoma," Proc. Natl. Acad. Sci. 89(21):10557-10561, Nov. 1, 1992.

Gallagher, R. et al., "Characterization of the Continuous, Differentiating Myeloid Cell Line (HL-60) from a Patient with Acute Promyelocytic Leukemia," Blood 54(3):713-733, Sep. 1979.

Grever, M. R. et al., "The National Cancer Institute: Cancer Drug Discovery and Development Program," Sem. Oncol. 19(6):622-638, Dec. 1992.

Grossman, D. et al.,"Expression and Targeting of the Apoptosis Inhibitor, Survivin, in Human Melanoma," J. Invest. Dermatol. 113:1076-1081, 1999.

Hanahan, D. et al., "The Hallmarks of Cancer," Cell 100:57-70, Jan. 7, 2000.

Hartmann, A. et al., "Caspase-3: A Vulnerability Factor and Final Effector in Apoptotic Death of Dopaminergic Neurons in Parkinson's Disease," Proc. Natl. Acad. Sci. 97(6):2875-2880, Mar. 14, 2000.

Haskell, C.M., *Cancer Treatment*, 1$^{st}$ Edition, W.B. Saunders Company, pp. 62-87, 1980.

Haskell, C.M., *Cancer Treatment*, 3$^{rd}$ Edition, W.B. Saunders Company, pp. 62-87, 1991.

Haskell, C.M., *Cancer Treatment*, 5$^{th}$ Edition, W.B. Saunders Company, pp. 78-87, 2001.

Helmbach, H. et al., "Drug-Resistance in Human Melanoma," Int. J. Cancer 93:617-622, 2001.

Hwang, S.-Y. et al., "N-Phenethyl-2-Phenylacetamide Isolated from *Xenorhabdus nematophilus* Induces Apoptosis Through Caspase Activation and Calpain-Mediated Bax Cleavage in U937 Cells," Int. J. Oncol. 22:151-157, 2003.

Hwang, Z., "The Chemical Biology of Apoptosis: Exploring Protein-Protein Interactions and the Life and Death of Cells with Small Molecules," Chem Biol. 9:1059-1072, Oct. 2002.

Jemal, A. et al., "Cancer Statistics, 2002," CA Cancer J. Clin. 52:23-47, 2002.

Jeong, H.-J. et al., "Aromatase Inhibitors from *Isodon excisus* var. *coreanus*," Arch. Pharm. Res. 23(3):243-245, 2000.

Johnstone, R. W. et al., "Apoptosis: A Link Between Cancer Genetics and Chemotherapy," Cell 108:153-164, Jan. 25, 2002.

Khan, K. M. et al., "Three Tyrosinase Inhibitors and Antioxidant Compounds from *Salsola foetida*," Helvetica Chimica Acta 86:457-464, 2003.

Konstantinov, S. M. et al., "Alkylphosphocholines: Effects on Human Leukemic Cell Lines and Normal Bone Marrow Cells," Int. J. Cancer 77:778-786, 1998.

Lee, C. et al., "Agastinol and Agastenol, Novel Lignans from *Agastache rugosa* and Their Evaluation in an Apoptosis Inhibition Assay," J. Nat. Prod. 65:414-416, 2002.

Lee, C. et al., "Two New Constituents of *Isodon excisus* and Their Evaluation in an Apoptosis Inhibition Assay," J. Nat. Prod. 64:659-660, 2001.

Lev, D. C. et al., "Exposure of Melanoma Cells to Dacarbazine Results in Enhanced Tumor Growth and Metastasis In Vivo," J. Clin. Oncol. 22(11):2092-2100, Jun. 1, 2004.

Li, Q. et al., "Immunotoxicity of N,N-Diethylaniline in Mice: Effect on Natural Killer Activity, Cytotoxic T Lymphocyte Activity, Lymphocyte Proliferation Response and Cellular Components of the Spleen," Toxicology 150:179-189, 2000.

LoRusso, P. M. et al., "Preclinical Antitumor Activity of XK469 (NSC 656889)," Invest. New Drugs 16:287-296, 1999.

Makin, G. et al., "Recent Advances in Understanding Apoptosis: New Therapeutic Opportunities in Cancer Chemotherapy," Trends Mol. Med. 9(6):251-255, Jun. 2003.

Marx, J., "New Leads on the 'How' of Alzheimer's," Science 293:2192-2194, Sep. 21, 2001.

Mattson, M. P., "Apoptosis in Neurodegenerative Disorders," Nat. Rev. Mol. Cell Biol. 1:120-129, Nov. 2000.

McGovern, V. J. et al., "Pathology of Melanoma: An Overview," Chapter 3, In: *Cutaneous Melanoma*: Clinical Management and Treatment Results Worldwide, C. M. Balch et al., Eds., J. B. Lippincott Co., Philadelphia, pp. 29-53, 1985.

Middleton, M. R. et al., "A Randomized Phase III Study Comparing Dacarbazine, BCNU, Cisplatin and Tamoxifen with Dacarbazine and Inerferon in Advanced Melanoma," Br. J. Cancer 82(6):1158-1162, 2000.

Monks, A. et al., "The NCI Anti-Cancer Drug Screen: A Smart Screen to Identify Effectors of Novel Targets," Anti-Cancer Drug Design 12:533-541, 1997.

Mühlenbeck, U. et al., "Formation of Hydroxycinnamoylamides and α-Hydroxyacetovanillone in Cell Cultures of *Solanum khasianum*," Phytochemistry 42(6):1573-1579, 1996.

Negrel, J. et al., "Ether-Linked Ferulic Acid Amides in Natural and Wound Periderms of Potatoe Tuber," Phytochemistry 43(6):1195-1199, 1996.

Nesterenko, V. et al., "Identification from a Combinatorial Library of a Small Molecule that Selectively Induces Apoptosis in Cancer Cells," J. Am. Chem. Soc. 125(48):14672-14673, 2003.

Nesterenko, V. et al., "The Use of pH to Influence Regio- and Chemoselectivity in the Asymmetric Aminohydroxylation of Styrenes," Organic Letters 5(3):281-284, 2003.

Newmeyer, D. D. et al., "Mitochondria: Releasing Power for Life and Unleashing the Machineries of Death," Cell 112:481-490, Feb. 21, 2003.

Nguyen, J. T. et al., "Direct Activation of the Apoptosis Machinery as a Mechanism to Target Cancer Cells," Proc. Natl. Acad. Sci. 100(13):7533-7538, Jun. 24, 2003.

Nielsen, N. M. et al., "Glycolamide Esters as Biolabile Prodrugs of Carboxylic Acid Agents: Synthesis, Stability, Bioconversion, and Physicochemical Properties," J. Pharm. Sciences 77(4):285-298, Apr. 1988.

Norgrady, *Medicinal Chemistry A Biochemical Approach*, Oxford University Press, New York, pp. 388-392, 1985.

Oredipe, O. A. et al., "Limits of Stimulation of Proliferation and Differentiation of Bone Marrow Cells of Mice Treated with Swainsonine," International Immunopharmacology 3:1537-1547, 2003.

Prater, M. R. et al., "Single-Dose Topical Exposure to the Pyrethroid Insecticide, Permethrin in C57BL/6N Mice: Effects on Thymus and Spleen," Food Chem. Toxicol. 40:1863-1873, 2002.

Reed, J. C., "Apoptosis-Based Therapies," Nat. Rev. Drug Dis.1:111-121, Feb. 2002.

Satyamoorthy, K. et al., "No Longer a Molecular Black Box—New Clues to Apoptosis and Drug Resistance in Melanoma," Trends Mol. Med. 7(5):191-194, May 2001.

Schadendorf, D. et al., "Chemosensitivity Testing of Human Malignant Melanoma. A Retrospective Analysis of Clinical Response and In Vitro Drug Sensitivity," Cancer 73(1):103-108, Jan. 1, 1994.

Serrone, I. et al., "Dacarbazine-Based Chemotherapy for Metastatic Melanoma: Thirty-Year Experience Overview," J. Exp. Clin. Cancer Res. 19(1):21-34, 2000.

Soengas, M. S. et al., "Apoptosis and Melanoma Chemoresistance," Oncogene 22:3138-3151, 2003.

Soengas, M. S. et al., "Inactivation of the Apoptosis Effector Apaf-1 in Malignant Melanoma," Nature 409:207-211, Jan. 11, 2001.

Sundström, C. et al., "Establishment and Characterization of a Human Histiocytic Lymphoma Cell Line (U-937)," Int. J. Cancer 17:565-577, 1976.

Wadsworth, Jr., W. S. et al., "Ethyl Cyclohexylideneacetate," Organic Syntheses, Coll. vol. 5, p. 547, vol. 45, p. 44, 2004.

Yamaura, K. et al., "Inhibition of the Antibody Production by Acetaminophen Independent of Liver Injury in Mice," Biol. Pharm. Bull. 25(2):201-205, Feb. 2002.

\* cited by examiner

COMPOUNDS AND METHODS FOR TREATMENT OF CANCER AND MODULATION OF PROGRAMMED CELL DEATH FOR MELANOMA AND OTHER CANCER CELLS

CROSS-REFERENCES TO RELATED APPLICATIONS

This application claims the benefit of U.S. Provisional Patent Application No. 60/516,556, filed Oct. 30, 2003 and of U.S. Provisional Patent Application No. 60/603,246, filed Aug. 20, 2004. Each of these applications is incorporated herein by reference in entirety.

STATEMENT REGARDING FEDERALLY SPONSORED RESEARCH OR DEVELOPMENT

This invention was made, at least in part, with government support under Grant Number 0134779 awarded by the National Science Foundation. The government has certain rights in the invention.

BACKGROUND OF THE INVENTION

Cancer is a multifaceted disease that strikes millions every year. As there are many varieties of normally differentiated cell types, there is a large proportion of abnormalities that become clinically important in humans and animals. For example, melanoma is a particularly devastating type of cancer with a five-year survival rate projected to be less than 5%. There is only one single-agent drug approved for the treatment of melanoma; its rate of effectiveness is estimated at as low as about 10%.

In contrast, the onset of certain cancers has been traced to a missed apoptotic signal (Johnstone, R. W.; Rueffi, A. A.; Lowe, S. W. Cell 2002, 108, 153-164). In these cases, compounds that induce apoptosis (such as etoposide, doxorubicin, and camptothecin) have proven to be powerful chemotherapeutic agents. However, for a compound to be medicinally useful it is critical that this apoptotic induction be selective for cancer versus non-cancer cells. Indeed, it is rare to find compounds that have the selectivity needed to merit serious consideration as chemotherapeutic agents (Haskell, C. M. Cancer Treatment Ed.; W.B. Saunders Company, 62-87).

Apoptosis, or programmed cell death, is a highly conserved process used by multi-cellular organisms to rid themselves of unwanted or damaged cells (Blatt, N. B., Glick, G. D. Bioorg. Med. Chem. Lett. 2001, 9, 1371-1384; Newmeyer, D. D.; Ferguson-Miller, S. Cell 2003, 112, 481-490; Huang, Z. Chem. Biol. 2002, 9, 1059-1072). Hallmarks of apoptosis include cellular membrane blebbing, cleavage of certain nucleases and polymerases, and activation of cysteine proteases known as caspases. From a medicinal perspective, small molecules that either inhibit or induce apoptosis have significant therapeutic potential (Reed, J. C. Nat. Rev. Drug Dis. 2002, 1, 111-121; Makin, G.; Dive, C. Trends Mol. Med. 2003, 9, 251-255). Besides cancer, degenerative disorders such as Alzheimer's and Parkinson's diseases are thought to result from an aberrant increase in apoptosis (Hartmann, A. et al. Proc. Natl. Acad. Sci. 2000, 97, 2875-2880; Mattson, M. P. Nat. Rev. Mol. Cell Biol. 2000, 1, 120-129; Marx, J. Science 2001, 293, 2192-2194). In such cases, apoptotic inhibitors hold considerable medicinal promise.

Clearly there is a tremendous need to develop compositions and methods better able to address cancers. The identification of chemically-based libraries of compounds, individual compounds, combinations of compounds, and methods for applications in the treatment and study of cancer and the modulation of apoptosis are of significant value.

SUMMARY OF THE INVENTION

The following definitions are applicable.

The term chemotherapeutic agent herein refers to any substance capable of reducing or preventing the growth, proliferation, or spread of a cancer cell, a population of cancer cells, tumor, or other malignant tissue. The term is intended also to encompass any antitumor or anticancer agent.

The term effective amount, when used herein, is intended to encompass contexts such as a pharmaceutically effective amount or therapeutically effective amount.

When used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

The following abbreviations are applicable. LC-MS or LC/MS, Liquid Chromatography—Mass Spectrometry; TLC, thin layer chromatography; GI50, 50% inhibition of cell growth (the concentration needed to reduce the growth of treated cells to half that of untreated [i.e., control] cells); TGI, 100% (total) growth inhibition (the concentration required to completely halt the growth of treated cells); LC50, 50% cell kill, or lethal concentration (LC50; the concentration that kills 50% of treated cells).

The invention provides compounds and related methods for apoptosis modulation and the treatment of cancer cells. The invention also provides methods for synthesis of compounds and for the generation of combinatorial libraries of compounds. The invention also provides methods for combination therapies wherein compounds of the invention are used with one or more chemotherapeutic agents.

Without wishing to be bound by a particular theory, it is believed that compounds of the invention may act via the mechanism of modulation of apoptosis or programmed cell death to be effective in the treatment of cancer cells. It is envisioned that compounds and methods of the invention can be effective in the treatment of cancer without necessarily involving the mechanism of apoptosis.

In a preferred embodiment, the modulation of apoptosis is by induction of apoptosis. In another embodiment, the modulation of apoptosis is by inhibition of apoptosis.

In an embodiment, a compound of the invention is an inducer of cell death in a cancer cell. In another embodiment, a compound is an inducer of cell death in more than one cancer cell.

In a particular embodiment, a compound is an inducer of cell death in at least one of a lymphoma cell, leukemia cell, non-small cell lung cancer cell, colon cancer cell, brain or central nervous system (CNS) cancer cell, melanoma cell, ovarian cancer cell, renal cancer cell, prostate cancer cell, and breast cancer cell.

In a particular embodiment, a compound is an inducer of cell death in a lymphoma. In a particular embodiment, a compound is an inducer of cell death in a leukemia cell. In a particular embodiment, a compound is an inducer of cell death in a melanoma cell. In a particular embodiment, a compound is an inducer of cell death in a breast cancer cell. In a particular embodiment, a compound is an inducer of cell death in a cell type of a screening panel of 60 members used by the National Cancer Institute.

In an embodiment, a compound or library of the invention is useful in screening to identify a compound having activity against a cancer cell.

The invention provides compounds having formula (X1):

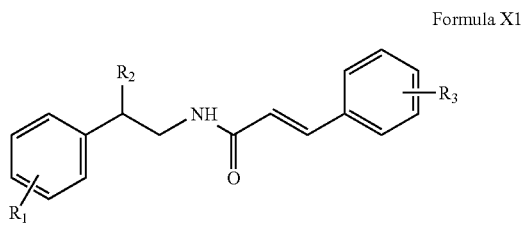

Formula X1 wherein $R_1$ is H, one or more halogens, one or more alkyl (particularly having 1, 2, or 3 carbon atoms), or one or more $OR_4$; $R_2$ is H, one or more halogens (particularly F or Cl); one or more alkyl (particularly having 1-3 carbon atoms); one or more halogenated alkyl; or one or more $OR_5$, $R_3$ is H, one or more halogens, one or more alkyl (particularly having 1 to 3 carbon atoms, or one or more $OR_6$; wherein $R_4$ is H, alkyl (particularly alkyl having 1 to 3 carbons), or halogenated alkyl (particularly —$CF_3$); wherein $R_5$ is H, alkyl (particularly alkyl having 1 to 3 carbons), or halogenated alkyl (particularly —$CF_3$); wherein $R_6$ is H, alkyl (particularly alkyl having 1 to 3 carbons), or halogenated alkyl (particularly —$CF_3$).

The invention also provides compounds based on the above formula wherein $R_1$ is hydrogen, 4-hydroxy, or 4 alkoxy; $R_2$ is hydrogen, hydroxy or alkoxy; and $R_3$ is hydrogen, 4-hydroxy; 3,4-dihydroxy; 3-hydroxy, 4-alkoxy; 3-alkoxy, 4 hydroxy; 3,4,5-trialkoxy; 4-hydroxy, 3,5-alkoxy; or 3-alkoxy.

In embodiments of the invention, $R_3$ is 3-hydroxy; 4-alkoxy; 3,4-dialkoxy; 3,4,5-trihydroxy; 3,5-dialkoxy, or 4-hydroxy.

In embodiments of the invention, the alkoxy groups of the above compounds are methoxy, ethoxy, or propoxy groups. Preferably, the alkoxy groups are methoxy groups.

In embodiments of the invention, $R_2$ is halogen, alkyl, or halogenated methyl. Preferably an alkyl group comprises methyl, ethyl, or propyl. In a particularly preferred embodiment, an alkyl group is methyl. In an embodiment, a halogenated methyl group comprises $CF_3$.

In an embodiment, $R_3$ represents one or more halogens. In an embodiment, $R_3$ represents 3,4-dichloro or 3,4-difluoro.

In an embodiment, $R_1$ is 4-halogen. In an embodiment, $R_1$ is 3,4-dihydroxy; 3,4-dialkoxy; 3,4-dihalogen; 3,4,5-trihydroxy; or 3,4,5-trialkoxy. In an embodiment, $R_1$ is more than one hydroxyl, alkoxy, or halogen. In an embodiment, $R_1$ is 3-alkoxy, 4-hydroxy.

In an embodiment, compounds of the above formula are provided in substantially pure form.

In an embodiment, compounds of the above formula (X1) are provided in substantially pure enantiomeric form. The invention also provides enantiomers of the above formula having enantiomeric purity greater than or equal to about 75% or more. The invention further provides enantiomers of the above formula having enantiomeric purity greater than or equal to about 95% or more.

In an embodiment, compounds of the above formula (X1) are optionally provided in racemic or non-racemic mixtures.

The invention also provides enantiomeric compounds of formula (Y1):

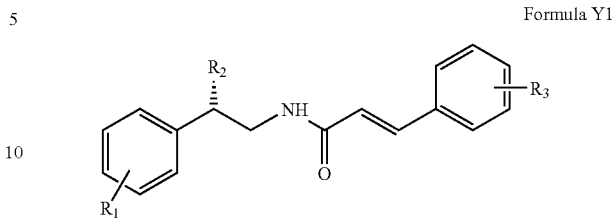

Formula Y1 wherein $R_1$, $R_2$, and $R_3$ are as defined herein.

The present invention also provides possible prodrugs and pharmaceutical compositions, including possible salts, of the compounds of formulas (X1) and/or (Y1), including variations and others as described herein.

In an embodiment, the invention provides a method of synthesizing a compound. In an embodiment, the invention provides a method of synthesizing an amide compound of formula X1 or Y1, comprising: a) providing an amine, wherein the amine is selected from the group consisting of amines 8-18 of Scheme 2; b) providing an acid, wherein the acid is selected from the group consisting of acids A-H of Scheme 2; and c) reacting the amine with the acid by coupling using a solid-phase carbodiimide reagent or solution phase carbodiimide reagent; thereby synthesizing the amide compound.

In a particular embodiment, the invention provides a compound of formula X1, and method of synthesis therefor, wherein $R_1$ is 4-hydroxy, $R_2$ is methoxy, and $R_3$ is 4-hydroxy-3-methoxy. In an embodiment, such compound is a racemic or non-racemic mixture. In an embodiment, the invention provides a method of synthesis for a compound of formula Y1 wherein $R_1$ is 4-hydroxy, $R_2$ is methoxy, and $R_3$ is 4-hydroxy-3-methoxy. In a particular embodiment, the method of synthesis is for an enantiomeric form.

In a particular embodiment, the invention provides a compound of formula Y1 and method of synthesis therefor, wherein $R_1$ is 4-hydroxy, $R_2$ is hydroxy, and $R_3$ is 4-hydroxy-3-methoxy.

In a particular embodiment, the invention provides a compound of formula X1 and method of synthesis therefor, wherein $R_1$ is 4-hydroxy, $R_2$ is (R)-hydroxy, and $R_3$ is 4-hydroxy-3-methoxy.

In certain embodiments, the invention provides compounds of formulas X1 and Y1 except the (S) enantiomer of structure 9-D, wherein said enantiomer is in substantially pure enantiomeric form. In certain embodiments, the invention provides compounds of formulas X1 and Y1 except one or more of the structures of 9D, 12A, 12B, and 13B.

The invention provides geometric isomers of formulas X1 and Y1 preferably in the trans configuration regarding the carbon-carbon double bond. In other embodiments, analogous compounds of the cis isomers are provided.

The invention provides compounds of formulas X1 and/or Y1, and others described herein, for use in medical therapy. Such therapy can include, for example, use in inducing apoptosis, modulating caspase activity, inducing cell death, or treating cancer, preferably for use in treating lung cancer, breast cancer, prostate cancer, other forms of cancer, lymphoma, and leukemia, such as, for example, acute lymphocytic leukemia (ALL), acute myelogenous leukemia (AML), chronic myelogenous leukemia (CML), and other diseases of proliferation. Such therapy can include as well the use of such compounds for the manufacture of a medicament for inducing apoptosis, modulating caspase activity, inducing cell death, or treating cancer, preferably for use in treating lung cancer, breast cancer, prostate cancer, CML, ALL, AML, other forms of cancer or leukemia, and other diseases of proliferation, in a mammal, such as a human.

The compounds of the invention are also useful for treatment in diseases in which apoptosis is one of the symptoms, such as, for example, heart conditions, Parkinson's disease, Alzheimer's disease and the like.

The invention also provides a method to induce apoptosis or death in a cell comprising contacting the cell in vivo, with an effective amount of a compound of the invention as described herein.

The invention also provides a method to induce apoptosis or death in a cell comprising contacting the cell ex vivo, with an effective amount of a compound of the invention as described herein.

The invention also provides a method to induce apoptosis or death in a cell comprising contacting the cell in vitro, with an effective amount of a compound of the invention as described herein.

In an embodiment, a cell to be targeted by a composition or method of the invention can be any type of cancer cell, for example a leukemia cell, lymphoma cell, and cells of various tissue types and at various stages of differentiation.

The invention also provides a method to treat cancer or induce apoptosis in a mammal in need of such treatment comprising administering to the mammal, an effective amount of a compound of the invention as described herein.

The invention provides a method of using a compound of structure 13-D for inducing apoptosis in vivo, ex vivo, or in vitro. In a preferred embodiment, compound 13D is in substantially pure enantiomeric form, where such purity is established by methods known in the art.

In an embodiment, the invention provides a compound of formula X1 or Y1 capable of achieving a value, known as a 50% inhibitory concentration (IC50) in a cytotoxicity assay, wherein such IC50 value is less than 300 µM. In a preferred embodiment, such IC50 value is less than 100 µM. In a more preferred embodiment, such IC50 value is less than 50 µM.

In an embodiment, a compound of the invention demonstrates enhanced activity for modulation of apoptosis. In particular embodiments, such compounds demonstrate enhanced activity for induction of apoptosis. In an embodiment, such a compound is X1 or Y1 or Z1.

The invention also provides a method to activate a caspase in a cell comprising contacting the cell, in vitro or in vivo, with an effective amount of a compound of the invention as described herein.

The invention also provides a method for preventing or treating a pathological condition or symptom in a mammal, such as a human, associated with caspase (for example, caspase 3) activation comprising administering to a mammal in need of such therapy, an effective caspase-modulating amount of a compound of the invention as described herein.

The invention also provides a therapeutic method to induce cell death comprising contacting a cell, in vivo, ex vivo, or in vitro, with an effective amount of a compound of the invention as described herein. In an embodiment, the induction of cell death is at least partially selective for cancer cells.

The invention also provides a method to induce cell death in a mammal in need of such treatment comprising administering to the mammal, an effective amount of a compound of the invention as described herein.

The invention also provides a method to treat cancer (e.g., lung cancer, breast cancer, prostate cancer, ALL, AML, solid tumors, other forms of cancer or leukemia, and other diseases of proliferation) in a mammal in need of such treatment comprising administering to the mammal, an effective amount of a compound of the invention as described herein.

The invention provides methods of treating a cancer cell comprising contacting said cell with a therapeutically effective amount of a combination of a compound of the invention and a chemotherapeutic agent. The invention provides methods of treating cancer in a subject comprising administration of an amount of a chemotherapeutic agent and an amount of a compound of the invention, wherein the combined amounts of chemotherapeutic agent and said compound are effective to treat cancer in the subject.

In an embodiment, the agent comprises dacarbazine, etoposide, doxorubicin, camptothecin, or other chemotherapeutic agent. In an embodiment, the components of a combination therapy have an additive effect. In another embodiment, the components of a combination therapy have a synergistic or potentiating effect. In an embodiment, a compound of the invention and a chemotherapeutic agent are administered sequentially, or simultaneously, wherein the administration including the order of components is optionally selected for optimal clinical results.

The invention provides methods for screening a modulating agent which when combined with an anticancer therapeutic agent increases apoptosis in cancer cells. In an embodiment, the modulating agent is a compound of the invention. The invention also provides methods for screening anticancer therapeutic agents suitable for combination therapy with a compound of the invention.

The invention provides methods of generating a chemical library. In an embodiment, the library is combinatorial.

The invention provides methods for synthesis of compounds of the invention.

In an embodiment, one of 10 acid compounds (see FIG. 1) and one of 69 amine compounds (see FIG. 1, FIG. 2A, and FIG. 2B) are reacted to generate a product compound wherein said product compound is an amide. In a preferred embodiment, the amide compound is an anti-cancer compound. In an embodiment, a library of 690 compounds is generated by reacting each of 10 acid compounds with each of 69 amine compounds. In a preferred embodiment, each compound of the library is screened for anti-cancer activity. In a preferred embodiment, a compound of the library is a chemotherapeutic agent.

In an embodiment, a chemotherapeutic agent is selected from the group consisting of the compounds in FIG. 3.

The invention provides compounds having formula Z1:

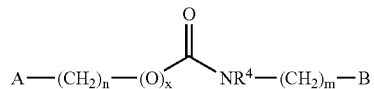

where: x is 0 or 1 to indicate the presence or absence of the oxygen (with oxygen it is a carbamate; without it is an amide);

n and m, independently, are zeroes or integers ranging from 1 to 6;

$R^4$ is a hydrogen or an alkyl group, particularly an alkyl group having from 1-3 carbon atoms;

one of the $CH_2$ groups that is not linked to —O—CO— or —$NR^4$— can be replaced with an oxygen atom one or more of the carbons of the $(CH_2)_n$ and $(CH_2)_m$ groups can be substituted with one or two non-hydrogen substituents selected from halogens, alkyl groups having 1 to 3 carbon atoms, alkoxy groups having from 1 to 3 carbon atoms;

a —CH$_2$—CH$_2$— group of either or both of the (CH$_2$)$_n$ and (CH$_2$)$_m$ groups can be replaced with a —CR$^4$=CR$^4$— group where each R$^4$ group is, independently, a hydrogen or an alkyl group, particularly an alkyl group having from 1-3 carbon atoms;

A and B, independently, are selected from the group consisting of C or D where:

C is an optionally substituted straight-chain, branched or cyclic alkyl or alkene groups having from 1 to 20 carbon atoms which are optionally substituted with one or more halogens, one or more alkoxy groups, one or more aromatic groups, wherein the alkoxy group substituents can have from 1 to 3 carbon atoms which are optionally substituted with one or more halogens;

D is an optionally substituted aromatic group having one or two carbon rings which may be fused aromatic rings, e.g., one or two 6-member rings or one 6 member ring and one 5-member ring, wherein one or more carbons of the one or two aromatic rings may be substituted with one or more halogens, one or more alkyl groups having from 1 to 3 carbon atoms which may be substituted with one or more halogens; or one or more alkoxy groups having from 1 to 3 carbons which may be substituted with one or more halogens;

wherein only one of A or B can be C.

In alternative specific embodiments A is C and B is D, B is C and A is D, or A and B are both D.

In specific embodiments C is: (C1) an optionally substituted straight-chain alkyl or alkene group; (C2) an optionally substituted cyclic alkyl or alkene group; or (C3) an optionally substituted branched alkyl group.

In specific embodiments D is: (D1) an optionally substituted phenyl group; or (D2) an optionally substituted naphthalene group.

In alternative specific embodiments A is C1 and B is one of D1 or D2; A is C2 and B is one of D1 or D2; A is C3 and B is one of D1 or D2; A is D1 and B is one of C1, C2 or C3; A is D2 and B is one of C1, C2 or C3.

In more specific embodiments C1 is:
(C11) an unsubstituted straight-chain alkyl group having from 6 to 20 carbon atoms;
(C12) an unsubstituted straight-chain alkene group having from 6 to 20 carbon atoms and containing one or two double bonds;
(C13) a straight-chain alkyl group substituted with one or more optionally substituted phenyl groups; particularly where the phenyl rings are optionally substituted with one or more halogens; one or more alkyl groups having 1 to 3 carbon atoms, one or more alkoxy groups having from 1 to 3 carbon atoms or mixtures of such substituents; or
(C14) an alkyl group substituted with one, two or three optionally substituted phenyl rings.

In more specific embodiments C2 is:
(C21) an unsubstituted cyclic alkyl group;
(C22) a substituted cyclic alkyl group; particularly where the substituents are one or more halogens;
(C23) an unsubstituted bicyclic alkyl group;
(C24) a substituted bicyclic alkyl group, particularly where the substituents are one or more halogens;
(C25) an unsubstituted tricyclic alkyl group; or
(C26) a substituted tricyclic alkyl group, particularly where the substituents are one or more halogens.

In more specific embodiments C3 is:
(C31) an unsubstituted branched alkyl group having 3, 4 or more carbon atoms;
(C32) a substituted branched alkyl group having 3, 4 or more carbon atoms; or
(C33) a branched alkyl group substituted with one or more halogens.

In more specific embodiments D1 is:
(D11) an unsubstituted phenyl group;
(D12) a phenyl group substituted with one or more alkoxy groups;
(D13) a phenyl group substituted with one, two or three alkoxy groups;
(D14) a phenyl group substituted with one or more alkyl groups;
(D15) a phenyl group substituted with one, two or three alkyl groups;
(D16) a phenyl group substituted with one or more halogens; or
(D17) a phenyl group substituted with one, two or three halogens.

In more specific embodiments D2 is:
(D21) an unsubstituted naphthalene group;
(D22) a naphthalene group substituted with one or more alkoxy groups;
(D23) a naphthalene group substituted with one or more alkyl groups; or
(D24) a naphthalene group substituted with one or more halogens.

In alternative specific embodiments:
A is C11 and B is one of D1, D12, D13, D14, D15, D16, D17, D21, D22, D23, or D24;
A is C12 and B is one of D11, D12, D13, D14, D15, D16, D17, D21, D22, D23, or D24;
A is C13 and B is one of D11, D12, D13, D14, D15, D16, D17, D21, D22, D23, or D24;
A is C14 and B is one of D1, D12, D13, D14, D15, D16, D17, D21, D22, D23, or D24;
A is C21 and B is one of D11, D12, D13, D14, D15, D16, D17, D21, D22, D23, or D24;
A is C22 and B is one of D1, D12, D13, D14, D15, D16, D17, D21, D22, D23, or D24;
A is C23 and B is one of D1, D12, D13, D14, D15, D16, D17, D21, D22, D23, or D24;
A is C24 and B is one of D1, D12, D13, D14, D15, D16, D17, D21, D22, D23, or D24;
A is C25 and B is one of D11, D12, D13, D14, D15, D16, D17, D21, D22, D23, or D24;
A is C26 and B is one of D11, D12, D13, D14, D15, D16, D17, D21, D22, D23, or D24;
A is C31 and B is one of D1, D12, D13, D14, D15, D16, D17, D21, D22, D23, or D24;
A is C32 and B is one of D11, D12, D13, D14, D15, D16, D17, D21, D22, D23, or D24;
A is C33 and B is one of D1, D12, D13, D14, D15, D16, D17, D21, D22, D23, or D24;
B is C11 and A is one of D11, D12, D13, D14, D15, D16, D17, D21, D22, D23, or D24;
B is C12 and A is one of D1, D12, D13, D14, D15, D16, D17, D21, D22, D23, or D24;
B is C13 and A is one of D1, D12, D13, D14, D15, D16, D17, D21, D22, D23, or D24;
B is C14 and A is one of D11, D12, D13, D14, D15, D16, D17, D21, D22, D23, or D24;
B is C21 and A is one of D1, D12, D13, D14, D15, D16, D17, D21, D22, D23, or D24;
B is C22 and A is one of D11, D12, D13, D14, D15, D16, D17, D21, D22, D23, or D24;
B is C23 and A is one of D11, D12, D13, D14, D15, D16, D17, D21, D22, D23, or D24;

B is C24 and A is one of D11, D12, D13, D14, D15, D16, D17, D21, D22, D23, or D24;

B is C25 and A is one of D11, D12, D13, D14, D15, D16, D17, D21, D22, D23, or D24;

B is C26 and A is one of D11, D12, D13, D14, D15, D16, D17, D21, D22, D23, or D24;

B is C31 and A is one of D11, D12, D13, D14, D15, D16, D17, D21, D22, D23, or D24;

B is C32 and A is one of D11, D12, D13, D14, D15, D16, D17, D21, D22, D23, or D24;

B is C33 and A is one of D11, D12, D13, D14, D15, D16, D17, D21, D22, D23, or D24;

Both of A and B are one of D11, D12, D13, D14, D15, D16, D17, D21, D22, D23, or D24; or Both of A and B are one of D11, D12, D13, D14, D15, D16, D17, D21, D22, D23, or D24 and A and B are different groups.

In additional embodiments:

A is C11 and B is D1;
A is C11 and B is D11;
A is C2 and B is D2;
A is C2 and B is D22 or D23;
A is C21 and B is D22 or D23;
A is C23 and B is D22 or D23;
A is C25 and B is D22 or D23;
A is C14 and B is D11;
A is C14 and B is D11;
A is C14 and B is D12;
A is C14 and B is D13;
A is C14 and B is D14;
A is C14 and B is D15;
A and B are different D1 groups;
A and B are different D12 groups; or
A and B are different D13 groups.

More specifically C is:

(C111) an unsubstituted straight-chain alkyl group having from 10 to 20 carbon atoms;

(C112) an unsubstituted straight-chain alkyl group having from 15 to 20 carbon atoms;

(C113) an optionally substituted straight-chain alkyl group having from 10 to 20 carbon atoms;

(C141) a methyl group substituted with one, two or three optionally substituted phenyl groups; or (C142) a methyl group substituted with one, two or three phenyl rings.

More specifically D is: (D111) a 3,4,5-substituted phenyl ring;

(D112) a 2-substituted phenyl ring;
(D113) a 3-substituted phenyl ring;
(D114) a 4-substituted phenyl ring;
(D115) a 3,4-substituted phenyl ring; or
(D221) a 4-substituted naphthalene ring.

In additional embodiments, A is one of C111, C112, C113, C141, or C142 and B is one of D111, D112, D113, D114, D115 or D221. In further embodiments, A is one of D11, D112, D113, D114, D115 or D221 and B is one of D111, D112, D113, D114, D115 or D221.

In more specific embodiments A is: an optionally substituted triphenyl methyl group; a triphenyl methyl group; a straight-chain alkyl group having from 16, 17, or 18 carbon atoms; a n-hetadecane group; an optionally substituted norbornane (also called bicyclo[2.2.1]heptane); an optionally substituted adamantane (also called tricyclodecane); a 3-alkoxy phenyl group; a 3-methoxy phenyl group; a 4-alkoxy naphthalene group; a 4-methoxy naphthalene group; a 3,4,5-trialkoxy phenyl group; or a 3,4,5-trimethoxy phenyl group.

In more specific embodiments B is: a phenyl group; an alkyl substituted phenyl group; a 4-alkyl phenyl group; a 4-methyl phenyl group; an alkoxy substituted phenyl group; a 3-alkoxy phenyl group; a 3-methoxy phenyl group; a 4-alkoxy naphthalene group; a 4-methoxy naphthalene group; a 3,4,5-trialkoxy phenyl group; or a 3,4,5-trimethoxyphenyl group.

In general, in compounds of this invention A can be any one of the A groups identified above and B can be any one of the B groups identified above.

In an embodiment, compounds of the above formula are provided in substantially pure form.

In an embodiment, compounds of the above formula (Z1) are provided in substantially pure enantiomeric form. The invention also provides enantiomers of the above formula having enantiomeric purity greater than or equal to about 75% or more. The invention further provides enantiomers of the above formula having enantiomeric purity greater than or equal to about 95% or more.

In an embodiment, compounds of the above formula (Z1) are optionally provided in racemic or non-racemic mixtures.

The present invention also provides possible prodrugs and pharmaceutical compositions, including possible salts, of the compounds of formula Z1, including variations and others as described herein.

In a particular embodiment, the invention provides a compound of formula Z1, and method of synthesis therefor. In an embodiment, the method of synthesizing a compound comprises a) providing an amine, wherein the amine is selected from the group consisting of amines of FIG. 12 and FIG. 13; b) providing a carboxylic acid, wherein the acid is selected from the group consisting of acids of FIG. 12 and FIG. 13; c) converting the carboxylic acid to an acid chloride; and d) reacting the amine with the acid chloride; thereby synthesizing the amide compound. In a specific embodiment, the carboxylic acids are first converted to their acid chlorides by treatment with thionyl chloride ($SOCl_2$).

The invention provides compounds of formula Z1, and others described herein, for use in medical therapy. Such therapy can include, for example, use in inducing apoptosis, modulating caspase activity, inducing cell death, or treating cancer, preferably for use in treating lung cancer, breast cancer, prostate cancer, other forms of cancer, lymphoma, and leukemia, such as, for example, acute lymphocytic leukemia (ALL), acute myelogenous leukemia (AML), chronic myelogenous leukemia (CML), and other diseases of proliferation. Such therapy can include as well the use of such compounds for the manufacture of a medicament for inducing apoptosis, modulating caspase activity, inducing cell death, or treating cancer, preferably for use in treating lung cancer, breast cancer, prostate cancer, CML, ALL, AML, other forms of cancer or leukemia, and other diseases of proliferation, in a mammal, such as a human. The compounds of the invention are also useful for treatment in diseases in which apoptosis is one of the symptoms, such as, for example, heart conditions, Parkinson's disease, Alzheimer's disease and the like.

In an embodiment, the invention provides a compound, preferably of formula Z1, capable of achieving a value, known as a 50% inhibitory concentration ($IC_{50}$) in a cytotoxicity assay, wherein such value is less than 300 µM. In a preferred embodiment, such value is less than 100 µM. In a more preferred embodiment, such value is less than 50 µM. In a highly preferred embodiment, the value is less than 10 µM.

Compounds of the invention and compounds useful in the methods of this invention include those of the above formulas and pharmaceutically-acceptable salts and esters of those compounds. Salts include any salts derived from the acids of the formulas herein which are acceptable for use in human or veterinary applications.

Pharmaceutically acceptable salts are used as known in the art and can comprise, for example, pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $Cl^-$, $Br^-$), sulfate, acetates (e.g., acetate, trifluoroacetate), ascorbates, aspartates, benzoates, citrates, and lactate.

In an embodiment, the invention provides a therapeutic composition comprising one or more compounds and for each compound a pharmaceutically acceptable salt or ester thereof; wherein the compounds are present in the composition in an amount or in a combined amount effective for obtaining the desired therapeutic benefit. The therapeutic compositions of this invention optionally further comprise a pharmaceutically acceptable carrier as known in the art.

BRIEF DESCRIPTION OF THE FIGURES

FIG. 2A shows Caspase-3 activity of U-937 cells treated with 100 μM 13-D. FIG. 2B shows flow cytometry of U-937 cells treated with 100 μM 13-D and stained with JC-9 after 72 h; non-treated and etoposide treated cells are shown as controls.

FIG. 6 illustrates data from flow cytometry analysis regarding an enrichment technique. FITC labeled anti-TCR antibodies were used to determine the purity of T cells in pre- and post-column samples.

DETAILED DESCRIPTION OF THE INVENTION

The invention may be further understood by the following non-limiting examples.

Example 1

Synthesis and Library Generation

Figure 1:
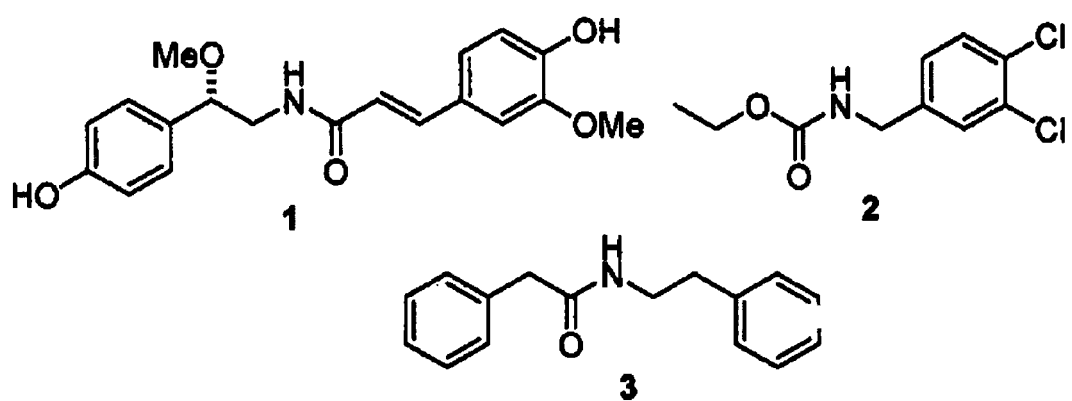
FIG. 1 illustrates the structures of natural product from Isodon excisus (1), carbamate (2), and N-phenethyl-2-phenylacetamide (NPPA) (3).

We synthesized a combinatorial library of compounds whose members can have activity in apoptotic assays and preferably can selectively induce apoptosis in cancer cells. Among the classes of molecules that have displayed activity in either pro- or anti-apoptotic assays are N-acylated aromatic amines, as exemplified by a natural product from Isodon excisus (Structure 1, FIG. 1) (Lee, C.; Kim, J.; Lee, H.; Lee, S.; Kho, Y. J. Nat. Prod. 2001, 64, 659-660); carbamate (Structure 2, FIG. 1) (Hwang, S.-Y.; Paik, S.; Park, S.-H.; Kim, H.-S.; Lee, I.-S.; Kim, S.-P.; Baek, W. K.; Suh, M.-H.; Kwon, T. K.; Park, J.-W.; Park, J.-B.; Lee, J.-J.; Suh, S. I. Int. J. Oncol. 2003, 151-157); and N-phenethyl-2-phenylacetamide (NPPA) (Structure 3, FIG. 1) (Nguyen, J. T.; Wells, J. A. Proc. Natl. Acad. Sci. 2003, 100, 7533-7538).

The synthesis of natural product 1 was performed as described in Scheme 1. Asymmetric aminohydroxylation under pH-controlled conditions9 on styrene 4 gave the secondary alcohol 5 as the dominant regioisomer. The enantiomeric ratio of the product was 85:15, which was improved to >99:1 by crystallization. After O-methylation and deprotections, the resulting primary amine was N-acylated with ferulic acid activated by DCC to provide 1. Compound 1 was modestly active (IC50=273 µM) in cytotoxicity assays with U-937 cells.

Scheme 1. Synthesis of natural product 1:

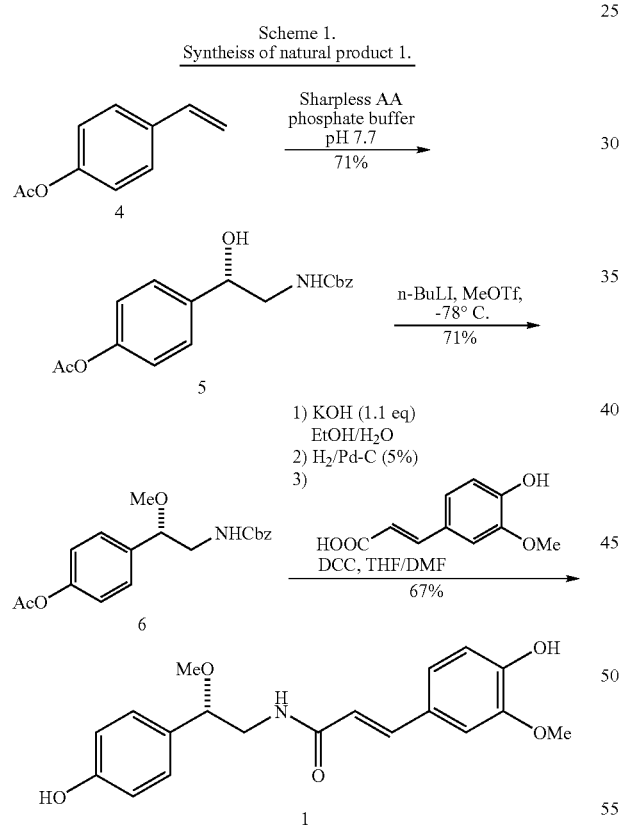

A library of derivatives of the natural product 1 was created (Scheme 2), and its members were evaluated for their ability to induce cell death. The eight acid and eleven amine building blocks depicted in Scheme 2 were coupled in parallel, using the polymeric-supported carbodiimide (structure 7), to provide 88 amide products. After simple filtration to remove the resin, between 2-5 milligrams of amide was typically obtained. A determination was made of the precise milligram amount for every product, which allowed for all molecules to be prepared as equimolar stock solutions for biological screening. Evaluation of every library member via LC-MS showed that all 88 of the amides were successfully synthesized and that the average purity of these products was 85% (see supporting information).

Scheme 2A; synthesis of a library of compounds based on compound 1.

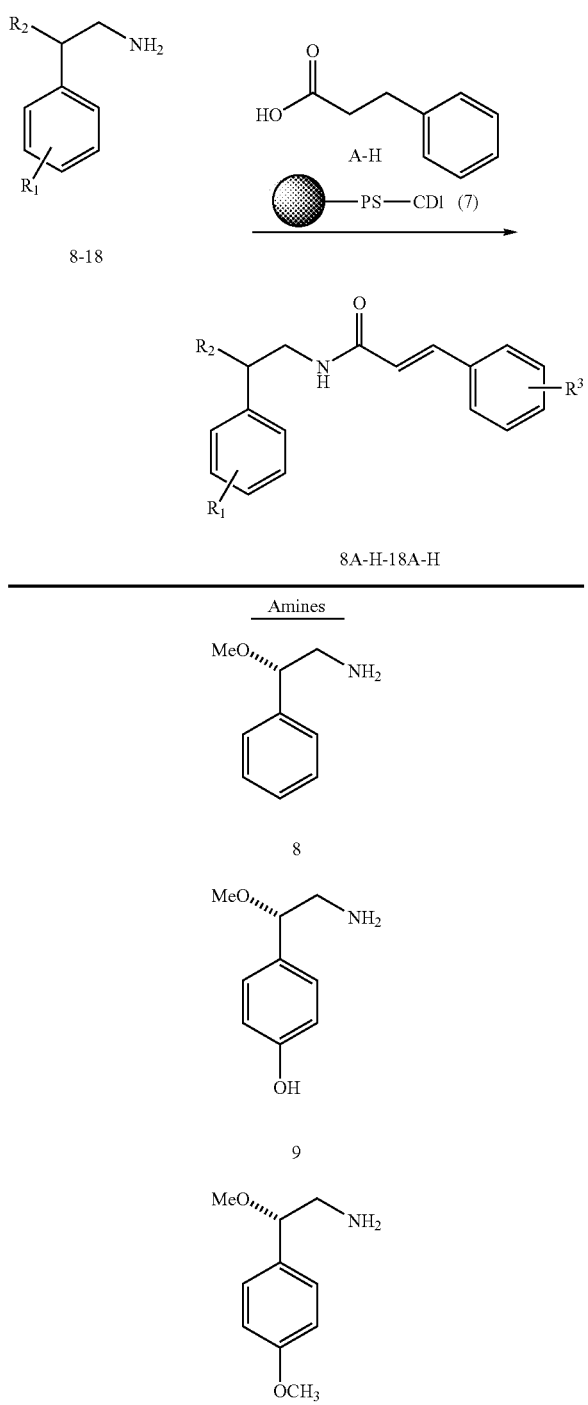

-continued
Scheme 2. Synthesis of a library of compounds based on 1.
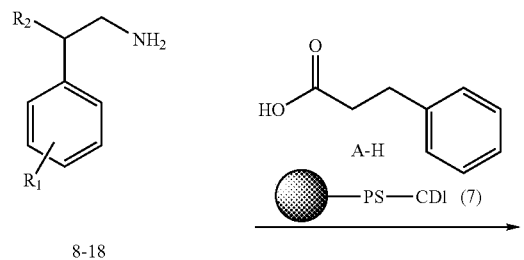
8-18
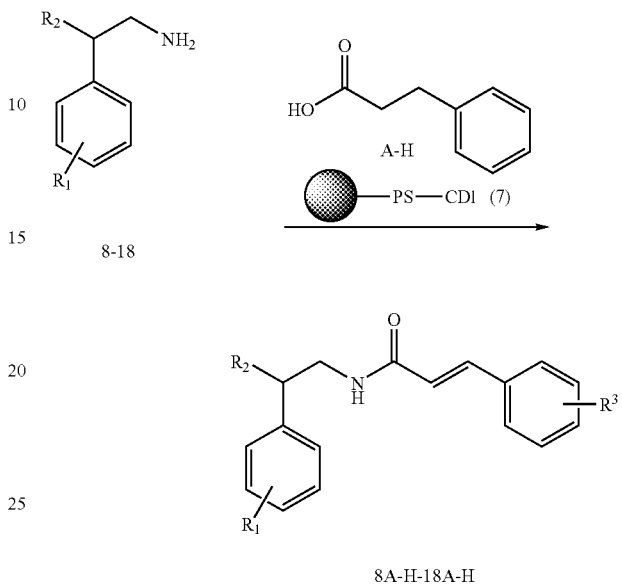
8A-H-18A-H
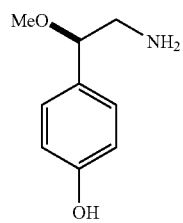
11
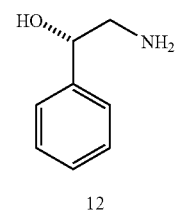
12
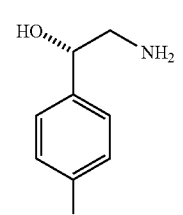
13
-continued
Scheme 2. Synthesis of a library of compounds based on 1.
8-18
8A-H-18A-H
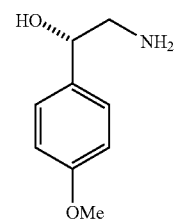
14
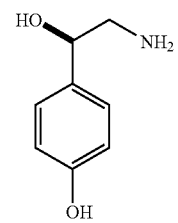
15
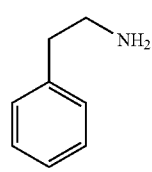
16

Scheme 2. Synthesis of a library of compounds based on 1.
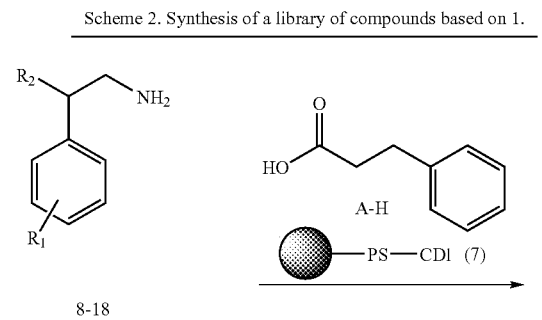
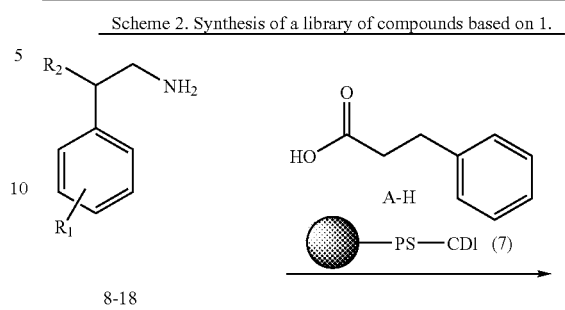
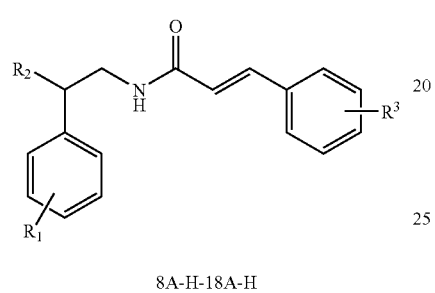
8A-H-18A-H
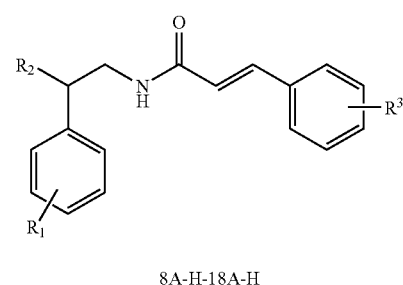
8A-H-18A-H
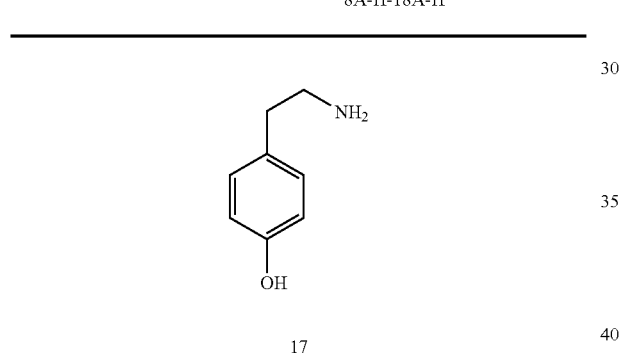
17
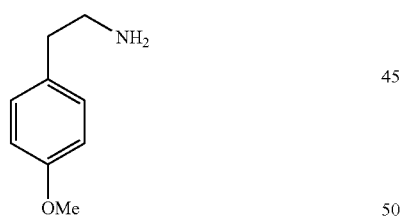
18
Acids
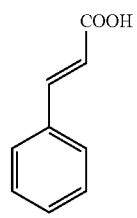
A
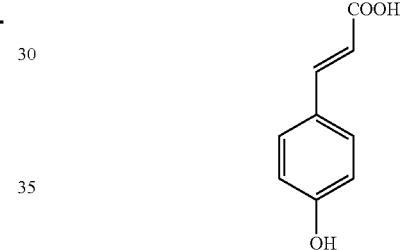
B
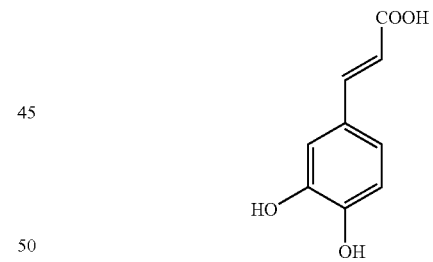
C
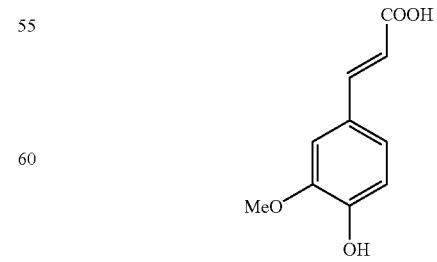
D -continued
Scheme 2. Synthesis of a library of compounds based on 1.
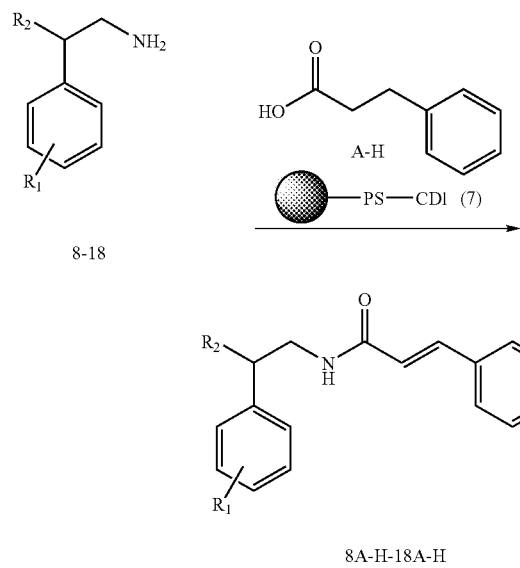
8-18
8A-H-18A-H
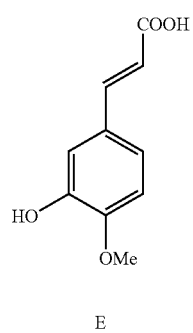
E
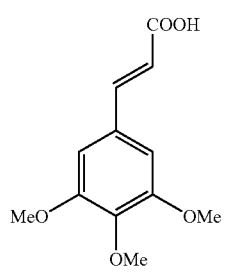
F
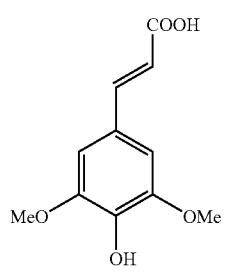
G
-continued
Scheme 2. Synthesis of a library of compounds based on 1.
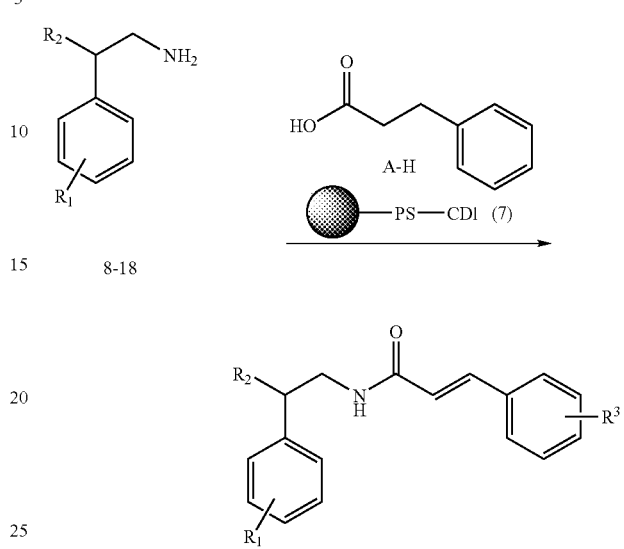
8-18
8A-H-18A-H
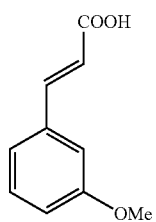
H
Scheme 2B
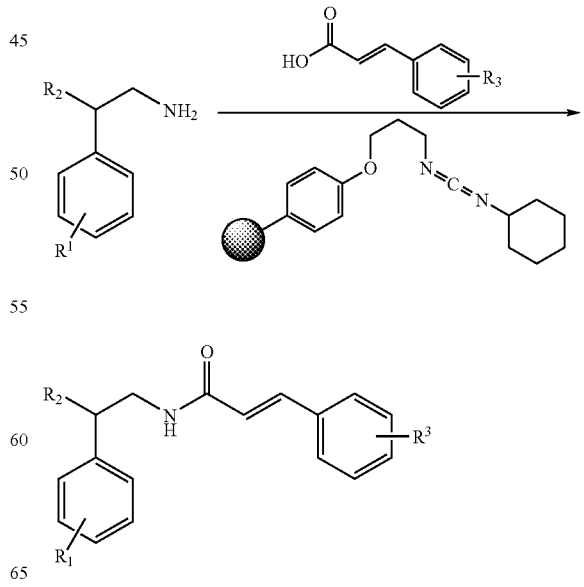

Example 2

Screening for Activity, Apoptotic Properties, and Toxicity

A three-tiered system was devised to identify compounds that selectively induce apoptosis in cancer cells. First, all compounds were screened at 100 μM in a high-throughput manner for their ability to induce death in two cancer cell lines, HL-60 (leukemia) and U-937 (lymphoma). Those molecules that showed cytotoxicity in both cell lines were then evaluated for their apoptotic versus necrotic properties. Those compounds that induced apoptosis then had their toxicity to non-cancerous white blood cells assessed.

Several of the 88 compounds were able to induce cell death at 100 μM in U-937 and HL-60 cells as measured by a dye bio-reduction assay (Table 1). The numbers in Table 1 reflect percentages of cell death. Neither compound 1 nor any library members showed activity in assays exploring inhibition of etoposide induced apoptosis.

TABLE 1

Induction of death in U-937 cells by library members at 100 μM.

|   | 8  | 9   | 10 | 11  | 12 | 13  | 14  | 15  | 16 | 17 | 18 |
|---|----|-----|----|-----|----|-----|-----|-----|----|----|----|
| A | 70 | 24  | 51 | 26  | 26 | 43  | 28  | 27  | 58 | 48 | 56 |
| B | 34 | 20  | 60 | 60  | 47 | 49  | 27  | 39  | 66 | 32 | 17 |
| C | -5 | -12 | -8 | -9  | 27 | -36 | -15 | -29 | 24 | 15 | 26 |
| D | 20 | 20  | 31 | 34  | 82 | 87  | 59  | 89  | 39 | 58 | 66 |
| E | 56 | 41  | 55 | 41  | 28 | 43  | 35  | 22  | 60 | 18 | 73 |
| F | 31 | 13  | 45 | 27  | 33 | 22  | 26  | 12  | 30 | 9  | 40 |
| G | -3 | -7  | 16 | -11 | 41 | 16  | 48  | 47  | 20 | 26 | 35 |
| H | 60 | 38  | 72 | 14  | 51 | 43  | 38  | 24  | 57 | 41 | 56 |

The three most potent of these compounds, 12-D, 13-D, and 15-D were subsequently re-synthesized, purified, and tested at multiple concentrations to determine $IC_{50}$ values. Compound 13-D was the most potent, with an $IC_{50}$ value of 44 μM in U-937 cells, and compounds 12-D and 15-D had IC50 values of 61 and 109 μM respectively.

Further experiments assessed whether the observed death from 12-D, 13-D, and 15-D was due to apoptosis or necrosis. In this regard, compound 13-D induced apoptosis. Cells treated with this molecule showed several hallmarks of apoptotic cell death including strong induction of caspase-3 activity (FIG. 2A) and staining with the apoptotic-specific dye JC-9 (FIG. 2B) as assessed by flow cytometry; JC-9 provides a sensitive readout on mitochondrial depolarization, and dyes of this class are commonly used to quantitate apoptosis (Cossarizza, A.; Salvioli, S. Methods Cell Biol. 2001, 63, 467-486). In this case, 100 μM 13-D has induced apoptosis in over 70% of the cell population after 72 h (as quantitated from FIG. 2B). Additional evidence of apoptosis is provided by microscopy, which shows membrane blebbing and cell shrinkage in the 13-D treated samples (see supporting information). Compounds 12-D and 15-D induced some apoptosis, some necrosis.

Figure 2:
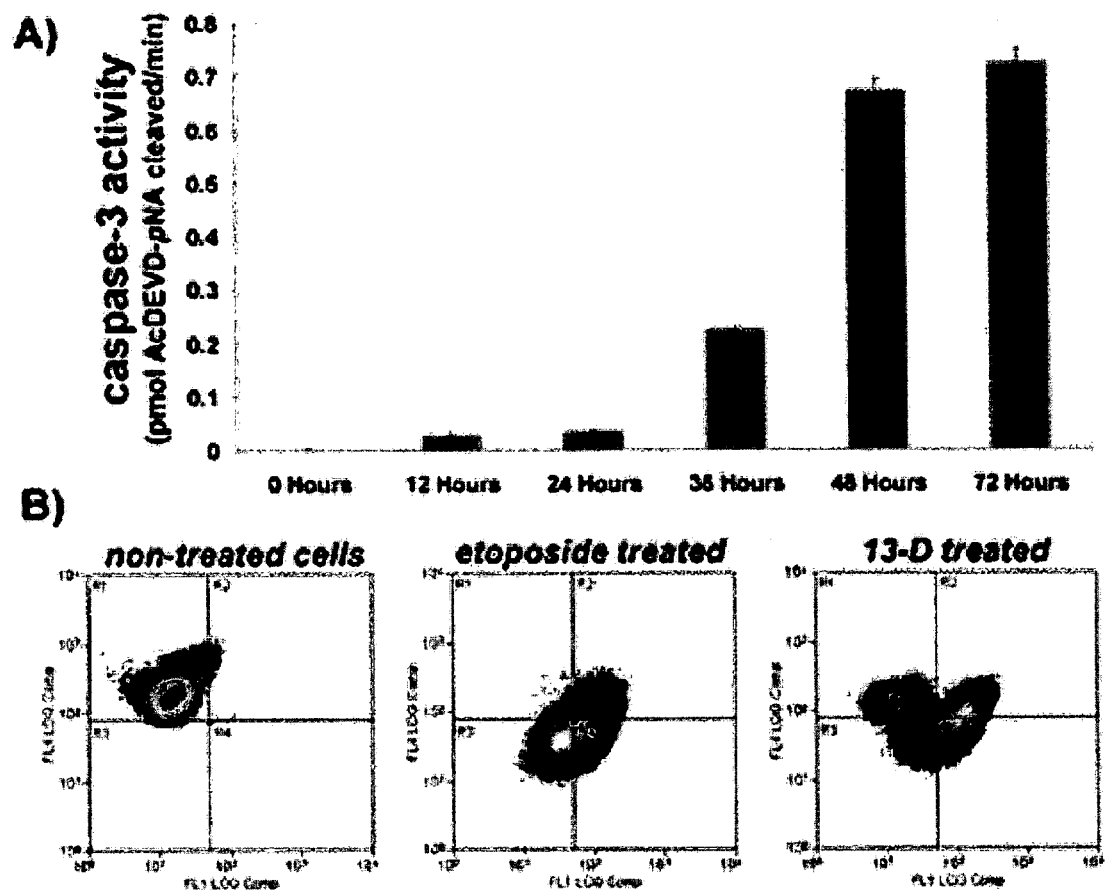
FIG. 2 illustrates induction of apoptosis by compound 13-D.

In another approach, the assay in FIG. 2B is used to quantitate death, in addition to the MTS assay which is also useful in determinations of $IC_{50}$ values.

The selectivity of 13-D for cancerous white blood cells over non-cancerous white blood cells was determined. For this experiment, the spleen from a euthanized mouse was harvested, and the splenocytes isolated. Mouse splenocytes are commonly used to assess the toxicity of small molecules. For examples see: (a) Prater, M. R.; Gogal, R. M.; Blaylock, B. L.; Longstreth, J.; Holladay, S. D. Food Chem. Toxicol. 2002, 40, 1863-1873. (b) Blake, C. A.; Nair-Menon, J. U.; Campbell, G. T. Endocrine 1997, 6, 243-249. (c) Yamaura, K.; Ogawa, K.; Yonekawa, T.; Nakamura, T.; Yano, S.; Ueno, K. Biol. Pharm. Bull. 2002, 25, 201-205. (d) Li, Q.; Hirata, Y.; Piao, S.; Minami, M. Toxicology 2000, 150, 179-189.

The T-cells were then stimulated to grow by the addition of concanavalin A. Remarkably, as the images in FIG. 3 show, high concentrations (500 μM) of compound 13-D showed virtually no toxicity towards the actively dividing splenocytes, while almost completely killing the cancerous U-937 cells. The IC50 of 13-D was 44 μM for the cancerous U-937 cells, but greater than 1000 μM for the non-cancerous splenocytes. Additionally, in a separate experiment T-cells were purified from the heterogeneous splenocyte mixture, stimulated to grow with concanavalin A, and death was assessed after 72 h in the presence or absence of 500 μM 13-D. Again, 13-D had virtually no effect on these purified non-cancerous cells (see supporting information for details).

We have identified small molecules that selectively induce apoptosis in cancerous white blood cells but are non-toxic toward non-cancerous white blood cells. A synthetic route for the synthesis of natural product 1 (also designated as structure 9-D) and a library of derivatives has been developed.

Supporting Information for Examples 1 and 2

The supporting information regards experimental protocols and characterization data.

Materials and Methods.

$^1H$ and $^{13}C$ NMR spectra were recorded on Varian Unity400 (400 MHz $^1H$, 100 MHz $^{13}C$) and on Varian Unity500 (500 MHz $^1H$, 125 MHz $^{13}C$) spectrometers in deuterochloroform ($CDCl_3$) or deuteromethanol ($CD_3OD$). The data is reported as follows: chemical shifts in ppm (δ=delta), multiplicities are indicated as s-singlet; d-doublet; t-triplet; q-quartet; m-multiplet, br-broad. Coupling constants, J, are reported in Hz. Infrared spectra were recorded on Perkin Elmer Spectrum BX spectrophotometer, referenced to polystyrene standard, and the peaks reported in $cm^{-1}$. Mass spectra were recorded by the University of Illinois Mass Spectroscopy Center, and the data reported in m/e (intensity to 100%). Analytical thin-layer chromatography was performed on Merk silica gel plated with F254 indicator. The plates were visualized by UV light, Iodine($I_2$) and/or CAM stain. Optical rotations were obtained on Jasco DIP-360 Digital Polarimeter. Analytical chiral supercritical fluid chromatography (SFC) was performed on Berger Instruments SFC equipped with Diacel Chiracel OD column (250×4.5 mm), internal spectrophotometric detector operated at wavelength 220 nM. Solvents for extraction and chromatography were reagent grade and were used without further purification. Melting points were determined on a Thomas-Hoover Capillary Melting Point Apparatus and are uncorrected. The pH of solutions was measured by Aquemet™ Research AR15 pH meter equipped with Corning semimicrocombo electrode (#476156), which was standardized by 5 buffer solutions (pH=4.0±0.01, 6.0±0.01, 7.0±0.01, 9.0±0.01 and 10.0±0.01) prior to measurements.

Acids A-G were purchased from Aldrich and used as received. Acid H was prepared by Wadsworth-Emmons olefination following a procedure described in *Organic Synthesis*, CV 5, p. 547 from anisaldehyde, which was purchased from Aldrich. PS-carbodiimide resin was purchased from Argonaut Technologies (1101 Chess Dr. Foster City, Calif. 94404). N-Cbz-1-Aryl-2-aminoethanols were prepared as previously reported (Nesterenko, V.; Byers, J. T.; Hergenrother, P. J. Org. Lett. 2003, 5, 281-284). Amines 16, 17, 18 were purchased from Aldrich.

General Procedure for Asymmetric Aminohydroxylation of Styrenes

As described for the synthesis of [(S)-2-hydroxy-2-(4-acetoxy-phenyl)-ethyl]-carbamic acid benzyl ester (5):

In a 1000 mL round bottom three-neck flask, under an atmosphere of $N_2$, benzyl carbamate was dissolved (2.849 g, 18.6 mmol) in 120 mL of acetonitrile. The solution was cooled down in a water-ice bath (0-4° C.) and under efficient stirring a cold solution of potassium hydroxide (0.758 g KOH in 80 mL of water) was added. The solution was stirred 2 minutes, then a cold solution of tert-butyl hypochlorite (1.344 g, 12.4 mmol) in 20 mL of acetonitrile was added; the solution was then stirred for 10 min. A solution of potassium osmate (88.9 mg, 0.241 mmol) in 20 mL of cold $H_2O$ was then added. After 2 min a solution of $DHQ_2AQN$ (280.0 mg, 0.326 mmol) in 20 mL of $CH_3CN$ was added, then a solution of 100 mL of cold acetonitrile was added and stirred for 3 min. Potassium phosphate buffer (240 mL, pH=7.57) was added, the cooling bath removed, and the solution allowed to stir for 5 min (the solution turned light green immediately). At this point the pH was checked and if necessary adjusted to pH=7.65±0.02 by addition of a monobasic sodium phosphate solution. A solution of styrene (1.005 mg, 6.2 mmol) in 40 mL of acetonitrile was then added in one portion. The reaction mixture was vigorously stirred at room temperature (21-23° C.). After 45-50 min the solution turns yellow, indicating completion (as verified by TLC disappearance of starting material).

The reaction mixture was cooled to 0-4° C. in an ice bath and 2.04 g of sodium sulfite in 20 mL of water was added. After 15 min of stirring the organic layer was separated and the aqueous layer was extracted with ethyl acetate (3×150 mL). The combined organic extracts were washed with water (2×100 mL) and brine (3×100 mL), and dried over anhydrous magnesium sulfate. Solvent evaporation resulted 4.186 g of amorphous crystals, which was subjected to flash column chromatography (silica gel, 2:1=Hexane: EtOAc) to yield 1.410 g of 5 (71% isolated yield, 73% ee) as colorless crystals. The material was crystallized from EtOAc/hexane mixture (to a boiling suspension in hexanes (130 mL) EtOAc was added in portions until clear solution is obtained (37 mL)) to afford 0.380 g of colorless plate-like crystals (20% ee) after filtration. The solution obtained after filtration was evaporated and recrystallized as described above second time to yield 0.882 g (43% of theoretical yield) of needle-like crystals (>99% ee), 0.106 g of material remained in solution (>97% ee).

SFC (125 psi $CO_2$, 12%, 3 mL/min MeOH, Chiracel OD) 6.951 min (R), 7.384 (S) $[\alpha]^{25}_D$=29.64901 (c=0.895, $CHCl_3$, $[\alpha]^{25}_D$=−16.7102 in MeOH at c=0.31) (enantiomer, obtained with $DHQD_2AQN$ ligand, resulted $[\alpha]^{25}_D$=−29.6437 (c=0.98, $CHCl_3$)).

The following compounds were synthesized according to the general protocol above on a 6.2 mmol scale; characterization data has been reported previously.[1] Yields below are of the single regioisomer after chromatography, and the enatiomeric ratios were determined after crystallization, as described above.

TABLE 2

Products of aminohydroxylation. Characterization is as described by Nesterenko et al., P. J. Org. Lett. 2003, 5, 281-284.

| Compound | % Yield from aminohydroxylation | er after crystallization | $[\alpha]^{25}$ |
|---|---|---|---|
| 5 (HO, NHCBz, phenyl with OAc) | 71% | >99:1 | 29.64901 (c = .895, $CHCl_3$), 16.7102 (c = .31, MeOH) |
| 5a (HO, NHCbz, phenyl) | 59% | >99:1 | |
| 5b (HO, NHCBz, phenyl with $OCH_3$) | 65% | 96.3:3.7 | 26.38912 (c = .52, $CHCl_3$), |

TABLE 2-continued

Products of aminohydroxylation. Characterization is as described by Nesterenko et al., P. J. Org. Lett. 2003, 5, 281-284.

| | % Yield from aminohydroxylation | er after crystallization | $[\alpha]^{25}$ |
|---|---|---|---|
|  5c | 73% | >99:1 | −29.64347 (c = .895, CHCl$_3$) |

General procedure for O-methylation of N-Cbz-2-amino-1-phenyl-ethanols

As described for the synthesis of [(S)-2-methoxy-2-(4-acetoxy-phenyl)-ethyl]-carbamic acid benzyl ester (6): An oven dried 50 mL round bottom flask, equipped with septum and Teflon coated magnetic stir bar, was charged with 5 (329.5 mg, 1 mmol), evacuated for 15 min at 0.01 mm Hg and flushed with dry N$_2$. After repeating the cycle three times, freshly distilled THF (15 mL) was added via syringe and the solution cooled in a dry ice-acetone bath (−78° C. external, −74° C. internal) for 10 minutes. A solution of n-butyllithium (1.26 mL, 2.02 mmol, 1.6 M in hexanes) was added via syringe and after stirring for 1 min methyltriflate (237 μL, 344 mg, 2.1 mmol) was added, and the mixture stirred for 1.5 h at −74° C. The reaction mixture was poured onto 100 mL of cold 1% HCl and extracted with ether (4×30 mL), washed with 5% sodium bicarbonate and brine (2×30 mL), and dried over anhydrous magnesium sulfate. Solvent evaporation resulted in 329.1 mg of an oily substance, which was subjected to column chromatography (silica gel, 4:1=Hexane: EtOAc) to yield 246 mg (71%) of colorless oil 6.

TABLE 3

Yields for methylation reactions generating products 6, 6a, 6b, and 6c.

Analytical Data for Alkylated Carbamates.

Acetic acid 4-(2-benzyloxycarbonylamino-1-(S)-methoxy-ethyl)-phenyl ester (6):

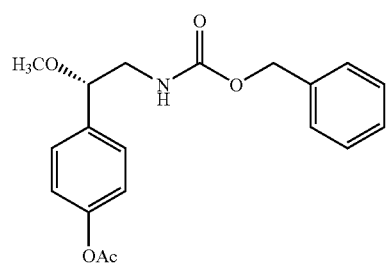

$C_{19}H_{21}NO_5$
Exact Mass: 343.14
Mol. Wt.: 343.37
C, 66.46; H, 6.16; N, 4.08; O, 23.30

Synthesized by general procedure for methylation, above. HMR $^1$H (400 MHz, CDCl$_3$) δ ppm: 7.35 (m, 6H); 7.31 (d, 2H, J1=8.6 Hz); 7.08 (d, 2H, J1=8.5 Hz); 5.30 (br. s, 1H); 5.11 (d, 2H, J1=2.7 Hz); 4.28 (dd, 1H, J1=8.6 Hz, J2=3.7 Hz); 3.53 (ddd, 1H, J1=7.8 Hz, J2=4.0 Hz, J3=12.0 Hz); 3.23 (s, 3H); 3.21 (ddd overlaid with singlet, 1H, J1=9.7 Hz, J2=5.1 Hz, J3=13.9 Hz); 2.29 (s, 3H). NMR $^{13}$C (125 MHz, CDCl$_3$) δ ppm: 169.3; 156.3; 150.4; 136.5; 136.4; 128.4; 128.0; 127.6; 121.6; 81.9; 66.6; 56.8; 47.2; 21.0. R$_f$=9 mm/50 mm (EtOAc/Hexanes=25/75); colorless oil. IR (thin film, cm$^{-1}$): 3342, 3065, 3034, 2984, 2936, 2899, 2825, 1755, 1722, 1606, 1537, 1505, 1455, 1370, 1216, 1201, 1165, 1109, 1075, 1016, 912, 849, 776. MS (FAB): 344.09 (M+1, 66.55); 312.09 (M−31, 100.00); 268.09 (44.44); 222.05 (20.64); 179.06 (22.31); 164.08 (11.89); 155.00 (16.87); 152.00 (25.53); 137.05 (46.16); 118.98 (55.43). HRMS (FAB): 344.1500 (C$_{19}$H$_{22}$NO$_5$, M+1; calc. 344.149798). SFC (125 psi CO$_2$; 15%, 3 mL/min MeOH, Chiracel OD): 3.672 min (R), 3.865 min (S), 1.11:98.89 er, 97.78% ee.

(2-Methoxy-2-phenyl-ethyl)-carbamic acid benzyl ester (6a)

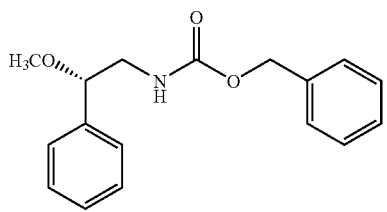

C$_{17}$H$_{19}$NO$_3$
Exact Mass: 285.14
Mol. Wt.: 285.34
C, 71.56; H, 6.71; N, 4.91; O, 16.82

Synthesized by general procedure for methylation, above. HMR $^1$H (400 MHz, CDCl$_3$) δ ppm: 7.37 (m, 6H); 7.32 (m, 4H); 5.28 (br. s, 1H); 5.12 (d, 2H, J1=2.0 Hz); 4.29 (dd, 1H, J1=8.5 Hz, J2=3.6 Hz); 3.57 (ddd, 1H, J1=7.8 Hz, J2=3.8 Hz, J3=12.0 Hz); 3.28 (ddd overlaid with singlet, 1H, J1=8.7 Hz, J2=4.1 Hz); 3.25 (s, 3H). NMR $^{13}$C (125 MHz, CDCl$_3$) δ ppm: 168.5; 156.3; 138.9; 136.5; 128.5; 128.5; 128.1; 128.1; 126.6; 82.5; 66.6; 56.7; 47.2. R$_f$=20 mm/50 mm (EtOAc/Hexanes=25/75); colorless oil. IR (Thin film, cm$^{-1}$) 3339, 3063, 3032, 2982, 2936, 2884, 2825, 1714, 1537, 1519, 1455, 1249, 1145, 1109, 1065, 756. MS (FAB): 286.09 (M+1, 100.00); 254.07 (M−31, 51.24); 210.1 (23.17); 164.05 (27.7); 134.97 (29.82); 118.96 (42.44). HRMS (FAB): 286.1450 (C$_{17}$H$_{20}$NO$_3$, M+1; calc 286.144319).

[2-Methoxy-2-(4-methoxy-phenyl)-ethyl]-carbamic acid benzyl ester (6b)

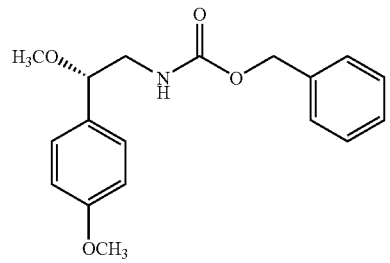

C$_{18}$H$_{21}$NO$_4$
Exact Mass: 315.15
Mol. Wt.: 315.36
C, 68.55; H, 6.71; N, 4.44; O, 20.29

Synthesized by general procedure for methylation, above. HMR $^1$H (400 MHz, CDCl$_3$) δ ppm: 7.37 (m, 5H); 7.22 (d, 2H, J1=8.4 Hz); 6.89 (d, 2H, J1=8.6 Hz); 5.21 (br. s, 1H); 5.11 (d, 2H, J1=1.1 Hz); 4.22 (dd, 1H, J1=8.4 Hz, J2=3.9 Hz); 3.81 (s, 3H); 3.53 (ddd, 1H, J1=7.8 Hz, J2=3.9 Hz, J3=12.2 Hz); 3.27 (ddd overlaid with singlet, 1H, J1=8.6 Hz, J2=4.0 Hz, J3=13.3 Hz).

NMR $^{13}$C (125 MHz, CDCl$_3$) δ ppm: 159.5; 156.3; 136.5; 130.9; 128.5; 128.1; 127.9; 114.0; 82.0; 66.7; 56.5; 55.2; 47.2. R$_f$=14 mm/50 mm (EtOAc/Hexanes=25/75); colorless oil. [α]$^{25}_D$=26.638912 (c=0.895, CHCl$_3$). IR (thin film, cm$^{-1}$): 3377, 3002, 2937, 2840, 1708, 1611, 1523, 1513, 1463, 1444, 1365, 1308, 1262, 1235, 1173, 1113, 1078, 1027, 986, 826, 760. MS (FAB): 316.09 (M+1, 8.04); 284.07 (M−31, 100.00); 240.1 (14.64); 194.06 (17.08); 151.06 (39.63); 134.99 (23.88); 118.97 (34.28). HRMS (FAB): 316.1553 (C$_{18}$H$_{22}$NO$_4$, M+1, calc. 316.154883).

Acetic acid 4-(2-benzyloxycarbonylamino-1-(S)-methoxy-ethyl)-phenyl ester (6c)

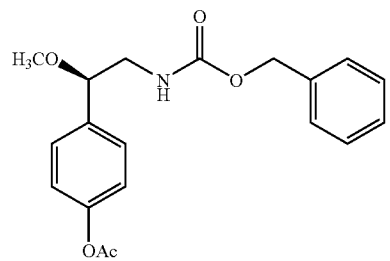

C$_{19}$H$_{21}$NO$_5$
Exact Mass: 343.14
Mol. Wt.: 343.37
C, 66.46; H, 6.16; N, 4.08; O, 23.30

Synthesized by general procedure for methylation, above. HMR $^1$H (400 MHz, CDCl$_3$) δ ppm: 7.36 (m, 5H); 7.31 (d, 2H, J1=6.6 Hz); 7.08 (d, 2H, J1=8.6 Hz); 5.22 (br. s, 1H); 5.11 (d, 2H, J1=1.3 Hz); 4.28 (dd, 1H, J1=8.5 Hz, J2=4.0 Hz); 3.54 (ddd, 1H, J1=7.8 Hz, J2=4.0 Hz, J3=12.0 Hz); 3.24 (s, 3H); 3.21 (ddd overlaid with singlet, 1H, J1=9.7 Hz, J2=5.4 Hz, J3=13.9 Hz); 2.30 (s, 3H). NMR $^{13}$C (100 MHz, CDCl$_3$) δ ppm: 169.4; 156.3; 150.4; 136.5; 136.4; 128.5; 128.1; 127.7; 121.7; 82.0; 66.7; 56.9; 47.3. R$_f$=9 mm/50 mm (EtOAc/

Hexanes=25/75); colorless oil. $[\alpha]^{25}_D = -29.6437$ (c=0.98, CHCl$_3$). IR (thin film, cm$^{-1}$): 3342, 3065, 3034, 2984, 2937, 2899, 2825, 1755, 1722, 1606, 1531, 1505, 1455, 1370, 1217, 1203, 1165, 1110, 1074, 1016, 912, 849, 776. MS (FAB): 344.09 (M+1, 56.86); 312.05 (M−31, 100.00); 268.09 (60.67); 222.05 (20.90); 179.05 (33.58); 167.02 (18.52); 165.00 (18.90); 155.00 (36.59); 151.97 (42.26); 137.05 (62.70); 118.98 (72.01). HRMS (FAB): 344.1500 (C$_{19}$H$_{22}$NO$_5$, M+1; calc. 344.149798). SFC (125 psi CO$_2$; 8%, 3 mL/min MeOH, Chiracel OD): 7.83 min (R), >99% ee.

Procedure and Analytical Data for Hydrolysis of 6 and 6c:

[2-(4-Hydroxy-phenyl)-2-(S)-methoxy-ethyl]-carbamic acid benzyl ester (6d): To a solution of 6 (160 mg, 0.46 mmol) in EtOH (5 mL) 0.568 g of a freshly prepared solution of potassium hydroxide (253.2 mg in 5.013 g H$_2$O, 0.045 M) was added. The mixture was stirred at 23-25° C. for 1 h (completion monitored by TLC) and neutralized with 0.1% HCl (neutral by pH indicator paper). Solvent was evaporated in vacuo and the residue dissolved in ethyl acetate and flash filtered through a pad of silica gel to remove inorganic impurities. The silica gel was washed with ethyl acetate, fractions combined and solvent evaporated in vacuo to afford 136 mg (97%) of 6d.

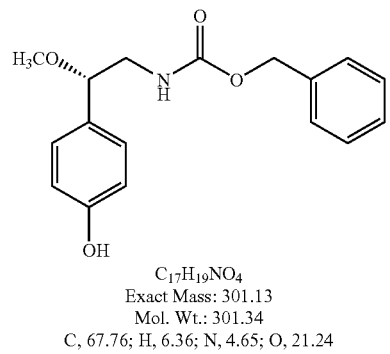

6d

C$_{17}$H$_{19}$NO$_4$
Exact Mass: 301.13
Mol. Wt.: 301.34
C, 67.76; H, 6.36; N, 4.65; O, 21.24

HMR $^1$H (500 MHz, CDCl$_3$) δ ppm: 7.46 (br. s, 1H); 7.35 (m, 5H); 7.11 (d, 2H, J1=8.3 Hz); 6.83 (d, 2H, J1=8.3 Hz); 5.47 (br. s, 1H); 5.13 (s, 2H); 4.21 (dd, 1H, J1=8.6 Hz, J2=3.7 Hz); 3.53 (ddd, 1H, J1=7.7 Hz, J2=3.9 Hz, J3=12.1 Hz); 3.27 (ddd overlaid with singlet, 1H, J1=8.7 Hz, J2=4.1 Hz, J3=13.3 Hz); 3.20 (s, 3H). NMR $^{13}$C (125 MHz, CDCl$_3$) δ ppm: 156.8; 156.4; 136.2; 129.8; 128.4; 128.1; 128.0; 127.9; 115.5; 82.0; 66.9; 56.4; 47.2. R$_f$=14 mm/50 mm (EtOAc/Hexanes=25/75).

[2-(4-Hydroxy-phenyl)-2-(R)-methoxy-ethyl]-carbamic acid benzyl ester (6e): To a solution of 6c (132 mg, 0.35 mmol) in EtOH (5 mL) 0.469 g of a freshly prepared solution of potassium hydroxide (253.2 mg in 5.013 g H$_2$O, 0.045M, 1.1eq.) was added. The mixture was stirred at 23-25° C. for 1 h (completion monitored by TLC) and neutralized with 0.1% HCl (neutral by pH indicator paper). Solvent was evaporated in vacuo and the residue dissolved in ethyl acetate and flash filtered through a pad of silica gel to remove inorganic impurities. The silica gel was washed with ethyl acetate, fractions combined and solvent evaporated in vacuo to afford 107 mg (92%) of 6e.

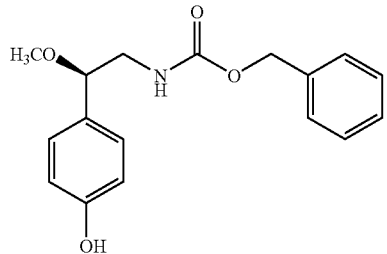

6e

C$_{17}$H$_{19}$NO$_4$
Exact Mass: 301.13
Mol. Wt.: 301.34
C, 67.76; H, 6.36; N, 4.65; O, 21.24

HMR $^1$H (400 MHz, CDCl$_3$) δ ppm: 7.35 (m, 5H); 7.17 (br. s, 1H); 7.10 (d, 2H, J1=8.3 Hz); 6.82 (d, 2H, J1=8.3 Hz); 5.42 (br. s, 1H); 5.13 (s, 2H); 4.20 (dd, 1H, J1=8.6 Hz, J2=3.7 Hz); 3.52 (ddd, 1H, J1=7.7 Hz, J2=3.7 Hz, J3=12.1 Hz); 3.26 (ddd overlaid with singlet, 1H, J1=8.7 Hz, J2=4.1 Hz, J3=13.3 Hz); 3.20 (s, 3H). NMR $^{13}$C (100 MHz, CDCl$_3$) δ ppm: 156.8; 156.3; 136.2; 130.0; 128.5; 128.2; 128.1; 128.0; 115.5; 82.1; 66.9; 56.4; 47.3. R$_f$=14 mm/50 mm (EtOAc/Hexanes=25/75);

Compounds 6f and 6g (see Table 4, below) were obtained by the hydrolysis of 5 and 5c, respectively. This hydrolysis was performed exactly as described for 6d, above.

General Procedure for Deprotection of Cbz Group

As described the synthesis of (S)-4-(2-Amino-1-methoxy-ethyl)-phenol (9): 5% Pd/C (48 mg, 2.4 mg Pd, 1.5 wt. %) was loaded in a 25 mL tube-shaped flask, equipped with a magnetic stirrer, a hydrogen balloon and a vacuum outlet. The flask was evacuated for 5 min at 0.001 mm Hg and flushed with H$_2$. After repeating the cycle 4 times the catalyst was suspended in EtOH (4 mL) and 6d (136.0 mg, 0.45 mmol), was added as a solution in EtOH (2 mL) and the mixture was stirred under hydrogen atmosphere for 8 h. Upon completion (monitored by TLC by disappearance of the starting material), the solution was filtered with celite. The celite was washed with EtOH (3×3 mL) and solvent was removed in vacuum and the residue dried at 20-23° C. for 1 h at 0.01 mm Hg to give 73.6 mg of a crystalline substance (Table 4). The presence of the amine was verified by ninhydrin stain and the product was used in the next step for coupling. Due to relative instability of the amine products, they were immediately coupled to the appropriate acid, and were not characterized. For the library synthesis, all Cbz deprotections were performed in parallel, and the amines were then used immediately to create the library.

TABLE 4

Synthesis of amino building blocks by deprotection of carbamates.

| Entry | Carbamate | Loaded, mg | Pd, wt % | Amine product | yield, % |
|---|---|---|---|---|---|
| 1. | 6a | 160.0 | 1.4 | 8 | 54.3% |
| 2. | 5a | 132.5 | 1.51 | 12 | 88% |
| 3. | 6d | 136 | 1.39 | 9 | 97% |
| 4. | 6f | 144 | 1.42 | 13 | 85% |
| 5. | 6e | 98 | 1.46 | 11 | 85% |

TABLE 4-continued

Synthesis of amino building blocks by deprotection of carbamates.

| Entry | Carbamate | Loaded, mg | Pd, wt % | Amine product | yield, % |
|---|---|---|---|---|---|
| 6. | 6g | 142.1 | 1.49 | 15 | 87% |
| 7. | 6b | 132 | 1.48 | 10 | 94% |
| 8. | 5b | 134 | 1.46 | 14 | 86% |

Procedure and Analytical Data for Amides (1H and $^{13}$C Spectra Follow)

Amides were prepared by both solution and solid phase couplings of appropriate amine and acid building blocks. Solution phase reaction was generally used for scale up reactions, but required more tedious chromatography to purify the products. The $^{1}$H and $^{13}$C spectra are below.

3-(4-Hydroxy-3-(S)-methoxy-phenyl)-N-[2-(4-hydroxy-phenyl)-2-methoxy-ethyl]-acrylamide (1,9-D): METHOD 1-solid-phase coupling. An oven dried 15 mL round bottom flask, equipped with a Teflon-coated magnetic stir bar, was charged with polystyrene-carbodiimide (PS-CDI) (45 mg, 0.0576 mmol, 2eq. 1.28 mmol/g), evacuated for 15 min at 0.01 mm Hg and flushed with dry $N_2$. After repeating the cycle three times, freshly distilled THF (5 mL) was added via syringe followed by a solution of ferulic acid (6.0 mg, 0.031 mmol, 1.1 eq) in THF (0.4 mL). Compound 9 (4.7 mg, 0.028 mmol, 1 eq.) was added as solution in THF (0.5 mL) and the mixture is stirred at 20-22° C. for 6-8 h. The beads were filtered off and washed with THF (3×1 mL). The organic washes were combined and solvent evaporated to afford 9.1 mg of oily substance, which was subjected to column chromatography (silica gel, 1:7=Hexane:EtOAc) to yield 3.3 mg (37%) of 9-D as an amorphous substance.

3-(4-Hydroxy-3-(S)-methoxy-phenyl)-N-[2-(4-hydroxy-phenyl)-2-methoxy-ethyl]-acrylamide (1,9-D): METHOD 2-solution-phase coupling. An oven dried 25 mL round bottom flask, equipped with a Teflon coated magnetic stir bar, was evacuated for 15 min at 0.01 mm Hg and flushed with dry $N_2$. After repeating the cycle three times, the flask was charged with dicyclohexylcarbodiimide (19.5 mg, 0.095 mmol, as a solution in THF, 2.1 mL) followed by a solution of D (18.3 mg, 0.095 mmol per 2.1 mL) in THF (2.1 mL). Amine 9 (15.1 mg, 0.09 mmol) was added as a solution in THF/DMF (8:1, 2.1 mL) and the mixture was stirred at 20-22° C. for 10 h. Upon completion (monitored by TLC, by disappearance of the amine) solvent evaporation resulted 52.1 mg of a viscous oil. The mixture then was subjected to column chromatography (silica gel, 1:4=Hexane: EtOAc) to yield 21.4 mg (71%) of 9-D as a light-yellow viscous oil.

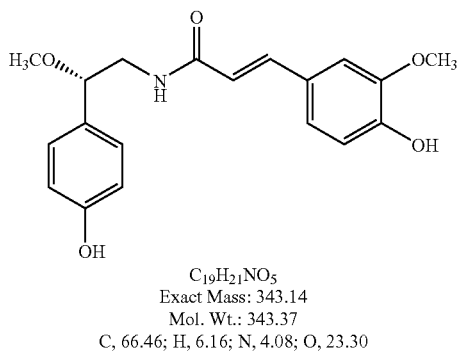

$C_{19}H_{21}NO_5$
Exact Mass: 343.14
Mol. Wt.: 343.37
C, 66.46; H, 6.16; N, 4.08; O, 23.30

NMR $^{13}$C (125 MHz, CD$_3$OD) δ ppm: 7.43 (d, 1H, J1=15.9 Hz); 7.17 (app. dt, 2H, J1=6.4 Hz, J2=1.7 Hz); 7.12 (d, 1H, J1=1.6 Hz); 7.03 (dd, 1H, J1=8.1 Hz, J2=1.7 Hz); 6.79 (d, 1H, J1=1.7 Hz); 6.79 (d, 1H, J1=2.4 Hz); 6.78 (d, 1H, J1=1.9 Hz); 6.47 (d, 1H, J1=15.9 Hz); 4.24 (dd, 1H, J1=8.6 Hz, J2=4.5 Hz); 3.87 (s, 3H); 3.52 (dd, 1H, J1=13.7 Hz, J2=4.5 Hz); 3.40 (dd, 1H, J1=13.7 Hz, J2=8.6 Hz); 3.20 (s, 3H). NMR $^{13}$C (125 MHz, CD$_3$OD) δ ppm: 169.2; 158.6; 149.9; 149.3; 142.3; 131.4; 129.2; 128.3; 127.1; 123.3; 118.7; 116.5; 116.3; 111.5; 83.3; 56.8; 56.4; 47.1. R$_f$=14 mm/50 mm (EtOAc/Hexanes=75/25); [α]$^{25}$$_D$=−28.8805 (c=1.23, MeOH). IR (KBr, cm$^{-1}$): 3398, 2937, 2826, 1654, 1648, 1596, 1515, 1458, 1271, 1254, 1209, 1032, 837. MS (FAB): 344.2 (M+1), 312.1 (M−31). HRMS (FAB): 344.1500 (C$_{19}$H$_{22}$NO$_5$, M+1; calc. 344.149798). MS (ESI) (m/z): 708.85 (2M+Na, 6.60), 343.84 (M+1, 100.00), 312.05 (M−31, 43.11). UV (PDA; λ$_{max}$, m): 225, 295, 320;

3-(4-Hydroxy-3-methoxy-phenyl)-N-(2-hydroxy-2-phenyl-ethyl)-acrylamide (12-D): An oven dried 50 mL round bottom flask, equipped with a Teflon coated magnetic stir bar, was evacuated for 15 min at 0.01 mm Hg and flushed with dry $N_2$. After repeating the cycle three times, the flask was charged with dicyclohexylcarbodiimide (59.3 mg, 0.287 mmol, as a solution in THF, 5 mL) followed by a solution of D (53.4 mg, 0.275 mmol) in THF (5 mL). Amine 12 (34.3 mg, 0.25 mmol) was added as solution in THF/DMF (8:1, 5 mL) and the mixture was stirred at 20-22° C. for 10 h. Upon completion (monitored by TLC by disappearance of the amine) solvent evaporation resulted 146.1 mg of viscous oily substance. The mixture then was subjected to column chromatography (silica gel, 1:4=Hexane: EtOAc) to yield 32.1 mg (42%) of 12-D as a viscous oil.

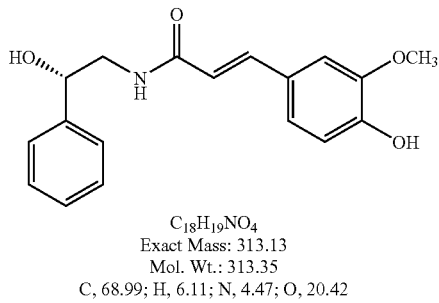

$C_{18}H_{19}NO_4$
Exact Mass: 313.13
Mol. Wt.: 313.35
C, 68.99; H, 6.11; N, 4.47; O, 20.42

HMR $^1$H (CD$_3$OD) δ ppm: 7.43 (d, 1H, J1=15.6 Hz); 7.40 (d, 1H, J1=1.5 Hz); 7.38 (s, 1H); 7.31 (app. t, 2H, J1=7.8 Hz); 7.24 (app. tt, 1H, J1=7.2 Hz, J2=2.2 Hz); 7.10 (d, 1H, J1=2.0 Hz); 7.02 (dd, 1H, J1=8.0 Hz, J2=1.7 Hz); 6.78 (d, 1H, J1=8.2 Hz); 6.45 (d, 1H, J1=15.7 Hz). NMR $^{13}$C (125 MHz, CD$_3$OD) δ ppm: 169.5; 149.9; 149.3; 144.0; 142.3; 129.4; 128.6; 128.2; 127.2; 123.3; 118.5; 116.4; 111.5; 73.7; 56.3; 48.4. R$_f$=15.5 mm/50 mm (EtOAc/Hexanes=75/25); MS (FAB): 314.1 (M+1). HRMS (FAB): 314.1393 (C$_{18}$H$_{20}$NO$_4$, M+1; calc. 314.139233). MS (ESI) (m/z): 313.93 (M+1, 100.00), 296.15 (M−17, 7.54). UV (PDA; λ$_{max}$, m): 220, 295, 320.

N-[2-(S)-Hydroxy-2-(4-hydroxy-phenyl)-ethyl]-3-(4-hydroxy-3-methoxy-phenyl)-acrylamide (13-D): An oven dried 50 mL round bottom flask, equipped with a Teflon coated magnetic stir bar, was evacuated for 15 min at 0.01 mm Hg and flushed with dry $N_2$. After repeating the cycle three times, the flask was charged with dicyclohexylcarbodiimide (59.3 mg, 0.287 mmol, as a solution in THF, 5 mL) followed by a solution of D (53.4 mg, 0.275 mmol) in THF (5 mL). Amine 13 (38.3 mg, 0.25 mmol) was added as solution in THF/DMF (8:1, 5 mL) and the mixture was stirred at 20-22° C. for 10 h. Upon completion (monitored by TLC by disappearance of the amine) solvent evaporation resulted 147 mg of a viscous oily substance. The crude reaction mixture then was subjected to column chromatography (silica gel, 1:4=Hexane: EtOAc) to yield 45 mg (56%) of 13-D as a viscous oil.

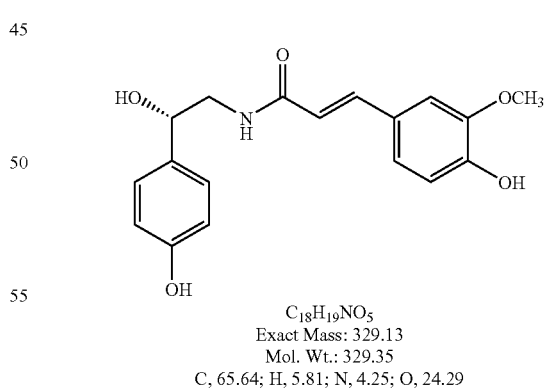

$C_{18}H_{19}NO_5$
Exact Mass: 329.13
Mol. Wt.: 329.35
C, 65.64; H, 5.81; N, 4.25; O, 24.29

HMR $^1$H (CD$_3$OD) δ ppm: 7.42 (d, 1H, J1=15.6 Hz); 7.20 (app. dt, 2H, J1=8.4 Hz); 7.09 (d, 1H, J1=1.7 Hz); 7.01 (dd, 1H, J1=8.3 Hz, J2=2.0 Hz); 6.75 (app. t, 3H, J1=8.5 Hz); 6.45 (d, 1H, J1=15.8 Hz); 4.71 (dd, 1H, J1=7.7 Hz, J2=4.8 Hz); 3.85 (s, 3H); 3.53 (dd, 1H, J1=13.3 Hz, J2=4.8 Hz); 3.43 (dd, 1H, J1=13.5 Hz, J2=7.8 Hz). NMR $^{13}$C (125 MHz, CD$_3$OD) δ ppm: 169.4; 158.1; 149.8; 149.2; 142.2; 134.7; 128.5;

128.2; 123.3; 118.6; 116.4; 116.1; 111.5; 73.4; 56.3; 48.4. $R_f$=6 mm/50 mm (EtOAc/Hexanes=75/25); amorphous crystals. $[\alpha]^{25}_D$=−37.5557 (c=1.376, MeOH). IR (KBr, cm$^{-1}$): 3338, 3276, 2938, 2875, 1654, 1599, 1559, 1517, 1449, 1430, 1369, 1253, 1167, 1127, 1075, 1030, 966, 835; MS (FAB): 330.1 (M+1). HRMS (FAB): 330.1335 ($C_{18}H_{20}NO_5$, M+1; calc. 330.134148). MS (ESI) (m/z): 712.04 (10.07), 329.8 (M+1, 100.00), 312.04 (M−17, 87.74). UV (PDA; $\lambda_{max}$, m): 230, 295, 320.

N-[2-(R)-Hydroxy-2-(4-hydroxy-phenyl)-ethyl]-3-(4-hydroxy-3-methoxy-phenyl)-acrylamide (15-D): An oven dried 50 mL round bottom flask, equipped with a Teflon coated magnetic stir bar, was evacuated for 15 min at 0.01 mm Hg and flushed with dry $N_2$. After repeating the cycle three times, the flask was charged with dicyclohexylcarbodiimide (59.3 mg, 0.287 mmol, as solution in THF, 5 mL) followed by a solution of D (53.4 mg, 0.275 mmol) in THF (5 mL). Amine 15 (38.3 mg, 0.25 mmol) was added as solution in THF/DMF (8:1, 5 mL) and the mixture was stirred at 20-22° C. for 10 h. Upon completion (monitored by TLC by disappearance of the amine) solvent evaporation resulted 149.1 mg of a viscous oily substance. The crude reaction mixture then was subjected to column chromatography (silica gel, 1:4=Hexane: EtOAc) to yield 32.0 mg (40%) of 15-D as a viscous oil.

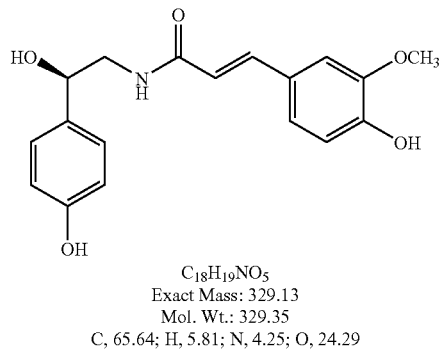

$C_{18}H_{19}NO_5$
Exact Mass: 329.13
Mol. Wt.: 329.35
C, 65.64; H, 5.81; N, 4.25; O, 24.29

HMR $^1$H (CD$_3$OD) δ ppm: 7.43 (d, 1H, J1=15.9 Hz); 7.20 (app. dt, 2H, J1=8.9 Hz); 7.09 (d, 1H, J1=1.9 Hz); 7.01 (dd, 1H, J1=8.2 Hz, J2=1.5 Hz); 6.75 (app. t, 3H, J1=7.6 Hz); 6.45 (d, 1H, J1=15.7 Hz); 4.72 (dd, 1H, J1=7.8 Hz, J2=4.9 Hz); 3.84 (s, 3H); 3.54 (dd, 1H, J1=13.4 Hz, J2=4.9 Hz); 3.44 (dd, 1H, J1=13.7 Hz, J2=7.9 Hz). NMR $^{13}$C (CD$_3$OD) δ ppm: 169.4; 158.1; 149.8; 149.2; 142.2; 134.7; 128.4; 128.2; 123.3; 118.6; 116.4; 116.1; 111.5; 73.4; 56.3; 48.3. $R_f$=22 mm/50 mm (EtOAc/Hexanes=75/25); amorphous crystals. MS (FAB): 330.1 (M+1). HRMS (FAB): 330.1338 ($C_{18}H_{20}NO_5$, M+1; calc. 330.134148). MS (ESI) (m/z): 712.02 (16.97), 329.81 (M+1, 98.90), 312.02 (M−17, 100.00). UV (PDA; $\lambda_{max}$, m): 230, 295, 320.

Figure 9A:
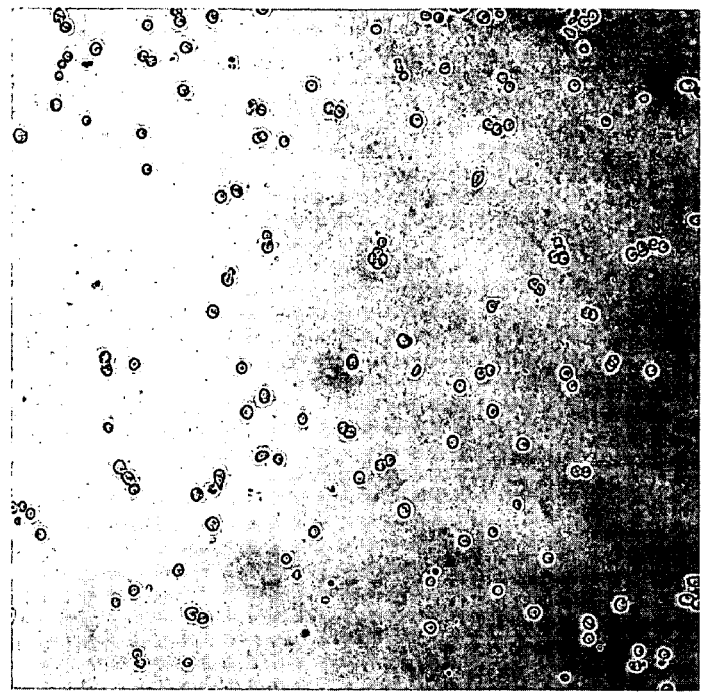
FIG. 9A and FIG. 9B illustrate data from confocal microscopy of U-937 cells cultured in the presence of Compound 13-D; magnification at 100×.

Procedure for Parallel Synthesis of Combinatorial Library:

Polystyrene-carbodiimide beads (Argonaut Technologies Inc., 110 μm, 1.37 mmol/g) were loaded (using the bead loading block; see FIG. 4) into 96 deep well plate (well volume 1 mL, 22 mg/well, 0.03 mol/well, see FIG. 4) and suspended in freshly distilled THF (0.25 mL/well). Solutions of corresponding acid building blocks A-H (0.3 mL, 0.0153 mmol/well) were added in each column, followed by solutions of corresponding amine building blocks 8-18 (0.3 mL, 0.015 mmol/well) added to each row. The 96-well plate was capped with a Teflon lid and rotated (60-80 rpm) for 48 h on a mechanical stirrer so that the beads are freely moving in the solution. Upon completion the beads were filtered off (through a Pasteur pipettes fitted with a cotton plug) and washed with THF (3×0.3 mL). Removal of the solvent in vacuo afforded amide products in 85% average yield. The library was analyzed by TLC and LC-MS. LC-MS was conducted on all 88 members of the library using a reversed-phase C18 column, acetonitrile/$H_2O$ containing 0.1% formic acid. Two representative LC-MS analyses are shown in FIG. 9, below. The mass spectrometer was a Finnigan LCQ decaXP equipped with a Surveyor autosampler, a Surveyor PDA detector (200-400 nm) and a mass selective detector. The purity of each compound in the library, and the mass observed for each compound in the library is listed in Table 5, below. Table 6 lists the purity data alone.

TABLE 5

Characterization of library members.

| | | Mw | | | | | | | | | | | |
|---|---|---|---|---|---|---|---|---|---|---|---|---|---|
| | | 151.21 | 137.18 | 167.21 | 153.18 | 137.18 | 167.21 | 153.18 | 121.18 | 181.23 | 167.21 | 151.21 | |
| | | 8 | 12 | 11 | 15 | 17 | 9 | 13 | 16 | 10 | 14 | 18 | |
| 148.16 | A | 96 | 49 | 74 | 86 | 84 | 78 | 96 | 96 | 92 | 20.0 | 95 | LC/MS purity |
| | | 282 | 267.9 | 297.8 | 283.9 | 268.1 | 297.8 | 283.9 | 252.1 | 311.8 | 297.9 | 282.1 | M + 1 |
| | | | | | | | | 266 | | 280 | 280.0 | | M-17 or M-31 |
| | | 275 | 220 | 225 | 275 | 220 | 225 | 275 | 270 | 275 | 220 | 275 | UV |
| | | | 275 | 275 | | 275 | 275 | | | | 275 | | |
| 164.16 | B | 45.0 | 87 | 70 | 87 | 91 | 95 | 92 | 86.7 | 96 | 87 | 99 | LC/MS purity |
| | | 297.9 | 283.9 | 313.8 | 299.8 | 284.1 | 313.8 | 299.8 | 268 | 327 | 313.8 | 298 | M + 1 |
| | | | | 282.1 | 282 | | 282.1 | 282.1 | | | 296 | | M-17 or M-31 |
| | | 240 | 240 | 240 | 240 | 240 | 240 | 240 | 230 | 230 | 225 | 225 | UV |
| | | 295 | 295 | 295 | 295 | 290 | 295 | 295 | 295 | 295 | 295 | 290 | |
| | | | | | | | | | 300 | | | | |
| 180.16 | C | 97 | 92 | 78 | 88 | 94 | 91 | 87 | 97.5 | 94 | 92 | 98 | LC/MS purity |
| | | 314 | 299.9 | 329.8 | 315.8 | 300.1 | 329.8 | 315.8 | 284.1 | 343.8 | 329.8 | 314.1 | M + 1 |
| | | 282.1 | 282.1 | 298 | | | 298 | 298 | | | | | M-17 or M-31 |
| | | 245 | 245 | 245 | 245 | 245 | 245 | 245 | 240 | 230 | 230 | 235 | UV |
| | | 295 | 295 | 295 | 295 | 295 | 295 | 295 | 295 | 295 | 295 | 295 | |
| | | 320 | 320 | 320 | 320 | 320 | 320 | 320 | 320 | 320 | 320 | 320 | |

TABLE 5-continued

Characterization of library members.

| | | Mw | | | | | | | | | | | |
|---|---|---|---|---|---|---|---|---|---|---|---|---|---|
| | | 151.21 8 | 137.18 12 | 167.21 11 | 153.18 15 | 137.18 17 | 167.21 9 | 153.18 13 | 121.18 16 | 181.23 10 | 167.21 14 | 151.21 18 | |
| 194.18 | D | 59 | 94 | 76 | 94 | 93 | 94 | 95 | 95.7 | 83 | 94 | 97 | LC/MS purity |
| | | 327.4 | 313.9 | 343.8 | 329.8 | 314.1 | 343.8 | 329.8 | 298.1 | 357.8 | 343.8 | 328.1 | M + 1 |
| | | | 296.1 | 312 | 312.1 | | 312 | 312.1 | | | 326.7 | | M-17 or M-31 |
| | | 235 | 245 | 245 | 245 | 245 | 245 | 245 | 235 | 230 | 230 | 230 | UV |
| | | 295 | 295 | 295 | 295 | 295 | 295 | 295 | 295 | 295 | 295 | 295 | |
| | | 320 | 320 | 320 | 320 | 320 | 320 | 320 | 315 | 320 | 320 | 320 | |
| 194.18 | E | 87 | 82 | 93 | 81 | 79 | 85 | 85 | 70.6 | 86 | 64 | 82 | LC/MS purity |
| | | 328 | 314 | 343.9 | 329.9 | 314.1 | 343.9 | 329.9 | 298.1 | 357 | 326 | 328 | M + 1 |
| | | | 296.1 | 312 | 312.1 | | 312.1 | | | | 310.1 | | M-17 or M-31 |
| | | 240 | 245 | 245 | 245 | 245 | 245 | 245 | 240 | 230 | 240 | 225 | UV |
| | | 295 | 295 | 295 | 290 | 290 | 295 | 295 | 290 | 290 | 280 | 290 | |
| | | 320 | 320 | 320 | 320 | 320 | 320 | 320 | 320 | 320 | 320 | 320 | |
| 238.24 | F | 50 | 77 | 79 | 86 | 94.2 | 89 | 84 | 70.1 | 31 | 63 | 61 | LC/MS purity |
| | | 372 | 357.9 | 387.8 | 373.8 | 358 | 387.8 | 373.8 | 342 | 401.9 | 387.8 | 372 | M + 1 |
| | | | | | 536.1 | | | 356 | | 370 | 370 | | M-17 or M-31 |
| | | 245 | 230 | 230 | 240 | 230 | 235 | 240 | 225 | 225 | 230 | 240 | UV |
| | | 295 | 300 | 300 | 300 | 300 | 300 | 300 | 275 | 275 | 300 | 300 | |
| 224.21 | G | 64 | 94 | 79 | 91 | 91 | 93 | 87 | 95 | 92 | 93 | 94 | LC/MS purity |
| | | 358 | 343.9 | 373.9 | 359.8 | 344 | 373.9 | 359.8 | 328 | 387.8 | 373.8 | 358.1 | M + 1 |
| | | | 326.1 | 342.1 | 342 | | 342 | | | | 356 | | M-17 or M-31 |
| | | 240 | 245 | 245 | 245 | 245 | 245 | 245 | 240 | 240 | 240 | 235 | UV |
| | | 320 | 320 | 320 | 320 | 320 | 320 | 320 | 320 | 320 | 320 | 320 | |
| 178.18 | H | 92 | 87 | 76 | 81 | 74 | 87 | 96 | 90 | 91 | 10 | 82 | LC/MS purity |
| | | 311.9 | 297.9 | 327.8 | 313.8 | 298 | 327.8 | 313.8 | 282.1 | 341.8 | 327.8 | 312.1 | M + 1 |
| | | | | | 296 | | | | | 310 | 310.0 | | M-17 or M-31 |
| | | 240 | 230 | 230 | 275 | 225 | 230 | 240 | 275 | 275 | 275 | 275 | UV |
| | | 275 | 275 | 275 | | 275 | 275 | 275 | | | | | |

TABLE 6

Percentage purity of the library members as assessed by LC-MS.

| | | Mw | | | | | | | | | | |
|---|---|---|---|---|---|---|---|---|---|---|---|---|
| | | 151.21 8 | 137.18 12 | 167.21 11 | 153.18 15 | 137.18 17 | 167.21 9 | 153.18 13 | 121.18 16 | 181.23 10 | 167.21 14 | 151.21 18 |
| 148.16 | A | 96.0 | 49.0 | 74.0 | 86.0 | 84.0 | 78.0 | 96.0 | 96.0 | 92.0 | 20.0 | 95.0 |
| 164.16 | B | 45.0 | 87.0 | 70.0 | 87.0 | 91.0 | 95.0 | 92.0 | 86.7 | 96.0 | 87.0 | 99.0 |
| 180.16 | C | 97.0 | 92.0 | 78.0 | 88.0 | 94.0 | 91.0 | 87.0 | 97.5 | 94.0 | 92.0 | 98.0 |
| 194.18 | D | 59.0 | 94.0 | 76.0 | 94.0 | 93.0 | 94.0 | 95.0 | 95.7 | 83.0 | 94.0 | 97.0 |
| 194.18 | E | 87.0 | 82.0 | 93.0 | 81.0 | 79.0 | 85.0 | 85.0 | 70.6 | 86.0 | 64.0 | 82.0 |
| 238.24 | F | 50.0 | 77.0 | 79.0 | 86.0 | 94.2 | 89.0 | 84.0 | 70.1 | 31.0 | 63.0 | 61.0 |
| 224.21 | G | 64.0 | 94.0 | 79.0 | 91.0 | 91.0 | 93.0 | 87.0 | 95.0 | 92.0 | 93.0 | 94.0 |
| 178.18 | H | 92.0 | 87.0 | 76.0 | 81.0 | 74.0 | 87.0 | 96.0 | 90.0 | 91.0 | 10.0 | 82.0 |

Apparatus for Parallel Synthesis

Use of Loading Plate, 96 deep-well plate with tubes, and Lid: The Loading Plate was used to deliver a defined amount of beads to each well of the deep-well synthesis tubes. The PS-CDI beads were poured over the Loading Plate, the excess was scrapped off, and the holes were then aligned with the holes of the 96-deep-well plate with tubes. Simple inversion (followed by gentle tapping) delivered the beads into the wells. After loading the appropriate acids and amines, the Lid was placed onto the tubes and the entire apparatus was connected to an overhead stirrer for rotation. The devices for parallel synthesis were constructed in the machine shop housed in the School of Chemical Sciences, at the University of Illinois, Urbana-Champaign. See FIGS. 4A, 4B, and 4C.

Figure 4A:
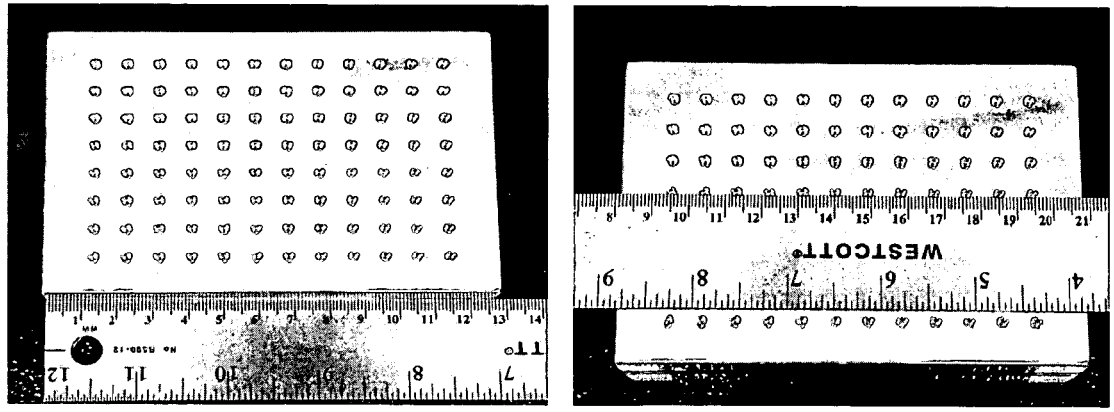
FIG. 4 illustrates various apparatus for parallel synthesis of a combinatorial library.

1. Loading Plate. made in the 96 well format from aluminum, each well (3×6 mm) delivers 10.8-11.3 mg of PS-CDI beads. FIG. 4A.

Figure 4B:
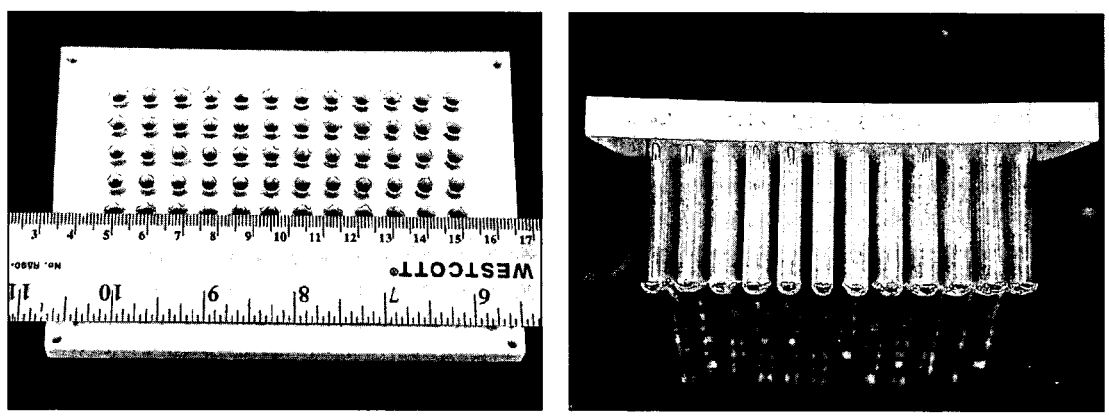

2. Positioning plate and 96 deep-well plate: made in the 96 well format from Teflon, holes 4.95 mm diameter, accommodates 6×50 mm glass inserts, Fisher Scientific #14958-A, volume 1 ml). FIG. 4B.

Figure 4C:
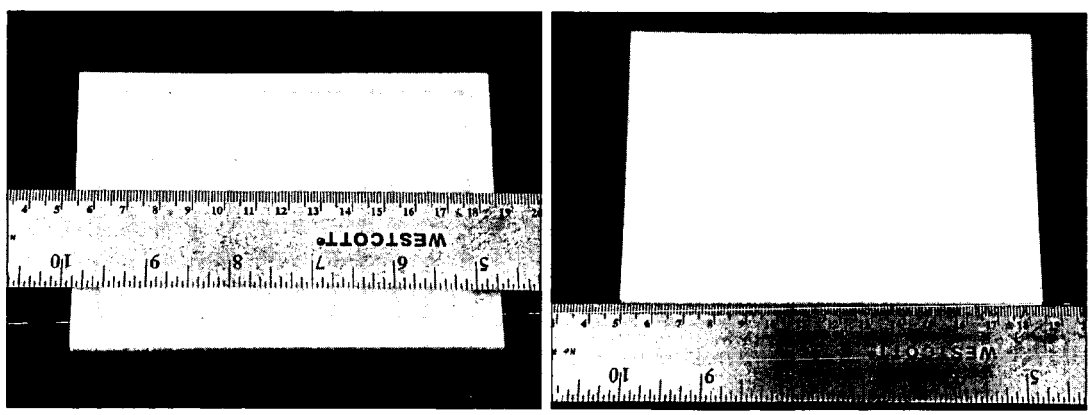
Figure 5A:
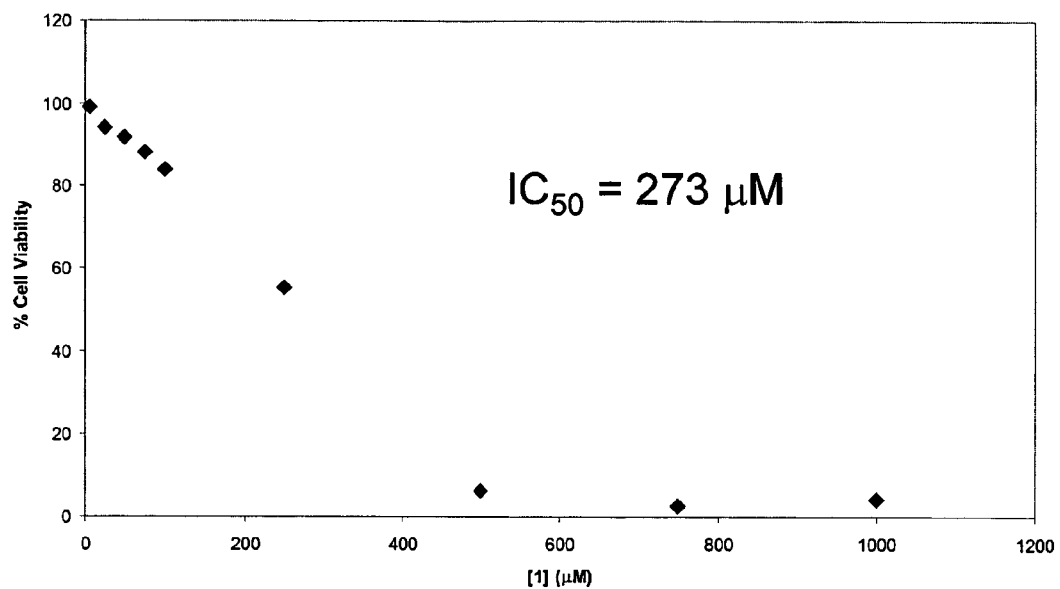
FIG. 5A illustrates a graph of percent cell viability versus concentration of compound 1 with a calculated $IC_{50}$ value.
Figure 5B:
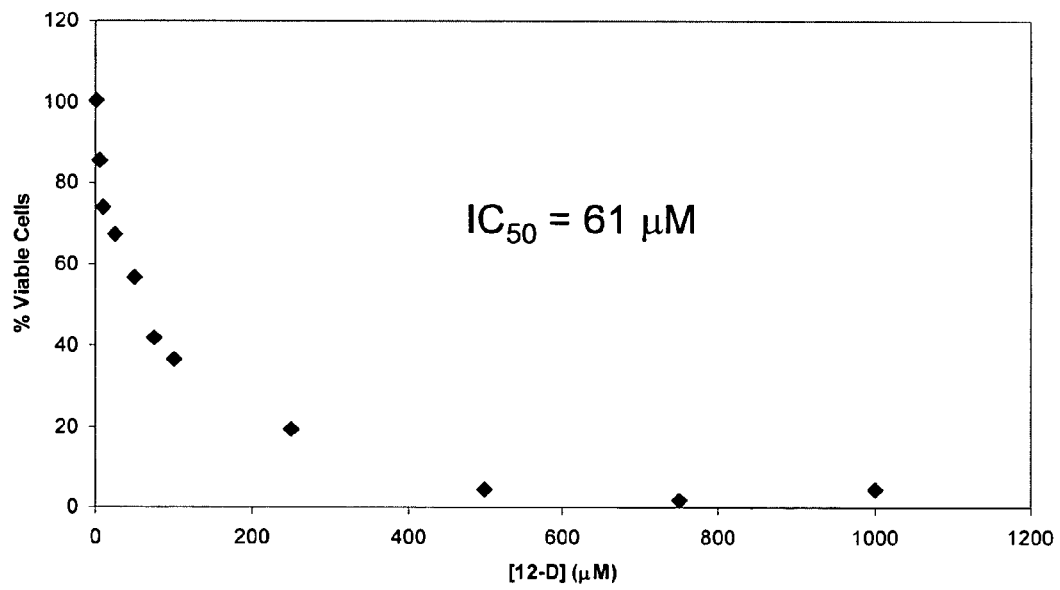
FIG. 5B illustrates a graph of percent viable cells versus concentration of compound 12-D with a calculated $IC_{50}$ value.
Figure 5C:
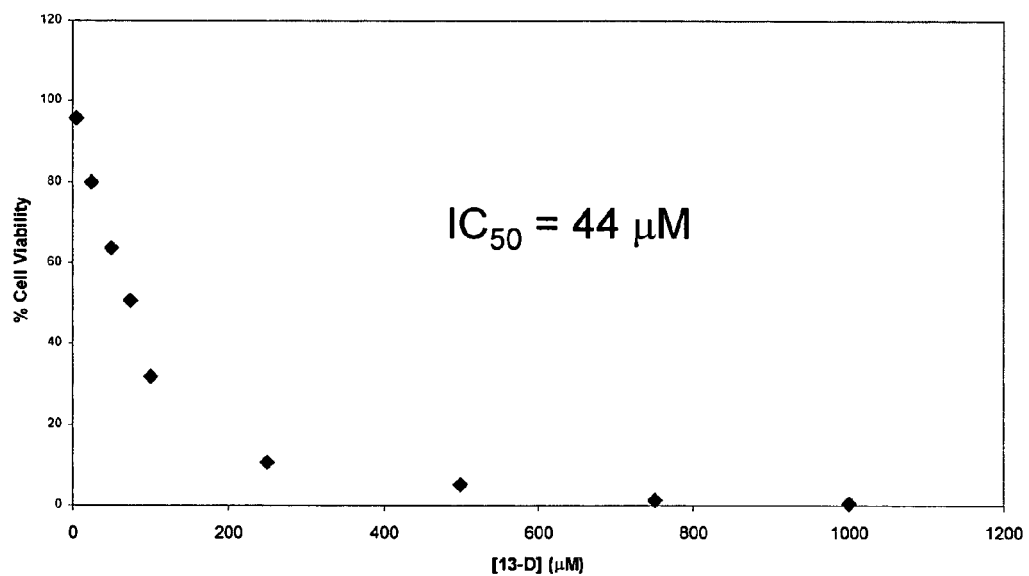
FIG. 5C illustrates a graph of percent viable cells versus concentration of compound 13-D with a calculated $IC_{50}$ value.
Figure 5D:
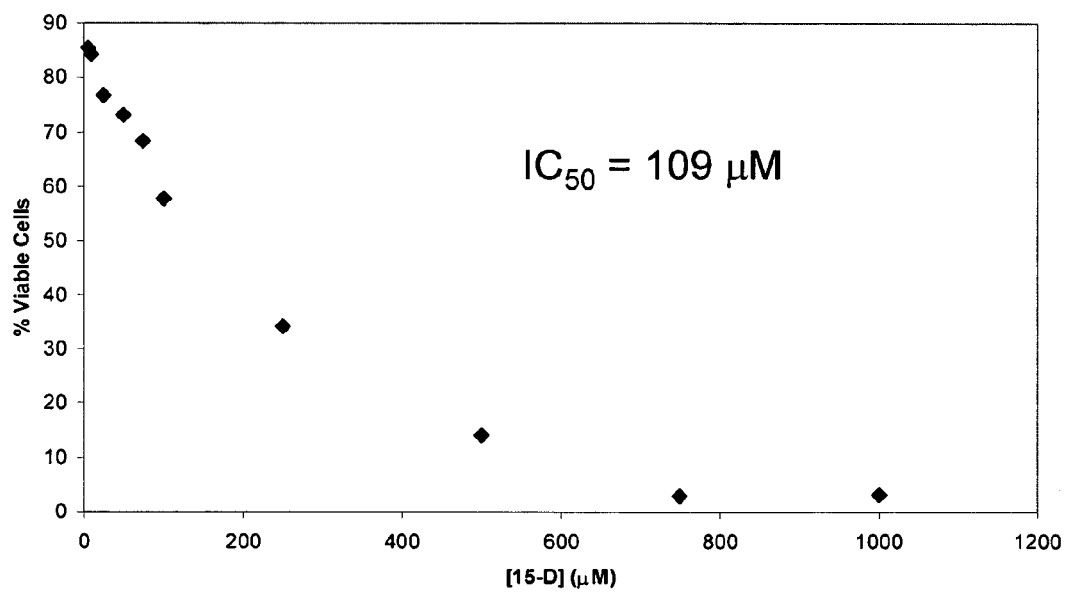
FIG. 5D illustrates a graph of percent viable cells versus concentration of compound 15-D with a calculated $IC_{50}$ value.

3. Lid: made in the 96 well format from Teflon, allows tightly seal the glass inserts to assure no leaking from the insert. FIG. 4C.

Protocols for Biological Assays

General Cell Culture Conditions: U-937 and HL-60 cell lines were grown in RPMI 1640 supplemented with 10% FBS and incubated at 37° C. in a 5% $CO_2$, 95% air atmosphere and were split every two to three days as necessary.

According to the American Type Culture Collection (ATCC), U-937 is a human cell line of histiocytic lymphoma tissue with monocyte morphology. See Sundstrom C, Nilsson K, Int. J. Cancer 17: 565-577, 1976. Also according to ATCC, HL-60 is a human cell line of a tissue type described as peripheral blood, promyeloblast, and acute promyelocytic leukemia, with myeloblastic morphology. See Gallagher R, et al., Blood 54: 713-733, 1979.

High-throughput Cell Death Assay on Library Members: U-937 and HL-60 cells from cell culture were harvested by centrifugation at 250×g for 5 min. Cells were then resuspended in RPMI 1640+10% FBS, counted using a hemocytometer and diluted so that 20,000 cells were seeded into each well of a Corning 96-well flat bottom microtiter plate (Fisher, Chicago Ill.). Media was then added to bring the total volume of each well to 100 µL. Test compounds were transferred into the wells using a 96-pin transfer apparatus (V & P Scientific, San Diego Calif.) that transfers 0.2 µL of compound. The compounds were made up as 50 mM stock solutions in 100% EtOH, so one transfer gave a final concentration of 100 µM. Controls were performed in which only EtOH (containing no compound) was pin-transferred into wells containing cells. The cells were incubated with the compounds for 24 hours, and then cell death was quantitated. This quantitation was performed by addition of 20 µL of the MTS/PMS CellTiter 96 Cell Proliferation Assay reagent (Promega, Madison Wis.) to each well; this reagent is 3-(4,5-dimethylthiazol-2-yl)-5-(3-carboxymethoxyphenyl)-2-(4-sulfophenyl)-2H-tetrazolium, inner salt (MTS), iphenazine methosulfate (PMS).

The plates were incubated at 37° C. for approximately one hour until the colored product formed and the absorbance was then measured at 490 nm in a Spectra Max Plus 384 plate reader (Molecular Devices, Sunnyvale Calif.).

Determination of IC50 Values for 1, 12-D, 13-D, and 15-D. U-937 and HL-60 cells from cell culture were harvested by centrifugation at 250×g for 5 min. Cells were then resuspended in RPMI 1640+10% FBS, counted using a hemocytometer and diluted so that 10,000 cells were seeded in to each well of a Corning 96-well flat bottom microtiter plate (Fisher, Chicago Ill.). Media was then added to bring the total volume of each well to 100 µL. Each compound was weighed and then diluted with EtOH to make a 100 mM stock solution. The compounds were added at 9 or more different concentration in 1 µL of EtOH. After a 72 h incubation (37° C. in a 5% $CO_2$, 95% air atmosphere) cell death was quantitated by addition of 20 µL of the MTS/PMS CellTiter 96 Cell Proliferation Assay reagent (Promega, Madison Wis.) to each well. The plates were incubated at 37° C. for approximately 1 hour until the colored product formed and the absorbance was then measured at 490 nm in a Spectra Max Plus 384 plate reader (Molecular Devices, Sunnyvale Calif.). The $IC_{50}$ was taken as the concentration that caused 50% cell death. The graphs used to determine the $IC_{50}$ values are below in FIGS. 5A, 5B, 5C, and 5D.

Caspase-3 Activity Assay: The amount of caspase-3 like protease activity was determined by the amount of Ac-DEVD-pNA (N-acetyl-Asp-Glu-Val-Asp p-nitroanilide) cleaved per minute by cell lysates. To accomplish this, 100 µM of 13-D was added to cell culture flasks containing 50 mL of $10 \times 10^6$ U-937 cells/mL at 72, 48, 36, 24, 12 and 0 hours before harvesting. Cells were harvested by centrifugation, counted and diluted with RPMI 1640 media to a concentration of $4 \times 10^6$ cells/mL. 100 µL of the diluted cells were added to the wells of a 96-well plate in quadruplicate. The plate was then spun at 1000×g for 5 minutes to pellet the cells. The cells were washed with 100 µL of PBS (137 mM NaCl, 2.7 mM KCl, 4.3 mM $Na_2HPO_4$, 1.4 mM $KH_2PO_4$, pH 7.4) and resuspended in 150 µL of ice cold Caspase Assay Buffer (50 mM HEPES, 100 mM NaCl, 10 mM DTT, 0.1 mM EDTA, 0.1% CHAPS and 10% Glycerol, pH 7.4). Each well was then sonicated to lyse the cells. 90 µL of cell lysate was transferred from each well into a new plate. Caspase Assay Buffer was added to wells as a control. Ac-DEVD-pNA (Sigma, St. Louis Mo.) was added into each well to give a final concentration of 200 µM. The plate was then read every 2 minutes at 405 nm for 2 hours in a Spectra Max Plus 384 plate reader (Molecular Devices, Sunnyvale Calif.). The slope of the linear portion for each compound was then determined and any cleavage of the substrate in the control wells was subtracted out. The amount of Ac-DEVD-pNA cleaved in pmol/min was then calculated and plotted.

Analysis of Mitochondria Depolarization by Flow Cytometry: The depolarization of the mitochondrial membrane was measured by the fluorescence emitted by the JC-9 dye (Molecular Probes, Eugene Oreg.). 100 µM of 13-D or 10 µM etoposide in 1 µL of EtOH were added to cell culture flasks containing 50 mL of $10 \times 10^6$ U-937 cells/mL. After growth for 72 hours (37° C. in a 5% $CO_2$, 95% air atmosphere) the cells were harvested by centrifugation, counted, and diluted to $1 \times 10^6$ cells/mL in RPMI 1640 media. 10 µg of the JC-9 dye was added to $1 \times 10^6$ cells in 1 mL and incubated at room temperature for 10 min. Cells were washed twice with PBS and resuspended in a final volume of 500 µL PBS. The fluorescence intensity of each cell was determined by flow cytometry at 525 nm (channel 1 green) and 675 nm (channel 4 red). 50,000 cells were analyzed in each experiment. The data was then analyzed using Summit Software (Cytomation, Fort Collins Colo.) and the number of cells within the upper left region, viable cells, was determined.

Splenocyte Toxicity Assay: Splenocytes were isolated from the spleen of a 7-month old male C57Black/6 mouse and suspended in 1 mL RPMI 1640+10% FBS+2.5 µg/mL concanavalin A. These cells were counted and diluted so that $2.5 \times 10^5$ cells were seeded in to each well containing a total of 200 µL of media. Various concentrations of compound 13-D in 1 µL of EtOH were added and the plates were then incubated at 37° C. in a 5% $CO_2$, 95% air atmosphere for 72 hours. 1 µL of EtOH was added to separate control wells. After 72 hours of incubation, 20 µL of the MTS/PMS CellTiter 96 Cell Proliferation Assay reagent (Promega, Madison Wis.) was added to each well. The plates were incubated at 37° C. for approximately two hours until the colored product formed and the absorbance was then measured at 490 nm in a Spectra Max Plus 384 plate reader (Molecular Devices, Sunnyvale Calif.).

T-cell Isolation and Toxicity Assay: Splenocytes were isolated from the spleen of a 3-month old male C57Black/6 mouse and suspended in 1 mL RPMI 1640+10% FBS. Erythrocytes were selectively lysed and the T cells were highly enriched by using a mouse erythrocyte lysing kit and a mouse T cell enrichment column (R & D Systems, Minneapolis Minn.). FITC labeled anti-TCR antibodies were used to determine the purity of T cells in pre- and post-column samples. The T cells were enriched from approximately 35% to 90% of the total cell population (see FIG. 6A, 6B below). The purified T cells were then counted and diluted so that $2.5 \times 10^5$ cells were seeded in to each well of a 96-well plate containing 200 µL of media. These cells were either stimulated to grow (by addition of ConA to a concentration of 2.5 µg/mL) or left untreated. Various concentrations of compound 13-D in 1 µL of EtOH or 1 µL of EtOH as a control were added and the plates were incubated at 37° C. in a 5% $CO_2$, 95% air atmosphere for 72 hours. After the 72 hours of incubation, 200 µL of cells were diluted in 300 µL PBS. Propidium iodide was then added to a concentration of 1 µg/mL. Cells were then incubated at room temperature for 5 minutes and analyzed by flow cytometry. The fluorescene intensity of each cell was determined at 620 nm (channel 3) and at least 50,000 cells were analyzed for each experiment (FIG. 7A, 7B, below). The data was then analyzed using Summit Software (Cytomation, Fort Collins Colo.) and the number of viable cells was determined. Non-concanavalin A stimulated T cells were also treated with 13-D, and viable cells in these samples were determined by PI staining (as above). In both the ConA stimulated and non-stimulated experiments, no difference was observed between 13-D treated and non-treated control cells.

Figure 6A:
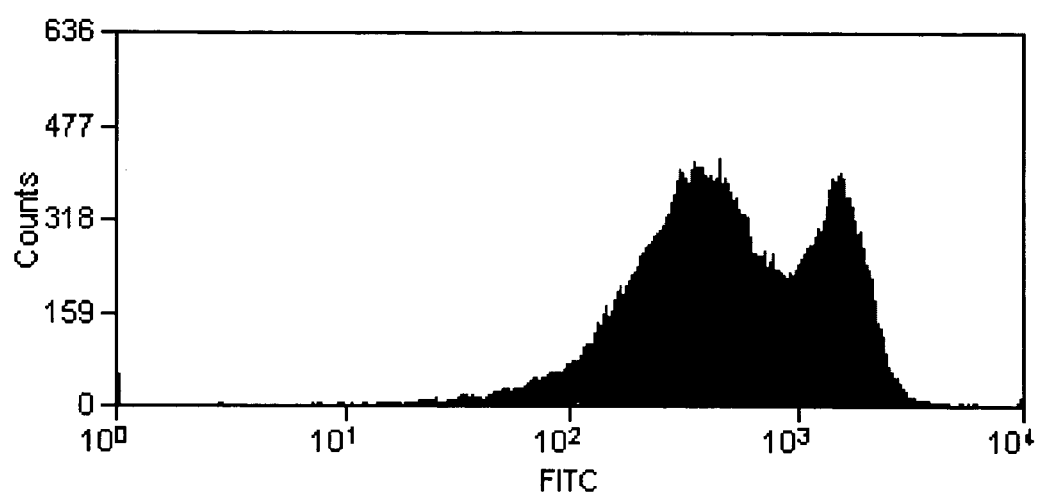
FIG. 6A, pre-enrichment.
Figure 6B:
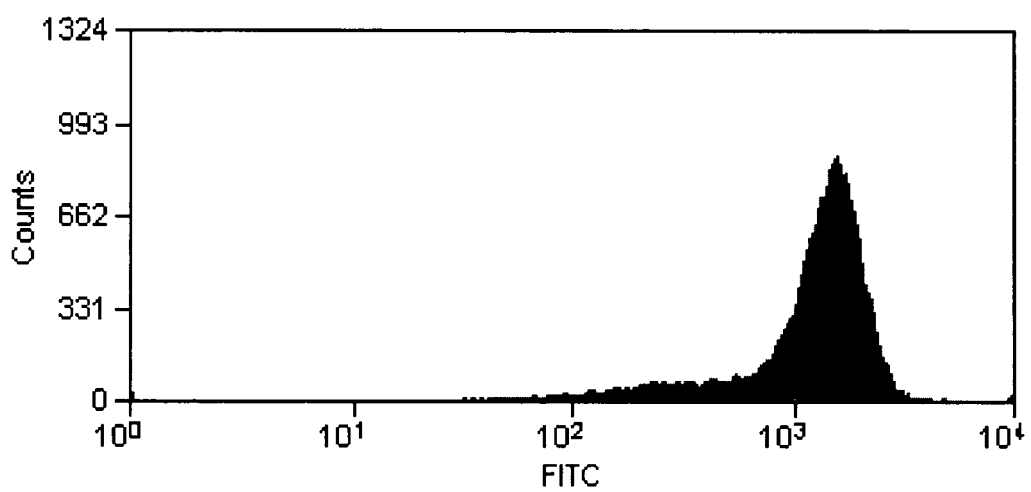
FIG. 6B, post-enrichment.
Figure 7A:
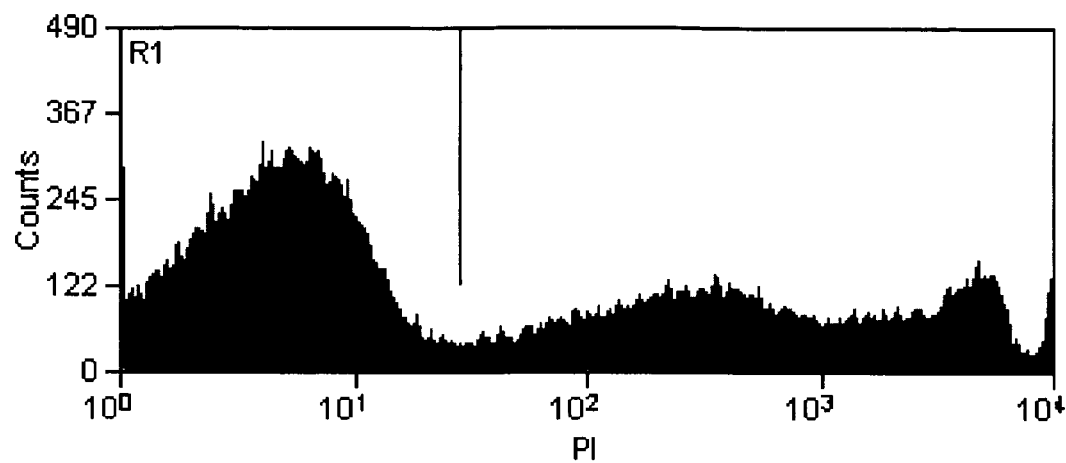
FIG. 7A illustrates flow cytometry data from Concanavalin A stimulated T cells. Region R1 indicates 86.4% viable cells.
Figure 7B:
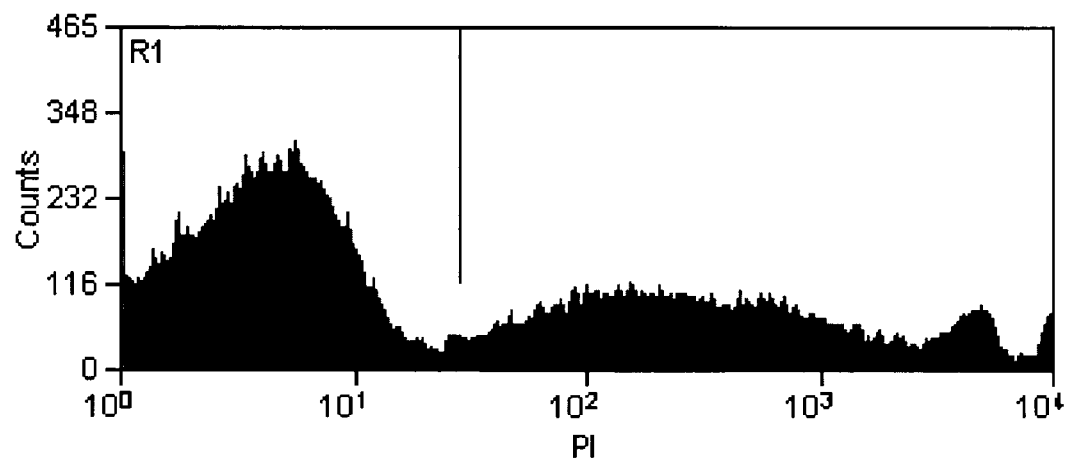
FIG. 7B illustrates data from an experiment using Concanavalin A stimulated T cells with 500 μM of compound 13-D. Region R1 indicates 87.4% viable cells.
Figure 8A:
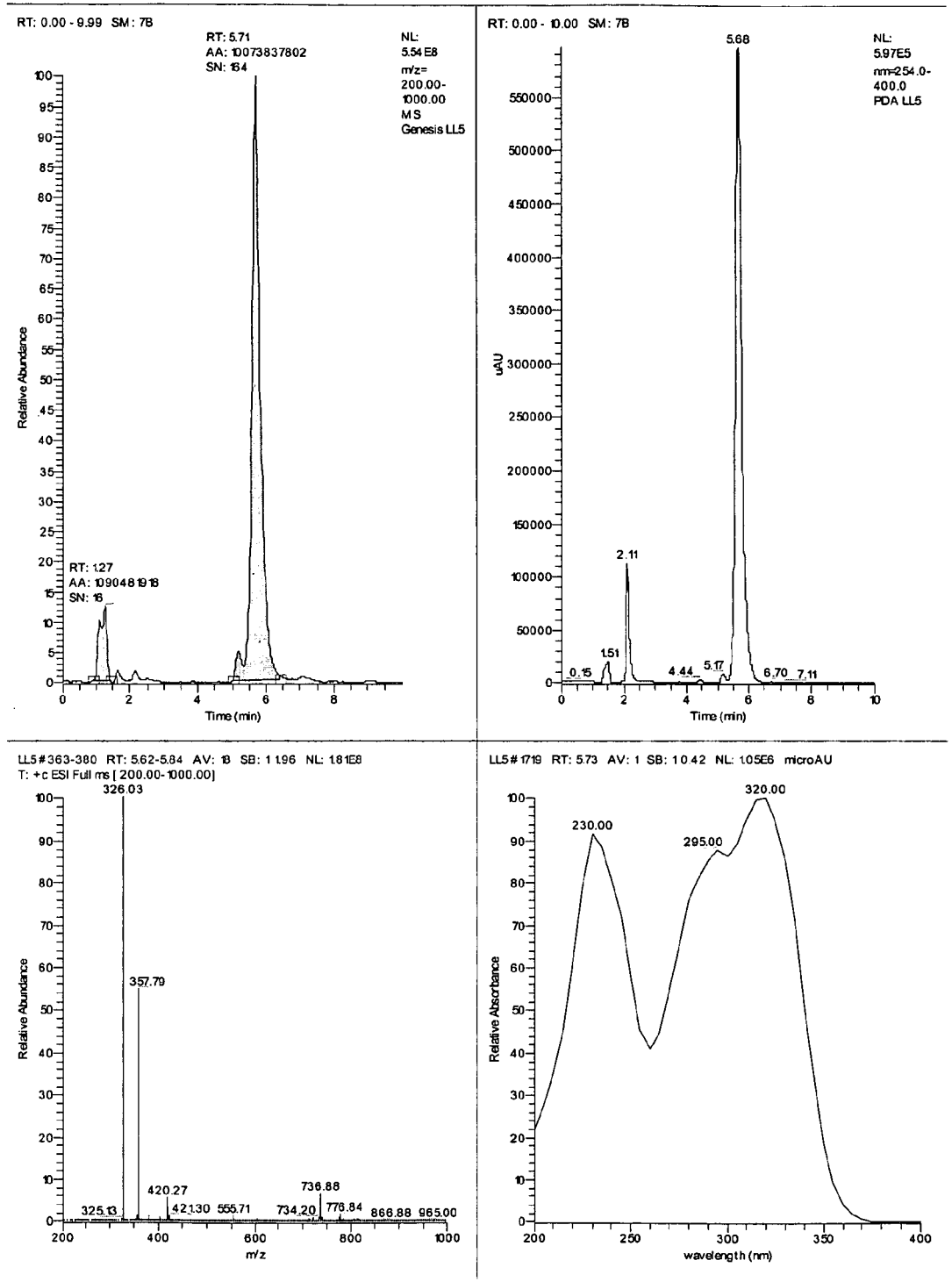
FIG. 8A and FIG. 8B illustrate representative LC/MS analysis of two compounds from the library of Example 1.
Figure 8B:
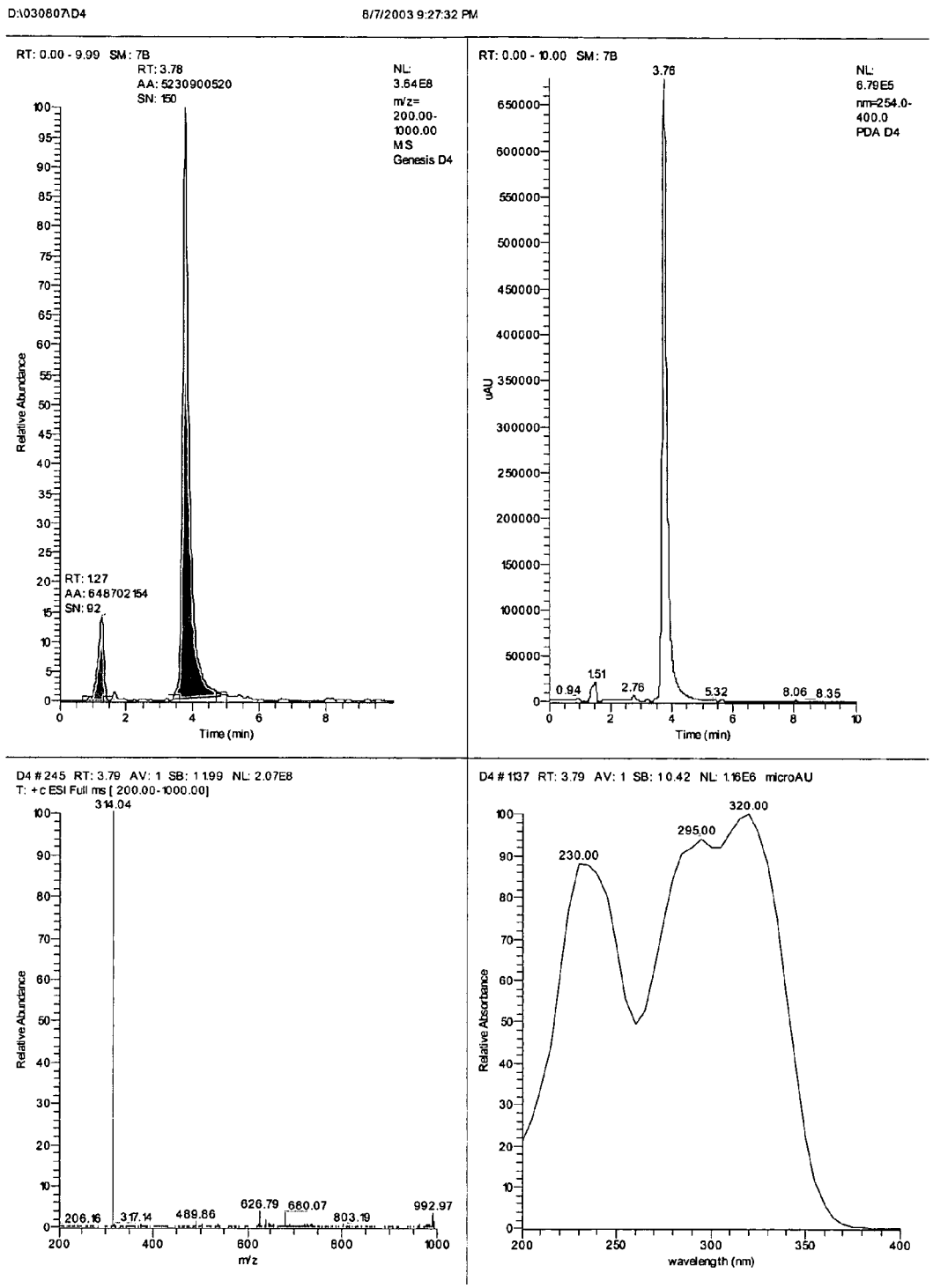

As illustrated in FIGS. 6A and 6B, FITC labeled anti-TCR antibodies were used to determine the purity of T cells before and after purification (Pre-column T cells, FIG. 6A; Post-column T cells, FIG. 6B).

FIG. 7A illustrates flow cytometry data from Concanavalin A stimulated T cells; region R1 indicates 86.4% viable cells. FIG. 7B illustrates data from an experiment using Concanavalin A stimulated T cells with 500 µM of compound 13-D; region R1 indicates 87.4% viable cells. The T-cell population from the mouse splenocytes was purified and stimulated to grow, treated with 500 µM 13-D for 72 h, and stained with propidium iodide. Flow cytometry analysis of the nontreated (with respect to a compound) and treated samples indicated a viable cell population (R1) of 86 and 87%, respectively.

Figure 9B:
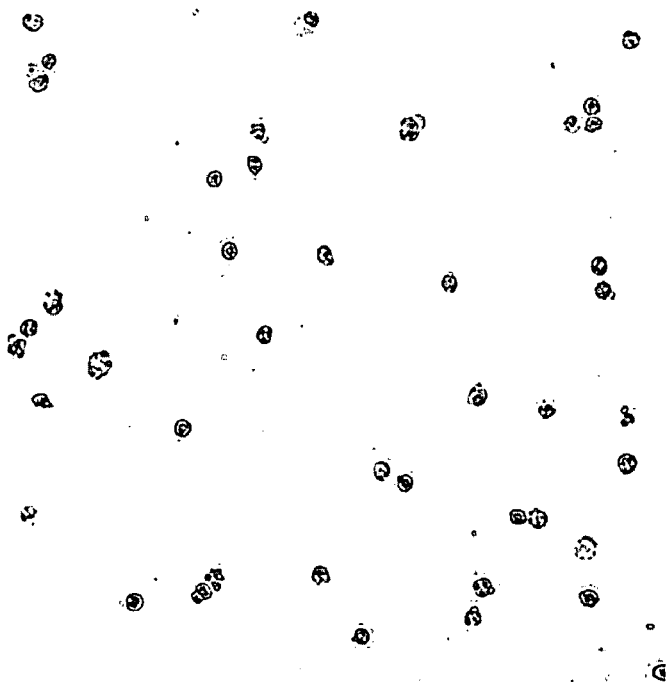
Figure 10A:
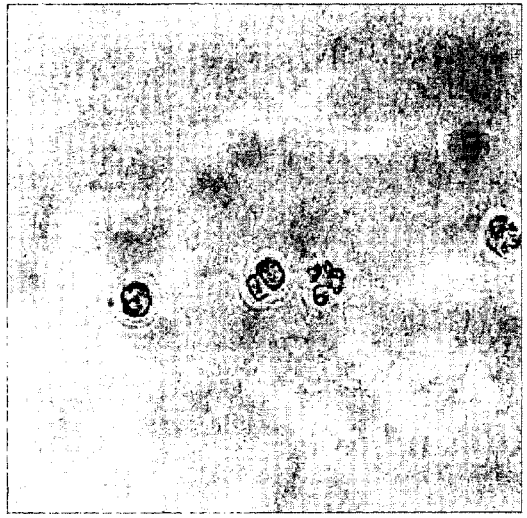
FIG. 10A-FIG. 10C illustrate data from confocal microscopy of U-937 cells cultured in the presence of Compound 13-D; magnification at 400×.
Figure 10B:
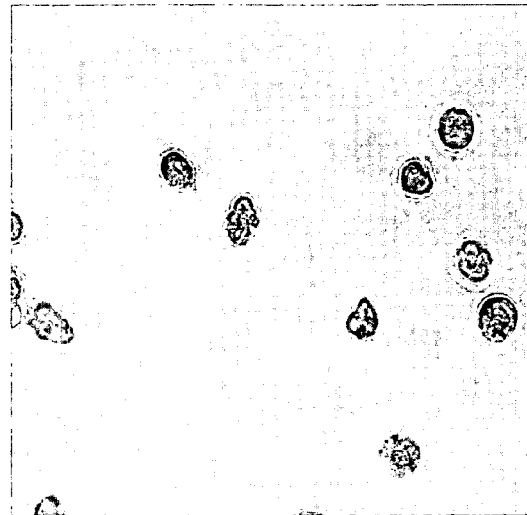
Figure 10C:
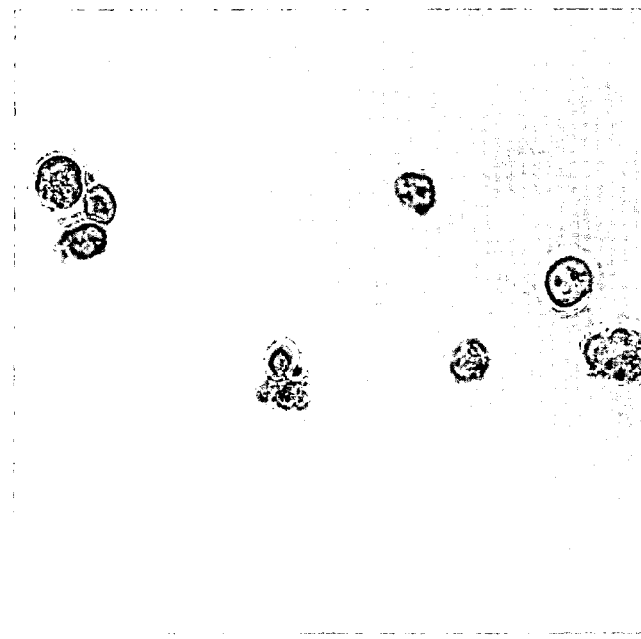
Figure 11:
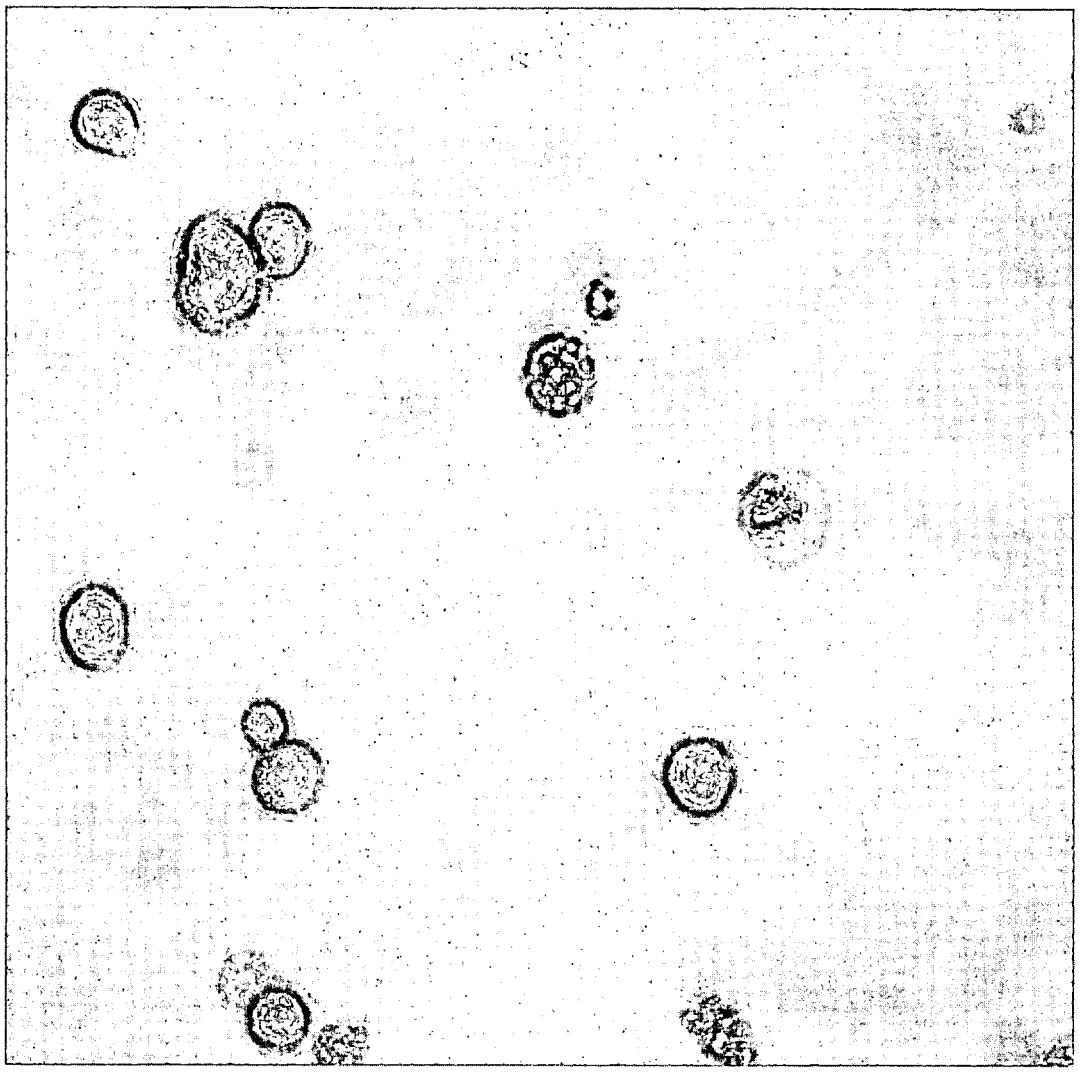
FIG. 11 illustrate data from confocal microscopy of U-937 cells cultured in the presence of Compound 13-D; magnification at 200×.
Figure 12:
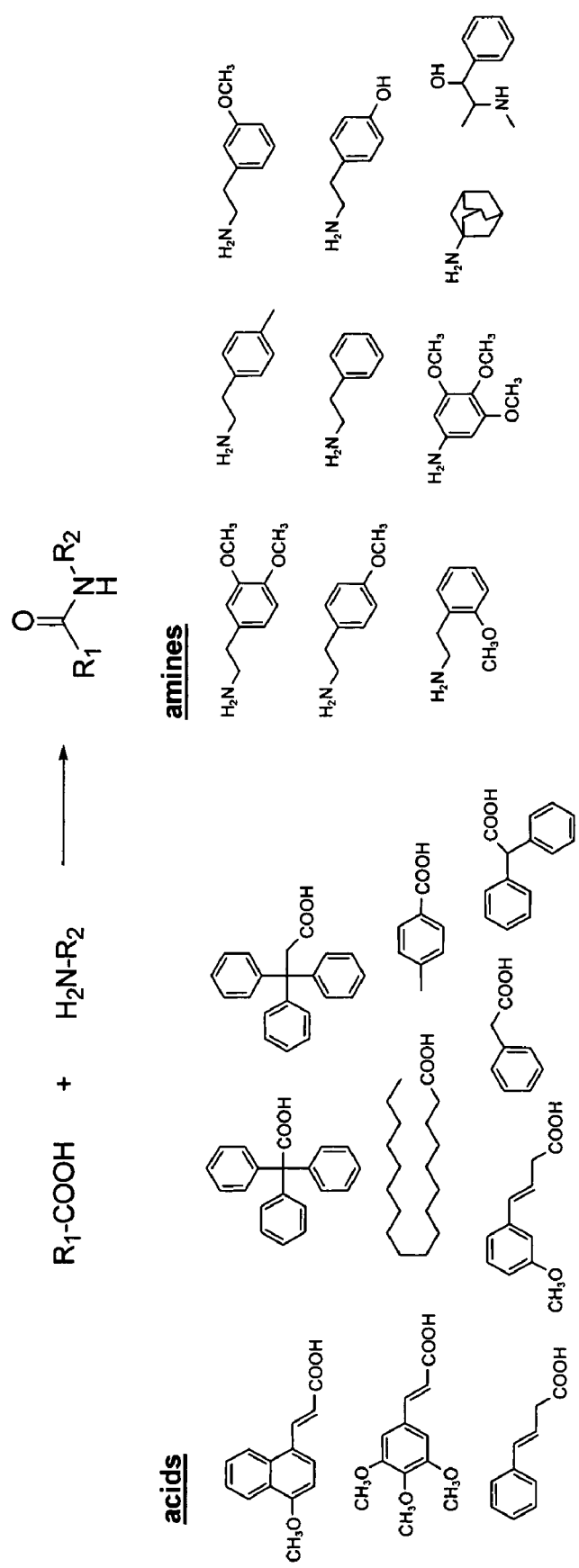
FIG. 12 illustrates a reaction scheme of a generic acid compound with a generic amine compound yielding an amide product. A set of ten acid compounds and ten amine compounds for forming a first generation library are also shown.
Figure 13:
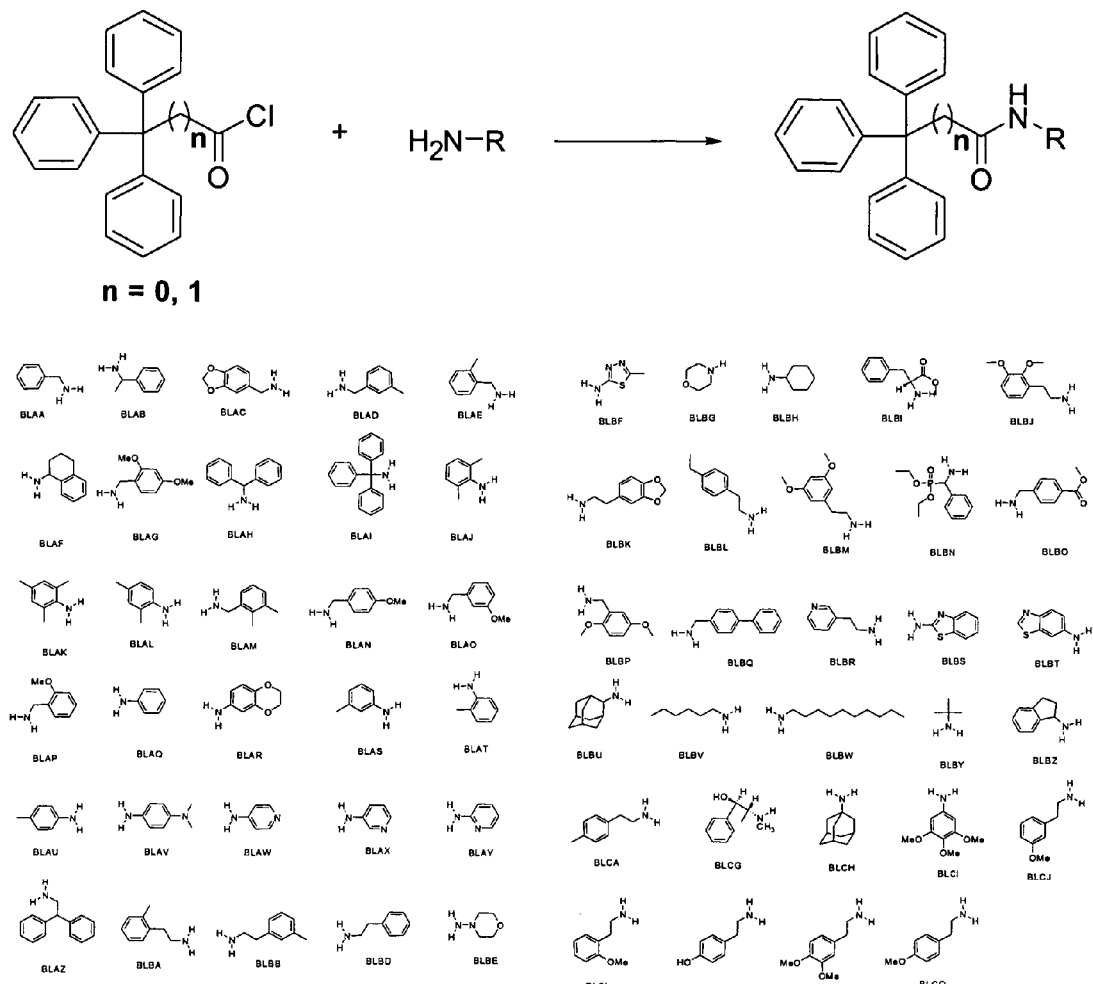
FIG. 13 illustrates a scheme for making a second-generation library of triphenylamides and a set of 59 amine compounds.
Figure 14:
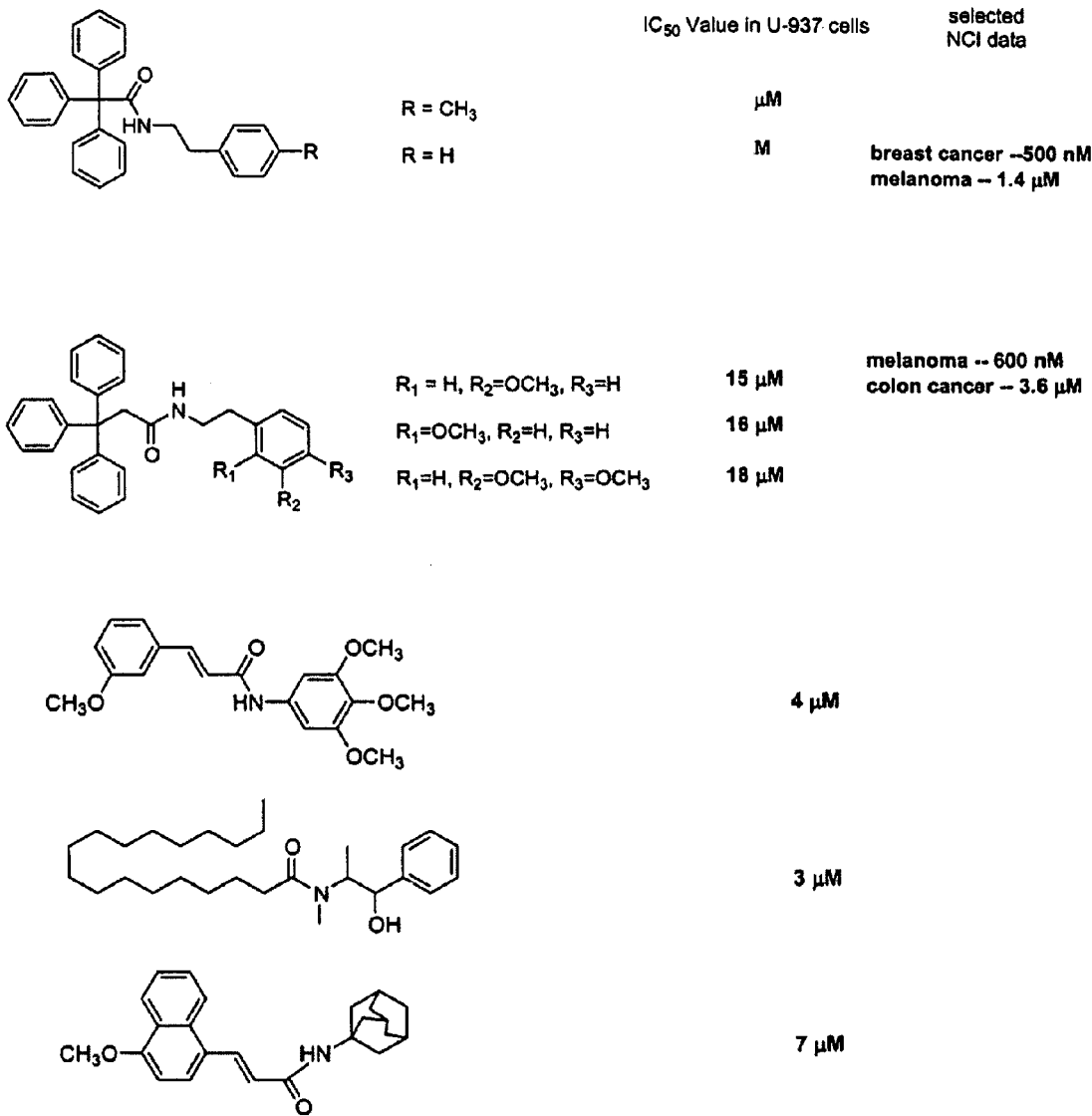
FIG. 14 illustrates a table with five structures corresponding to eight specific compounds and results from screening data using a U-937 cell assay and an assay of the National Cancer Institute drug screen with human cancer cell lines.

Microscopy: U-937 cells from cell culture were harvested by centrifugation at 250×g for 5 minutes. Cells were resuspended in RPMI 1640+10% FBS, counted using a hemocytometer and diluted so that 20,000 cells were seeded in to each well of a 96-well plate. Media was then added to bring the total volume of each well to 100 µL. Compound 13-D was added to make a final concentration of 100 µM. Pictures of the cells were taken at various times using a Carl Zeiss confocal microscope (Carl Zeiss, Thornwood N.Y.). See FIG. 9A. Picture at 100×; FIG. 9B. Picture at 100×; FIG. 10A. Picture at 400×; FIG. 10B. Picture at 400×; FIG. 10C. Picture at 400×; and FIG. 11. Picture at 200×.

Example 3

Synthesis, Identification, and Testing of Small Molecules

In searching for molecules that selectively induce apoptosis in cancer cells, a combinatorial library of compounds was designed whose members would likely be active in apoptotic assays. This library relates to compounds of the formula (Z1) and can relate to other compounds disclosed herein.

We synthesized selected subsets of the library. The carboxylic acids were first converted to their acid chlorides by treatment with thionyl chloride ($SOCl_2$). The acid chlorides thus generated were treated with the amines to form the amide products.

Compounds were tested in a U937 cell assay as previously described by Hergenrother et al. (see Hergenrother 2003 and U.S. 60/516,566).

Selected compounds were identified for additional testing against a panel of human cancer cell lines maintained by the National Cancer Institute. A compound Z2 demonstrated significant activity against breast cancer cells and melanoma cells. A second compound Z3 demonstrated significant activity against melanoma cells and colon cancer cells.

Results of screening for compounds Z2 and Z3 using human cancer cell lines are shown. See Table 7 and Table 8.

TABLE 7

Dose-Response Data for Compound Z2 including GI50, TGI and LC50 values.

| | Time | | Log10 Concentration | | | | | | | | | | | | |
| | | | Mean Optical Densities | | | | | Percent Growth | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.175 | 0.460 | 0.517 | 0.401 | 0.399 | 0.400 | 0.263 | 120 | 79 | 78 | 79 | 31 | 4.00E−05 | >1.00E−04 | >1.00E−04 |
| HL-60(TB) | 0.188 | 1.610 | 1.552 | 1.557 | 1.745 | 1.560 | 0.435 | 96 | 96 | 110 | 96 | 17 | 3.87E−05 | >1.00E−04 | >1.00E−04 |
| K-562 | 0.096 | 1.196 | 1.223 | 1.183 | 1.212 | 0.949 | 0.484 | 103 | 99 | 102 | 78 | 35 | 4.49E−05 | >1.00E−04 | >1.00E−04 |
| MOLT-4 | 0.086 | 0.521 | 0.454 | 0.457 | 0.513 | 0.394 | 0.412 | 85 | 85 | 98 | 71 | 75 | >1.00E−04 | >1.00E−04 | >1.00E−04 |
| RPMI-8226 | 0.243 | 0.956 | 0.989 | 0.957 | 0.940 | 0.679 | 0.284 | 105 | 100 | 98 | 61 | 6 | 1.59E−05 | >1.00E−04 | >1.00E−04 |
| Non-Small Cell Lung Cancer | | | | | | | | | | | | | | | |
| A549/ATCC | 0.370 | 0.884 | 0.804 | 0.773 | 0.751 | 0.278 | 0.262 | 84 | 78 | 74 | −25 | −29 | 1.75E−06 | 5.59E−06 | >1.00E−04 |
| EKVX | 0.410 | 0.723 | 0.709 | 0.720 | 0.719 | 0.472 | 0.304 | 96 | 99 | 99 | 20 | −26 | 4.13E−06 | 2.71E−05 | >1.00E−04 |
| HOP-62 | 0.377 | 0.792 | 0.771 | 0.850 | 0.755 | 0.555 | 0.482 | 95 | 114 | 91 | 43 | 25 | 7.10E−06 | >1.00E−04 | >1.00E−04 |
| HOP-92 | 0.263 | 1.240 | 1.279 | 1.285 | 1.148 | 1.151 | 0.868 | 104 | 105 | 91 | 91 | 62 | >1.00E−04 | >1.00E−04 | >1.00E−04 |
| NCI-H460 | 0.072 | 0.606 | 0.620 | 0.550 | 0.589 | 0.533 | 0.145 | 103 | 89 | 97 | 86 | 14 | 3.15E−05 | >1.00E−04 | >1.00E−04 |
| NCI-H522 | 0.816 | 1.161 | 1.239 | 1.144 | 1.058 | 1.032 | 0.448 | 123 | 95 | 70 | 63 | −45 | 1.31E−05 | 3.81E−05 | >1.00E−04 |
| Colon Cancer | | | | | | | | | | | | | | | |
| COLO 205 | 0.228 | 0.865 | 0.898 | 0.841 | 0.834 | 0.274 | 0.270 | 105 | 96 | 95 | 7 | 7 | 3.26E−06 | >1.00E−04 | >1.00E−04 |
| HCT-116 | 0.272 | 0.715 | 0.641 | 0.633 | 0.569 | 0.308 | 0.275 | 83 | 82 | 67 | 8 | 1 | 1.95E−06 | >1.00E−04 | >1.00E−04 |
| HCT-15 | 0.194 | 0.848 | 0.803 | 0.790 | 0.821 | 0.433 | 0.225 | 93 | 91 | 96 | 36 | 5 | 5.91E−06 | >1.00E−04 | >1.00E−04 |
| KM12 | 0.967 | 1.999 | 2.062 | 2.034 | 1.996 | 0.978 | 0.786 | 106 | 103 | 100 | 1 | −19 | 3.19E−06 | 1.13E−05 | >1.00E−04 |
| SW-620 | 0.127 | 0.571 | 0.567 | 0.566 | 0.537 | 0.242 | 0.137 | 99 | 99 | 92 | 26 | 2 | 4.35E−06 | >1.00E−04 | >1.00E−04 |
| CNS Cancer | | | | | | | | | | | | | | | |
| SF-268 | 0.529 | 1.499 | 1.435 | 1.449 | 1.531 | 1.350 | 0.646 | 93 | 95 | 103 | 85 | 12 | 3.00E−05 | >1.00E−04 | >1.00E−04 |
| SF-295 | 1.003 | 1.729 | 1.747 | 1.712 | 1.620 | 0.978 | 0.716 | 102 | 98 | 85 | −2 | −29 | 2.51E−06 | 9.36E−06 | >1.00E−04 |
| SNB-19 | 0.488 | 1.256 | 1.283 | 1.271 | 1.173 | 0.824 | 0.791 | 104 | 102 | 89 | 44 | 39 | 7.27E−06 | >1.00E−04 | >1.00E−04 |
| SNB-75 | 0.346 | 0.659 | 0.654 | 0.651 | 0.633 | 0.576 | 0.524 | 98 | 98 | 92 | 73 | 57 | >1.00E−04 | >1.00E−04 | >1.00E−04 |
| U251 | 0.342 | 0.906 | 0.965 | 0.870 | 0.857 | 0.358 | 0.246 | 110 | 94 | 91 | 3 | −28 | 2.93E−06 | 1.24E−05 | >1.00E−04 |

TABLE 7-continued

Dose-Response Data for Compound Z2 including GI50, TGI and LC50 values.

| | Time | Mean Optical Densities | | | | | | Percent Growth | | | | | | | |
|---|---|---|---|---|---|---|---|---|---|---|---|---|---|---|---|
| | | | | Log10 Concentration | | | | | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| Melanoma | | | | | | | | | | | | | | | |
| SK-MEL-2 | 0.669 | 1.230 | 1.308 | 1.203 | 1.179 | 0.908 | 0.352 | 114 | 95 | 91 | 43 | −47 | 7.04E−06 | 2.98E−05 | >1.00E−04 |
| SK-MEL-28 | 0.205 | 0.490 | 0.439 | 0.434 | 0.441 | 0.369 | 0.298 | 82 | 80 | 83 | 58 | 32 | 2.01E−05 | >1.00E−04 | >1.00E−04 |
| SK-MEL-5 | 0.585 | 1.341 | 1.549 | 1.506 | 1.500 | 0.937 | 0.033 | 127 | 122 | 121 | 46 | −94 | 8.97E−06 | 2.14E−05 | 4.84−05 |
| UACC-62 | 0.696 | 1.097 | 0.995 | 1.028 | 0.931 | 0.723 | 0.461 | 74 | 83 | 58 | 7 | −34 | 1.45E−06 | 1.46E−05 | >1.00E−04 |
| Ovarian Cancer | | | | | | | | | | | | | | | |
| IGROV1 | 0.318 | 0.543 | 0.618 | 0.506 | 0.477 | 0.565 | 0.254 | 133 | 83 | 70 | 110 | −20 | 2.88E−05 | 7.00E−05 | >1.00E−04 |
| OVCAR-3 | 0.486 | 0.755 | 0.782 | 0.737 | 0.738 | 0.584 | 0.549 | 110 | 93 | 93 | 36 | 23 | 5.78E−06 | >1.00E−04 | >1.00E−04 |
| OVCAR-4 | 0.225 | 0.731 | 0.710 | 0.722 | 0.641 | 0.537 | 0.496 | 96 | 98 | 82 | 62 | 54 | >1.00E−04 | >1.00E−04 | >1.00E−04 |
| OVCAR-5 | 0.389 | 0.712 | 0.839 | 0.692 | 0.670 | 0.468 | 0.349 | 140 | 94 | 87 | 24 | −10 | 3.91E−06 | 5.06E−05 | >1.00E−04 |
| OVCAR-8 | 0.575 | 0.761 | 0.735 | 0.688 | 0.712 | 0.344 | 0.370 | 86 | 61 | 74 | −40 | −36 | 1.62E−06 | 4.44E−06 | >1.00E−04 |
| SK-OV-3 | 0.365 | 0.954 | 0.958 | 0.894 | 0.876 | 0.761 | 0.516 | 101 | 90 | 87 | 67 | 26 | 2.60E−05 | >1.00E−04 | >1.00E−04 |
| Renal Cancer | | | | | | | | | | | | | | | |
| 786-0 | 0.380 | 1.102 | 1.056 | 1.005 | 0.975 | 0.657 | 0.527 | 94 | 87 | 82 | 38 | 20 | 5.43E−06 | >1.00E−04 | >1.00E−04 |
| ACHN | 0.377 | 0.677 | 0.681 | 0.654 | 0.683 | 0.366 | 0.207 | 101 | 92 | 102 | −3 | −45 | 3.13E−06 | 9.35E−06 | >1.00E−04 |
| CAKI-1 | 0.799 | 1.286 | 1.345 | 1.319 | 1.302 | 0.883 | 0.606 | 112 | 107 | 103 | 17 | −24 | 4.16E−06 | 2.61E−05 | >1.00E−04 |
| SN12C | 0.435 | 0.546 | 0.501 | 0.516 | 0.518 | 0.341 | 0.197 | 59 | 73 | 75 | −22 | −55 | 1.80E−06 | 5.96E−06 | 7.16E−05 |
| TK-10 | 1.040 | 1.259 | 1.186 | 1.230 | 1.191 | 1.021 | 0.718 | 67 | 87 | 69 | −2 | −31 | 1.86E−06 | 9.42E−06 | >1.00E−04 |
| UO-31 | 0.623 | 1.542 | 1.549 | 1.518 | 1.507 | 0.977 | 0.487 | 101 | 97 | 96 | 39 | −22 | 6.32E−06 | 4.34E−05 | >1.00E−04 |
| Prostate Cancer | | | | | | | | | | | | | | | |
| PC-3 | 0.355 | 1.082 | 1.078 | 1.099 | 1.064 | 0.979 | 0.449 | 99 | 102 | 97 | 86 | 13 | 3.10E−05 | >1.00E−04 | >1.00E−04 |
| DU-145 | 0.232 | 0.542 | 0.493 | 0.498 | 0.472 | 0.311 | 0.200 | 84 | 86 | 77 | 26 | −14 | 3.38E−06 | 4.42E−05 | >1.00E−04 |
| Breast Cancer | | | | | | | | | | | | | | | |
| MCF7 | 0.115 | 0.537 | 0.550 | 0.531 | 0.571 | 0.445 | 0.159 | 103 | 99 | 108 | 78 | 10 | 2.60E−05 | >1.00E−04 | >1.00E−04 |
| NCI/ADR-RES | 0.267 | 0.477 | 0.469 | 0.470 | 0.450 | 0.216 | 0.227 | 96 | 97 | 87 | −19 | −15 | 2.23E−06 | 6.59E−06 | >1.00E−04 |
| MDA-MB-231/ATCC | 0.591 | 0.829 | 0.770 | 0.811 | 0.670 | 0.474 | 0.377 | 75 | 93 | 33 | −20 | −36 | 5.19E−07 | 4.21E−06 | >1.00E−04 |
| HS 578T | 0.604 | 0.848 | 0.875 | 0.865 | 0.850 | 0.640 | 0.457 | 111 | 107 | 101 | 15 | −24 | 3.88E−06 | 2.37E−05 | >1.00E−04 |
| MDA-MB-435 | 1.095 | 1.843 | 1.887 | 1.827 | 1.793 | 1.525 | 0.773 | 106 | 98 | 93 | 57 | −29 | 1.22E−05 | 4.58E−05 | >1.00E−04 |
| BT-549 | 0.294 | 0.570 | 0.546 | 0.557 | 0.571 | 0.393 | 0.238 | 91 | 95 | 100 | 36 | −19 | 5.99E−06 | 4.49E−05 | >1.00E−04 |
| T-47D | 0.393 | 0.677 | 0.665 | 0.631 | 0.607 | 0.546 | 0.524 | 96 | 84 | 75 | 54 | 46 | 3.04E−05 | >1.00E−04 | >1.00E−04 |

TABLE 8

Dose-Response Data for Compound Z3 including GI50, TGI and LC50 values.

| | Time | Mean Optical Densities | | | | | | Percent Growth | | | | | | | |
|---|---|---|---|---|---|---|---|---|---|---|---|---|---|---|---|
| | | | | Log10 Concentration | | | | | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.175 | 0.460 | 0.353 | 0.443 | 0.385 | 0.311 | 0.272 | 62 | 94 | 74 | 48 | 34 | 8.16E−06 | >1.00E−04 | >1.00E−04 |
| HL-60 (TB) | 0.188 | 1.610 | 1.598 | 1.735 | 1.720 | 0.935 | 0.785 | 99 | 109 | 108 | 53 | 42 | 1.75E−05 | >1.00E−04 | >1.00E−04 |
| K-562 | 0.096 | 1.196 | 1.213 | 1.195 | 1.198 | 0.491 | 0.445 | 102 | 100 | 100 | 36 | 32 | 6.03E−06 | >1.00E−04 | >1.00E−04 |
| MOLT-4 | 0.086 | 0.521 | 0.588 | 0.623 | 0.551 | 0.233 | 0.229 | 116 | 123 | 107 | 34 | 33 | 6.01E−06 | >1.00E−04 | >1.00E−04 |
| RPMI-8226 | 0.243 | 0.956 | 0.898 | 0.954 | 0.945 | 0.450 | 0.416 | 92 | 100 | 98 | 29 | 24 | 4.98E−06 | >1.00E−04 | >1.00E−04 |
| Non-Small Cell Lung Cancer | | | | | | | | | | | | | | | |
| A549/ATCC | 0.370 | 0.884 | 0.895 | 0.851 | 0.825 | 0.503 | 0.369 | 102 | 94 | 89 | 25 | | 4.11E−06 | 9.65E−05 | >1.00E−04 |
| EKVX | 0.410 | 0.723 | 0.747 | 0.789 | 0.752 | 0.603 | 0.500 | 108 | 121 | 109 | 62 | 29 | 2.27E−05 | >1.00E−04 | >1.00E−04 |
| HOP-62 | 0.377 | 0.792 | 0.757 | 0.811 | 0.781 | 0.722 | 0.545 | 92 | 105 | 97 | 83 | 40 | 5.94E−05 | >1.00E−04 | >1.00E−04 |
| HOP-92 | 0.263 | 1.240 | 1.227 | 1.186 | 1.181 | 0.950 | 0.924 | 99 | 94 | 94 | 70 | 68 | >1.00E−04 | >1.00E−04 | >1.00E−04 |
| NCI-H460 | 0.072 | 0.606 | 0.589 | 0.698 | 0.554 | 0.343 | 0.171 | 97 | 117 | 90 | 51 | 18 | 1.05E−05 | >1.00E−04 | >1.00E−04 |
| NCI-H522 | 0.816 | 1.161 | 1.047 | 0.976 | 1.018 | 0.859 | 0.808 | 67 | 46 | 58 | 12 | −1 | . | 8.45E−05 | >1.00E−04 |
| Colon Cancer | | | | | | | | | | | | | | | |
| COLO 205 | 0.228 | 0.865 | 0.856 | 0.973 | 0.901 | 0.564 | 0.403 | 99 | 117 | 106 | 53 | 27 | 1.28E−05 | >1.00E−04 | >1.00E−04 |
| HCT-116 | 0.272 | 0.715 | 0.701 | 0.673 | 0.598 | 0.345 | 0.212 | 97 | 91 | 74 | 16 | −22 | 2.58E−06 | 2.67E−05 | >1.00E−04 |
| HCT-15 | 0.194 | 0.848 | 0.867 | 0.844 | 0.758 | 0.599 | 0.567 | 103 | 99 | 86 | 62 | 57 | >1.00E−04 | >1.00E−04 | >1.00E−04 |

TABLE 8-continued

Dose-Response Data for Compound Z3 including GI50, TGI and LC50 values.

| | Time | | | Log10 Concentration | | | | | | | | | | | |
|---|---|---|---|---|---|---|---|---|---|---|---|---|---|---|---|
| | | | Mean Optical Densities | | | | | Percent Growth | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| KM12 | 0.967 | 1.999 | 2.115 | 2.070 | 2.014 | 1.230 | 1.108 | 111 | 107 | 101 | 25 | 14 | 4.75E−06 | >1.00E−04 | >1.00E−04 |
| SW-620 | 0.127 | 0.571 | 0.549 | 0.591 | 0.556 | 0.413 | 0.344 | 95 | 105 | 97 | 64 | 49 | 8.52E−05 | >1.00E−04 | >1.00E−04 |
| CNS Cancer | | | | | | | | | | | | | | | |
| SF-268 | 0.529 | 1.499 | 1.402 | 1.468 | 1.373 | 1.039 | 0.896 | 90 | 97 | 87 | 53 | 38 | 1.50E−05 | >1.00E−04 | >1.00E−04 |
| SF-295 | 1.003 | 1.729 | 1.727 | 1.825 | 1.667 | 1.196 | 1.110 | 100 | 113 | 91 | 27 | 15 | 4.36E−06 | >1.00E−04 | >1.00E−04 |
| SNB-19 | 0.488 | 1.256 | 1.233 | 1.306 | 1.195 | 1.195 | 0.857 | 97 | 107 | 92 | 92 | 48 | 9.01E−05 | >1.00E−04 | >1.00E−04 |
| SNB-75 | 0.346 | 0.659 | 0.639 | 0.711 | 0.700 | 0.714 | 0.646 | 94 | 117 | 113 | 118 | 96 | >1.00E−04 | >1.00E−04 | >1.00E−04 |
| U251 | 0.342 | 0.906 | 0.899 | 0.946 | 0.882 | 0.506 | 0.308 | 99 | 107 | 96 | 29 | −10 | 4.85E−06 | 5.56E−05 | >1.00E−04 |
| Melanoma | | | | | | | | | | | | | | | |
| SK-MEL-2 | 0.669 | 1.230 | 1.116 | 1.144 | 1.211 | 0.805 | 0.772 | 80 | 85 | 97 | 24 | 18 | 4.41E−06 | >1.00E−04 | >1.00E−04 |
| SK-MEL-28 | 0.205 | 0.490 | 0.444 | 0.503 | 0.479 | 0.499 | 0.472 | 84 | 105 | 96 | 103 | 94 | >1.00E−04 | >1.00E−04 | >1.00E−04 |
| SK-MEL-5 | 0.585 | 1.341 | 1.192 | 1.431 | 1.438 | 0.745 | 0.700 | 80 | 112 | 113 | 21 | 15 | 4.84E−06 | >1.00E−04 | >1.00E−04 |
| UACC-62 | 0.696 | 1.097 | 1.074 | 1.029 | 0.861 | 0.753 | 0.783 | 94 | 83 | 41 | 14 | 22 | 6.13E−07 | >1.00E−04 | >1.00E−04 |
| Ovarian Cancer | | | | | | | | | | | | | | | |
| IGROV1 | 0.318 | 0.543 | 0.384 | 0.460 | 0.371 | 0.367 | 0.342 | 29 | 63 | 23 | 22 | 10 | . | >1.00E−04 | >1.00E−04 |
| OVCAR-3 | 0.486 | 0.755 | 0.728 | 0.760 | 0.677 | 0.594 | 0.537 | 90 | 102 | 71 | 40 | 19 | 4.77E−06 | >1.00E−04 | >1.00E−04 |
| OVCAR-4 | 0.225 | 0.731 | 0.690 | 0.763 | 0.639 | 0.631 | 0.693 | 92 | 106 | 82 | 80 | 92 | >1.00E−04 | >1.00E−04 | >1.00E−04 |
| OVCAR-5 | 0.389 | 0.712 | 0.679 | 0.671 | 0.658 | 0.559 | 0.438 | 90 | 87 | 83 | 53 | 15 | 1.17E−05 | >1.00E−04 | >1.00E−04 |
| OVCAR-8 | 0.575 | 0.761 | 0.791 | 0.793 | 0.739 | 0.637 | 0.484 | 116 | 117 | 88 | 33 | −16 | 4.98E−06 | 4.77E−05 | >1.00E−04 |
| SK-OV-3 | 0.365 | 0.954 | 0.906 | 0.944 | 0.936 | 0.862 | 0.877 | 92 | 98 | 97 | 84 | 87 | >1.00E−04 | >1.00E−04 | >1.00E−04 |
| Renal Cancer | | | | | | | | | | | | | | | |
| 786-0 | 0.380 | 1.102 | 1.004 | 1.084 | 0.998 | 0.749 | 0.434 | 86 | 98 | 86 | 51 | 7 | 1.06E−05 | >1.00E−04 | >1.00E−04 |
| ACHN | 0.377 | 0.677 | 0.681 | 0.711 | 0.660 | 0.511 | 0.373 | 102 | 112 | 94 | 45 | −1 | 7.84E−06 | 9.48E−05 | >1.00E−04 |
| CAKI-1 | 0.799 | 1.286 | 1.272 | 1.301 | 1.184 | 0.901 | 0.730 | 97 | 103 | 79 | 21 | −9 | 3.16E−06 | 5.09E−05 | >1.00E−04 |
| SN12C | 0.435 | 0.546 | 0.532 | 0.529 | 0.492 | 0.376 | 0.676 | 87 | 84 | 51 | −14 | 217 | . | . | >1.00E−04 |
| TK-10 | 1.040 | 1.259 | 1.295 | 1.321 | 1.331 | 1.214 | 0.963 | 117 | 128 | 133 | 80 | −7 | 2.19E−05 | 8.22E−05 | >1.00E−04 |
| UO-31 | 0.623 | 1.542 | 1.411 | 1.527 | 1.408 | 0.927 | 0.805 | 86 | 98 | 85 | 33 | 20 | 4.75E−06 | >1.00E−04 | >1.00E−04 |
| Prostate Cancer | | | | | | | | | | | | | | | |
| PC-3 | 0.355 | 1.082 | 1.080 | 1.050 | 1.008 | 0.640 | 0.439 | 100 | 96 | 90 | 39 | 12 | 6.12E−06 | >1.00E−04 | >1.00E−04 |
| DU-145 | 0.232 | 0.542 | 0.506 | 0.521 | 0.504 | 0.431 | 0.329 | 88 | 93 | 88 | 64 | 31 | 2.68E−05 | >1.00E−04 | >1.00E−04 |
| Breast Cancer | | | | | | | | | | | | | | | |
| MCF7 | 0.115 | 0.537 | 0.498 | 0.605 | 0.475 | 0.367 | 0.245 | 91 | 116 | 85 | 60 | 31 | 2.15E−05 | >1.00E−04 | >1.00E−04 |
| NCI/ADR-RES | 0.267 | 0.477 | 0.411 | 0.462 | 0.413 | 0.356 | 0.324 | 69 | 93 | 69 | 42 | 27 | 5.26E−06 | >1.00E−04 | >1.00E−04 |
| MDA-MB-231/ATCC | 0.591 | 0.829 | 0.752 | 0.755 | 0.732 | 0.768 | 0.941 | 68 | 69 | 59 | 75 | 147 | >1.00E−04 | >1.00E−04 | >1.00E−04 |
| MS 578T | 0.604 | 0.848 | 0.849 | 0.911 | 0.851 | 0.811 | 0.745 | 101 | 126 | 101 | 85 | 55 | >1.00E−04 | >1.00E−04 | >1.00E−04 |
| MDA-MB-435 | 1.095 | 1.843 | 1.780 | 1.913 | 1.779 | 1.398 | 1.301 | 92 | 109 | 91 | 40 | 28 | 6.50E−06 | >1.00E−04 | >1.00E−04 |
| BT-549 | 0.294 | 0.570 | 0.571 | 0.641 | 0.591 | 0.518 | 0.485 | 100 | 126 | 107 | 81 | 69 | >1.00E−04 | >1.00E−04 | >1.00E−04 |
| T-47D | 0.393 | 0.677 | 0.615 | 0.700 | 0.613 | 0.549 | 0.631 | 78 | 108 | 78 | 55 | 84 | >1.00E−04 | >1.00E−04 | >1.00E−04 |

Figure 15:
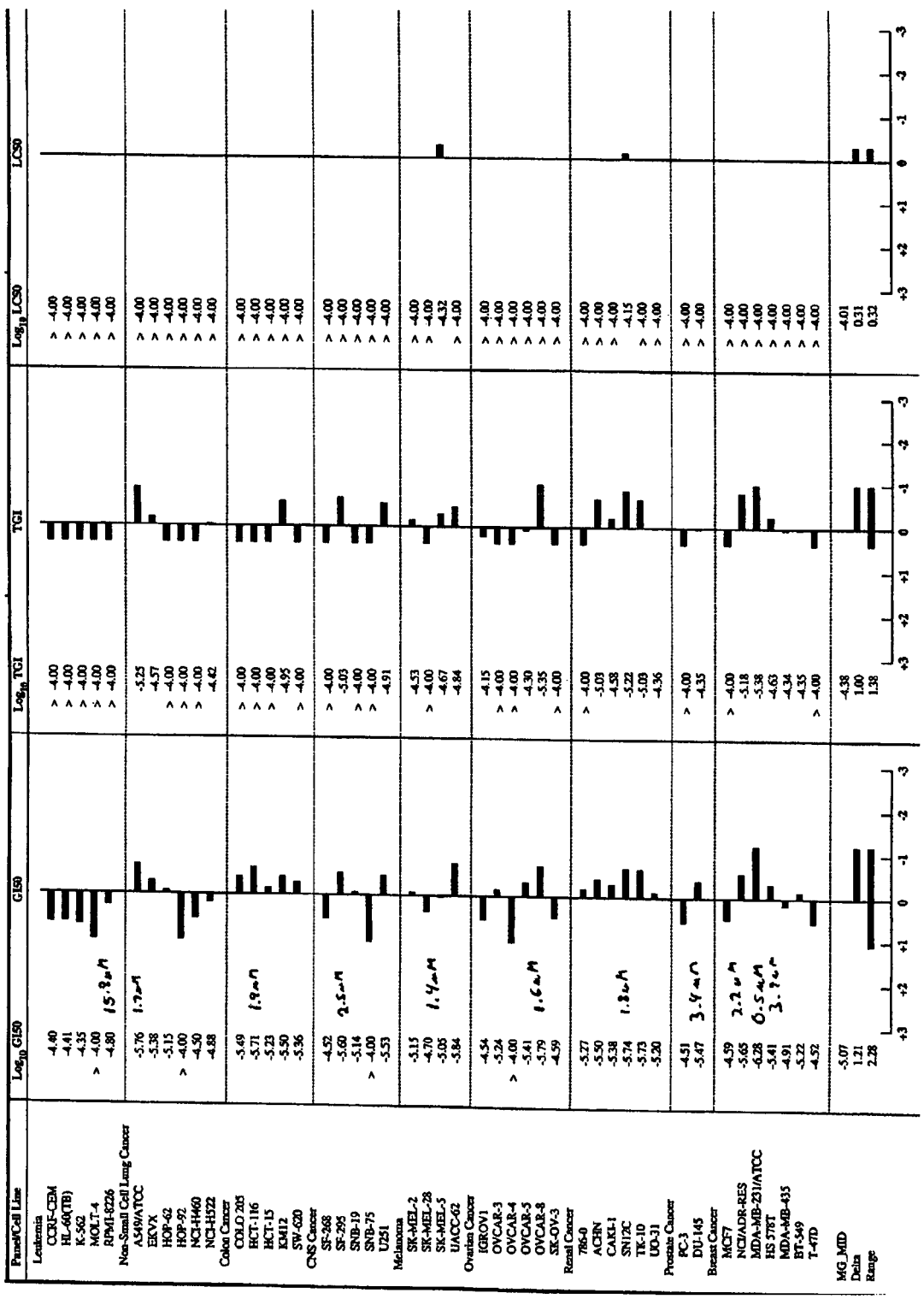
FIG. 15 illustrates results for compound Z2 using the NCI panel and shows mean graphs for GI50, TGI, and LC50 values.
Figure 16:
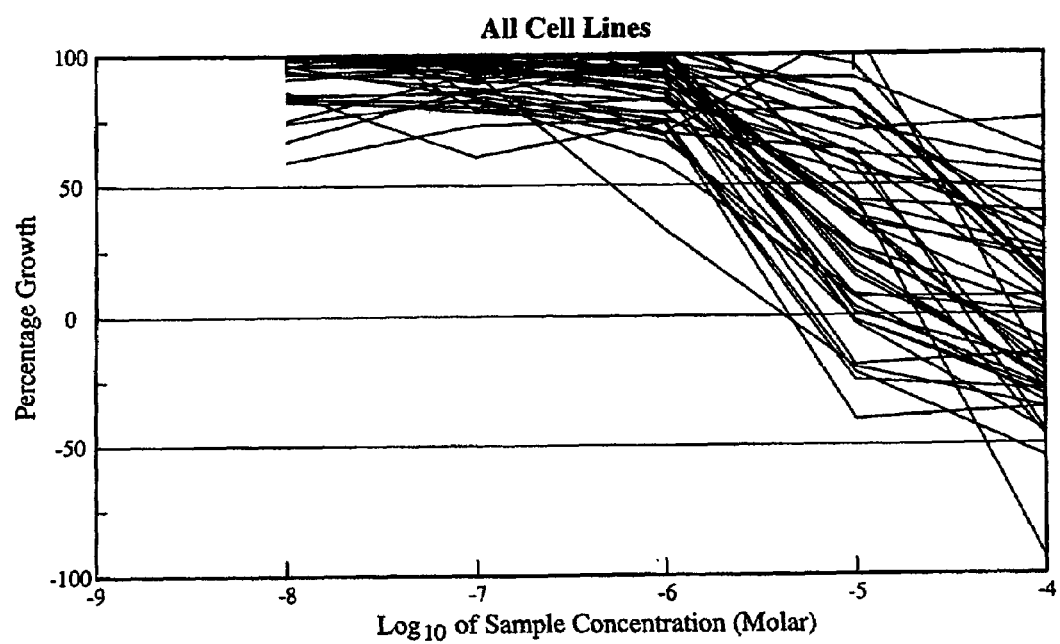
FIG. 16 illustrates results for compound Z2 using the NCI panel and shows dose response curves for all cell lines (percentage growth versus $log_{10}$ of sample concentration).
Figure 17A:
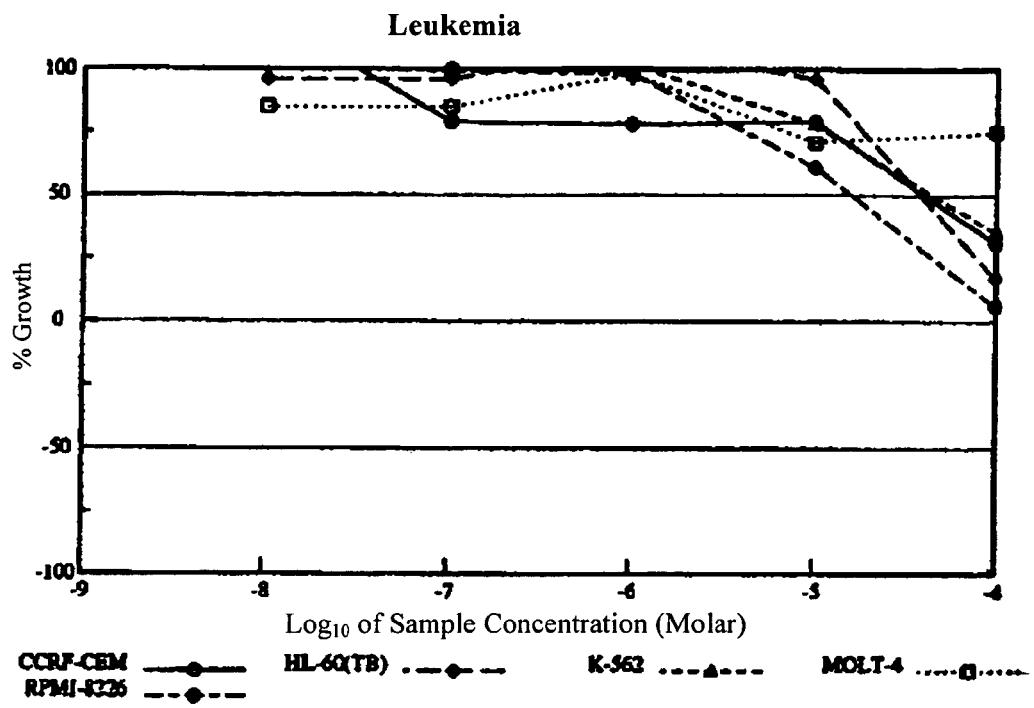
FIG. 17 illustrates results for compound Z2 using the NCI panel and shows individual dose response curves (percentage growth versus $log_{10}$ of sample concentration) for several cancer cell types: leukemia, CNS cancer, renal cancer, non-small cell lung cancer, melanoma, prostate cancer, colon cancer, ovarian cancer, and breast cancer.
Figure 17B:
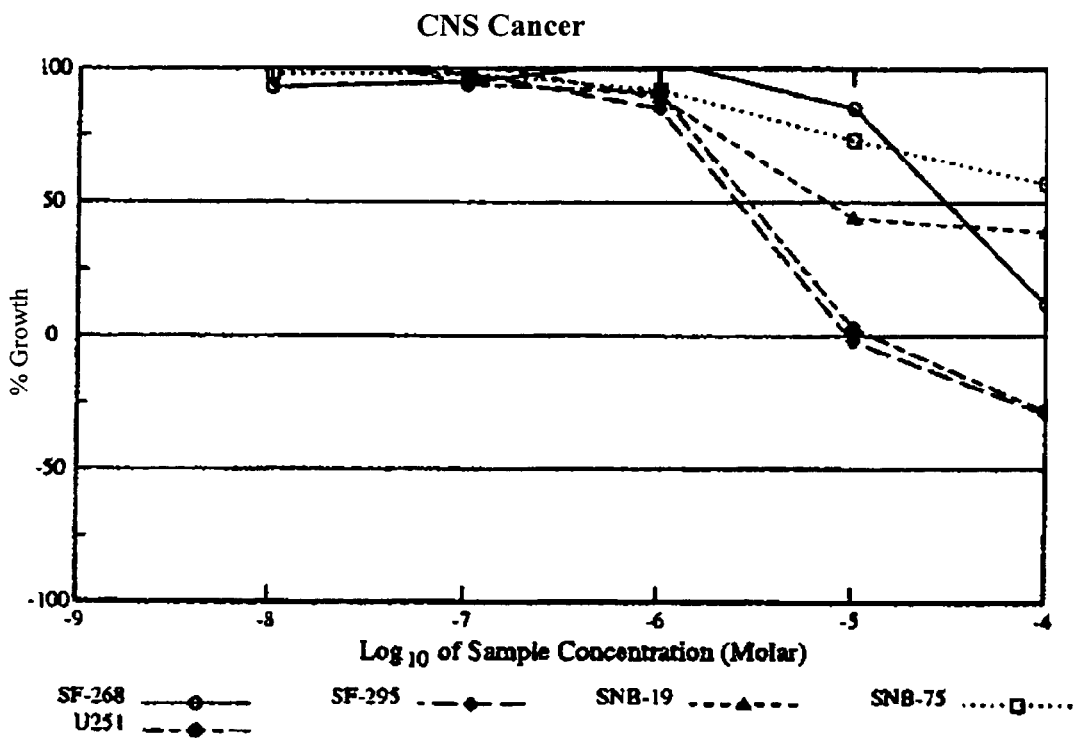
Figure 17C:
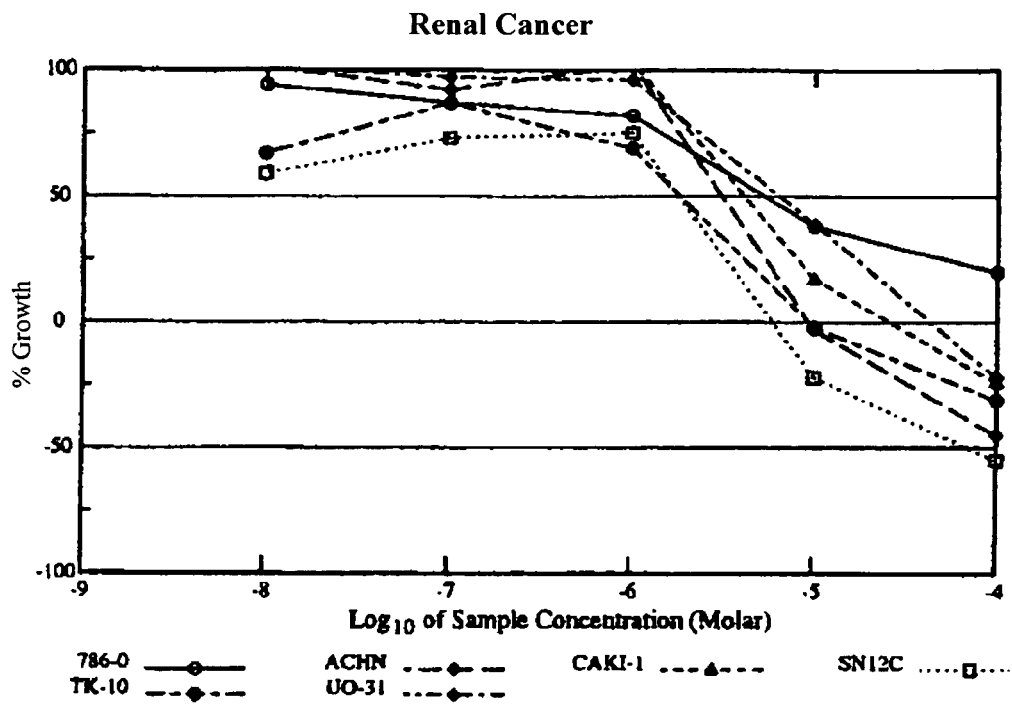
Figure 17D:
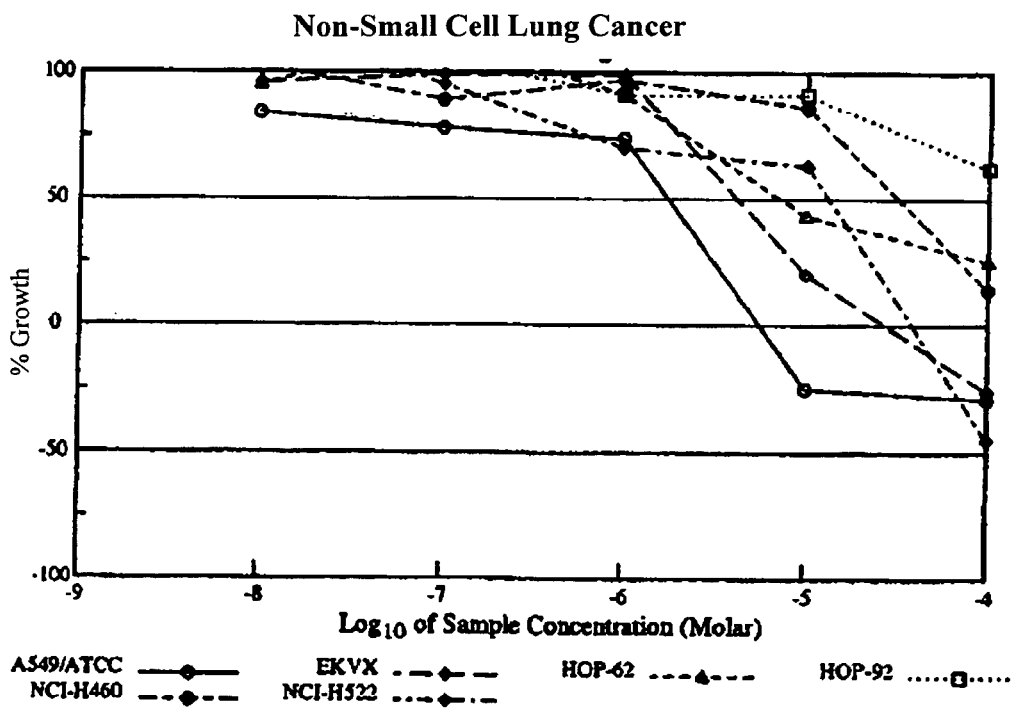
Figure 17E:
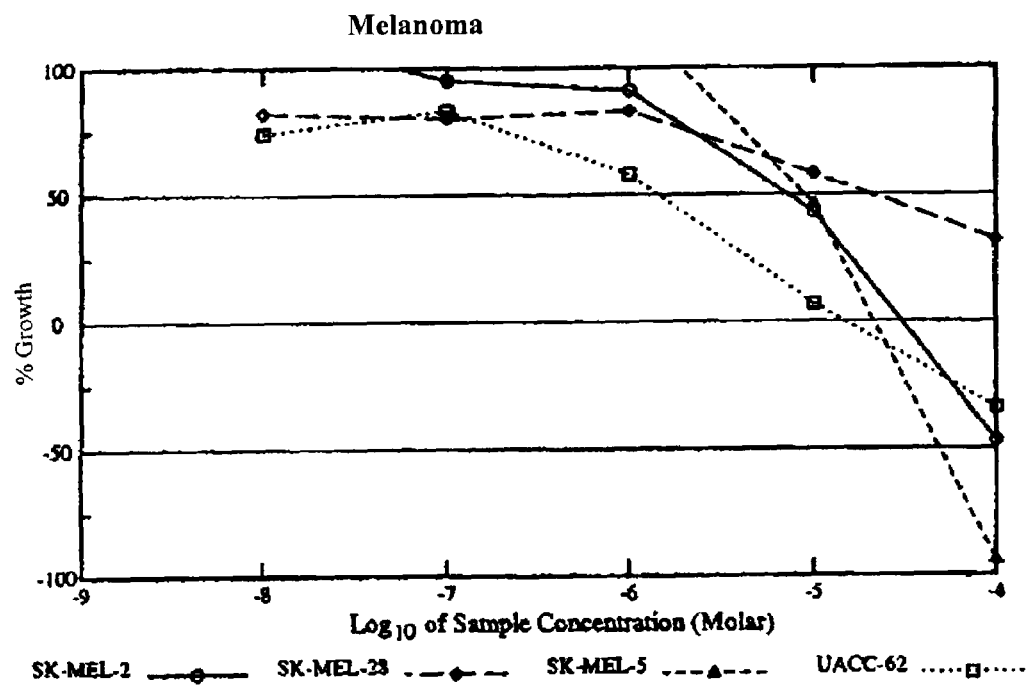
Figure 17F:
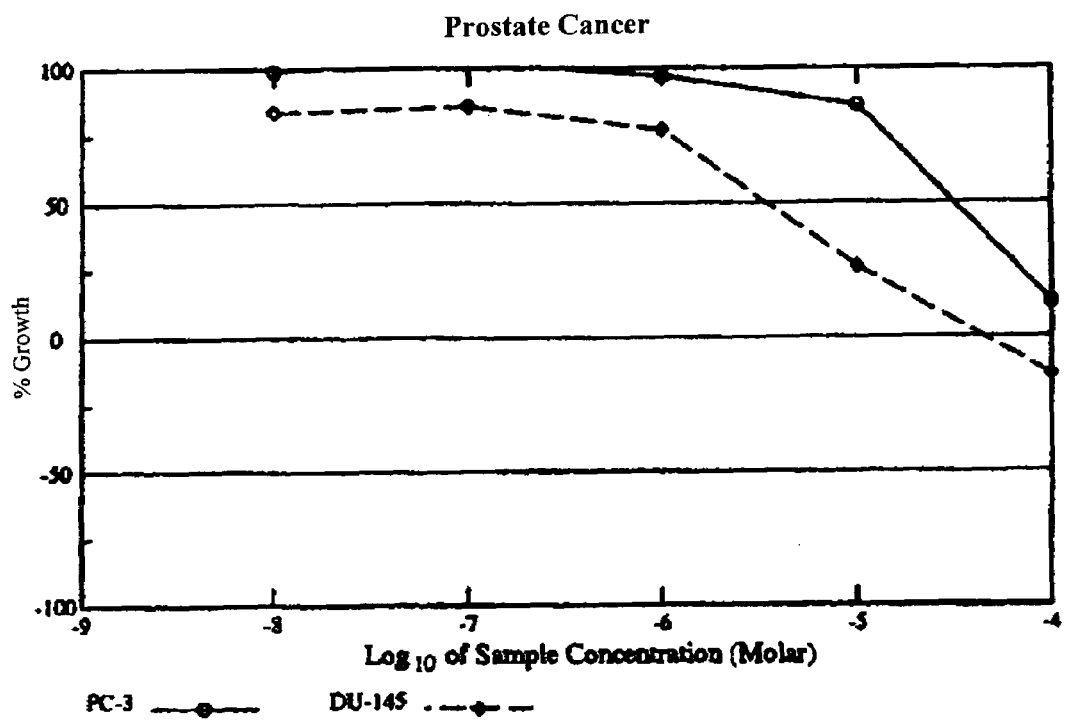
Figure 17G:
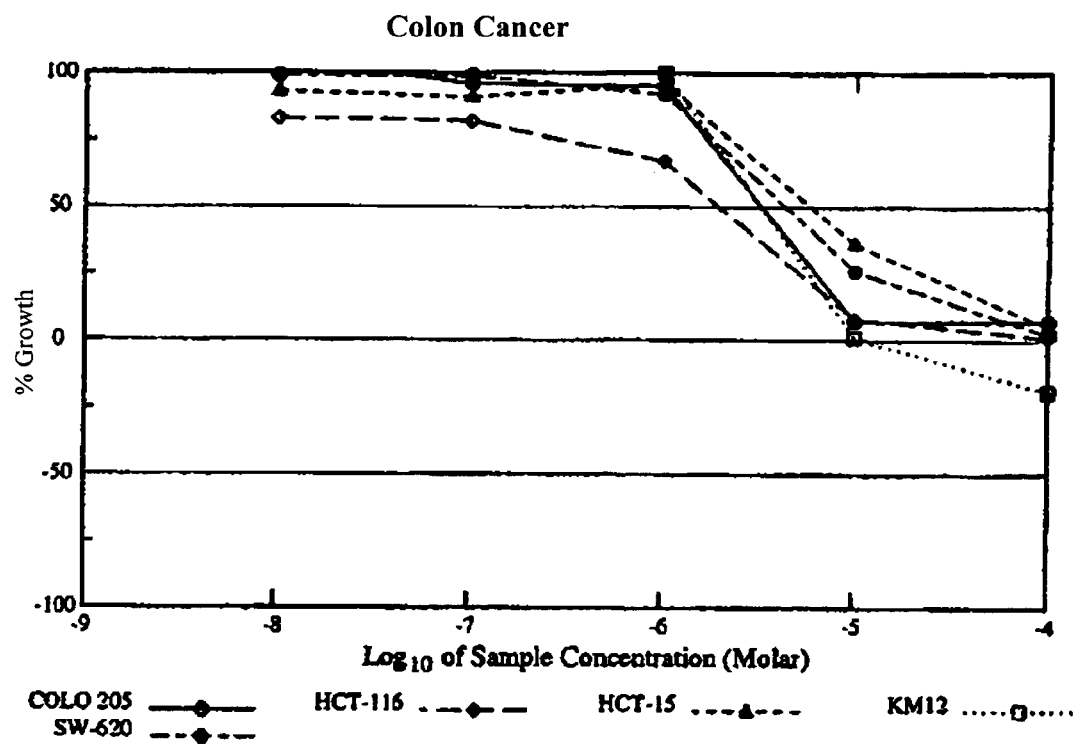
Figure 17H:
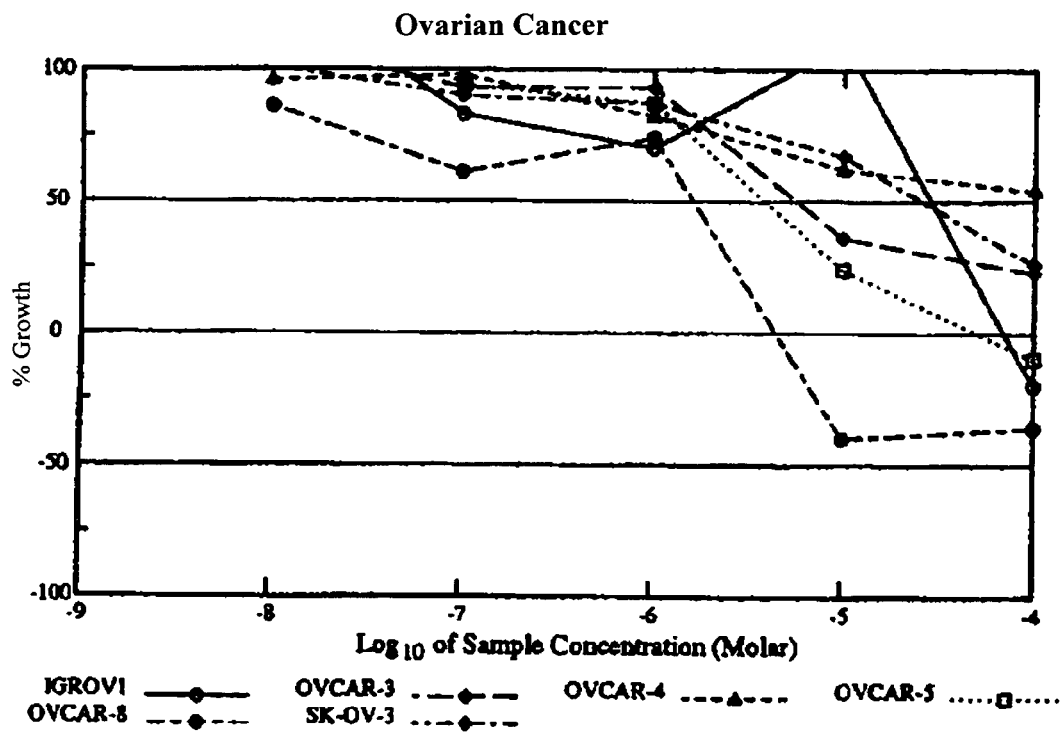
Figure 17J:
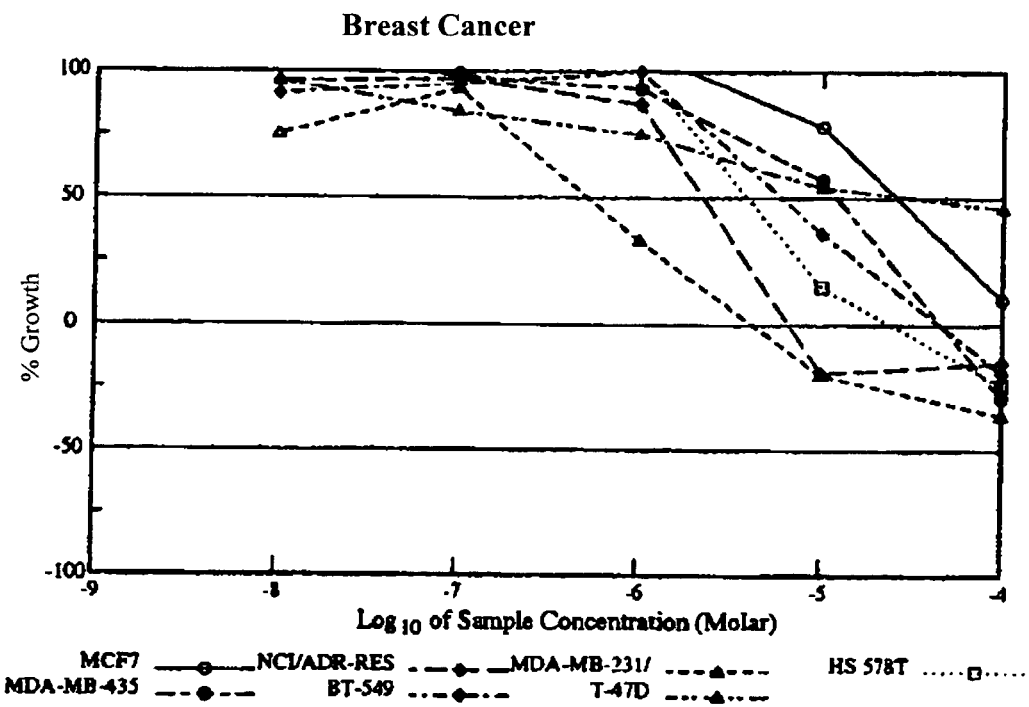
Figure 20A:
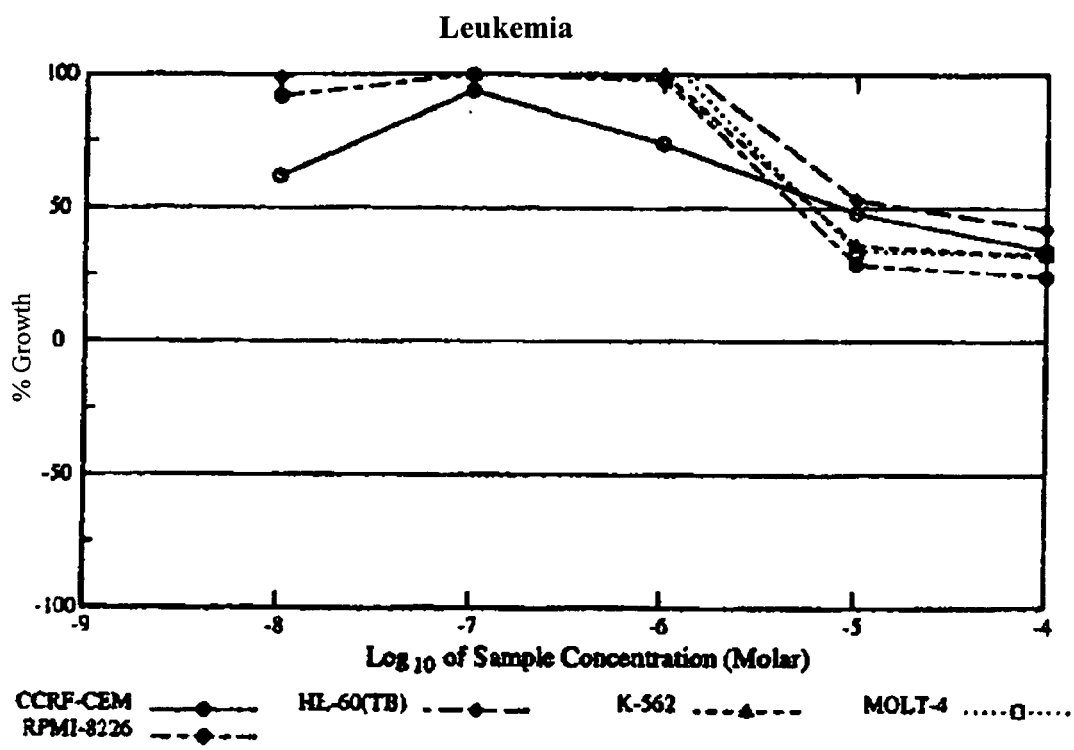
FIG. 20 illustrates results for compound Z3 using the NCI panel and shows individual dose response curves (percentage growth versus $log_{10}$ of sample concentration) for several cancer cell types: leukemia, CNS cancer, renal cancer, non-small cell lung cancer, melanoma, prostate cancer, colon cancer, ovarian cancer, and breast cancer.
Figure 20B:
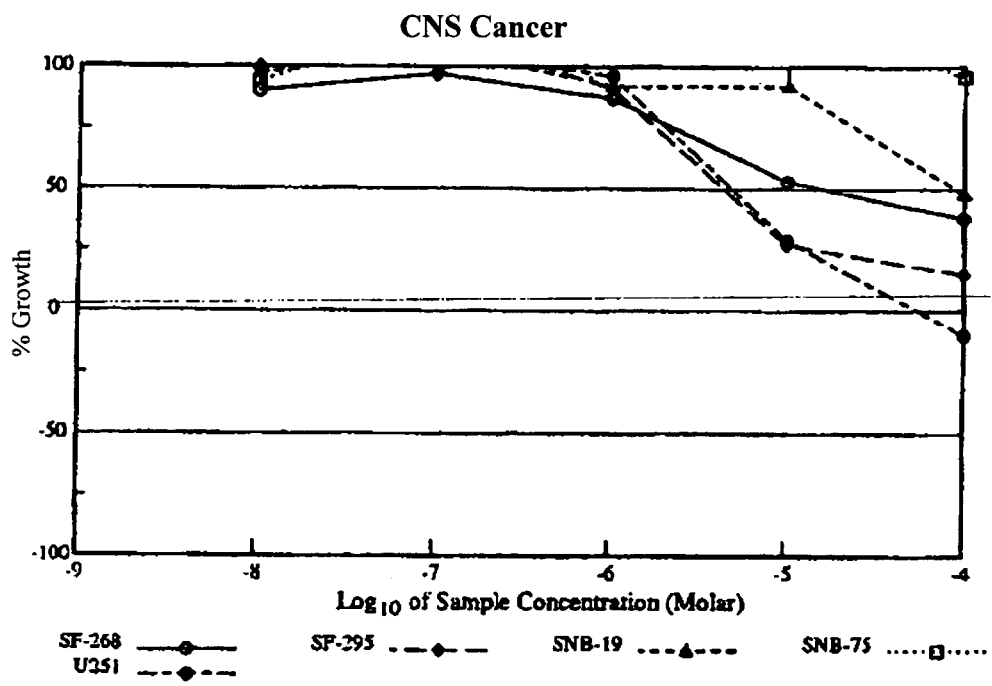
Figure 20C:
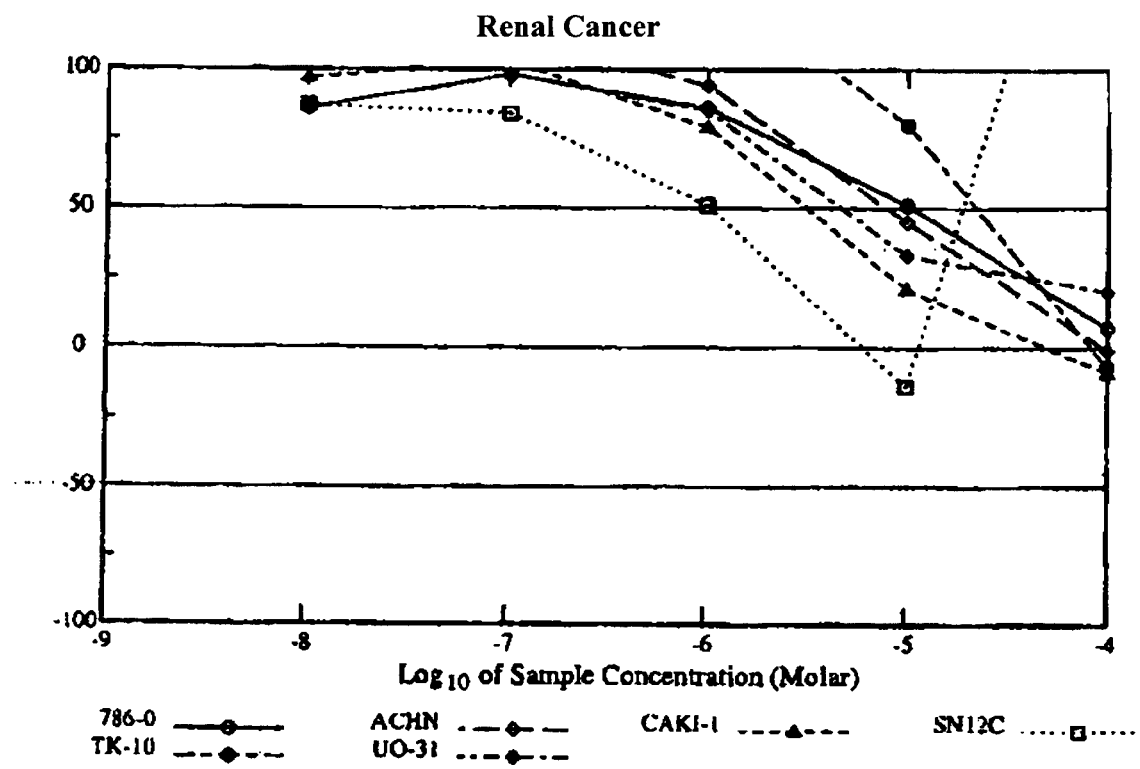
Figure 20D:
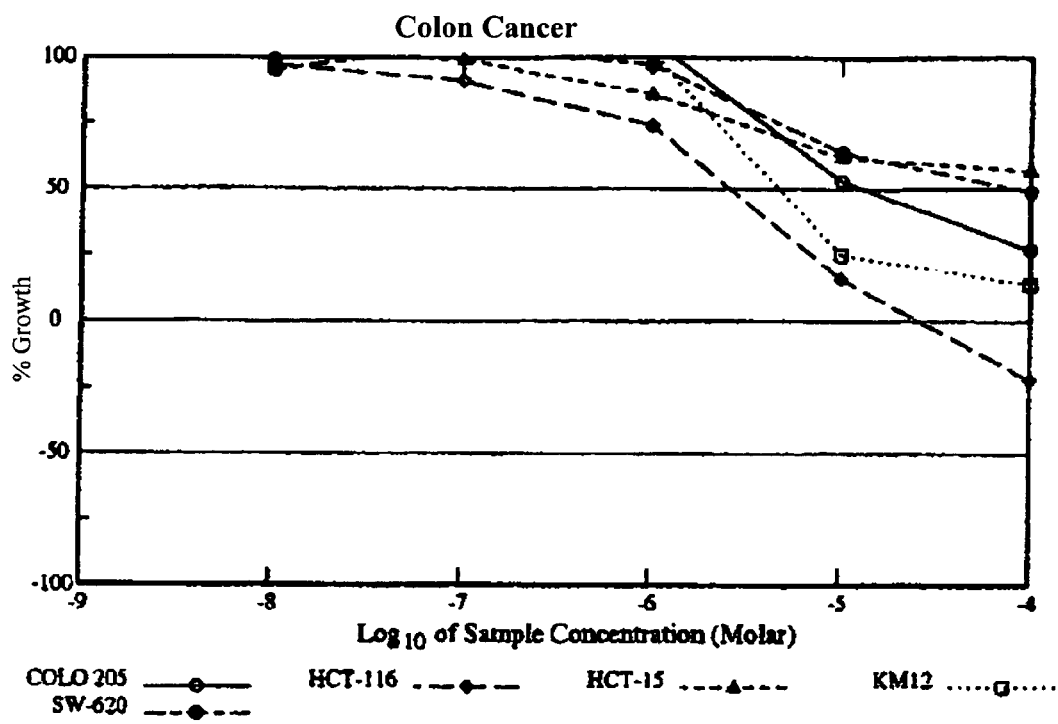
Figure 20E:
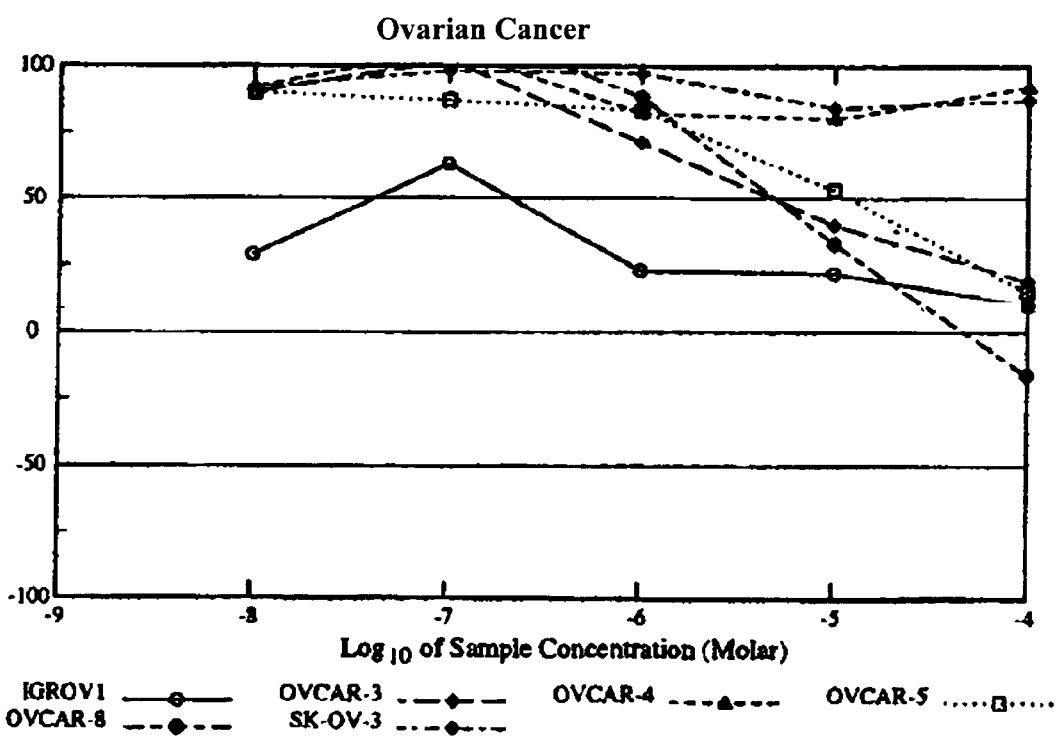
Figure 20F:
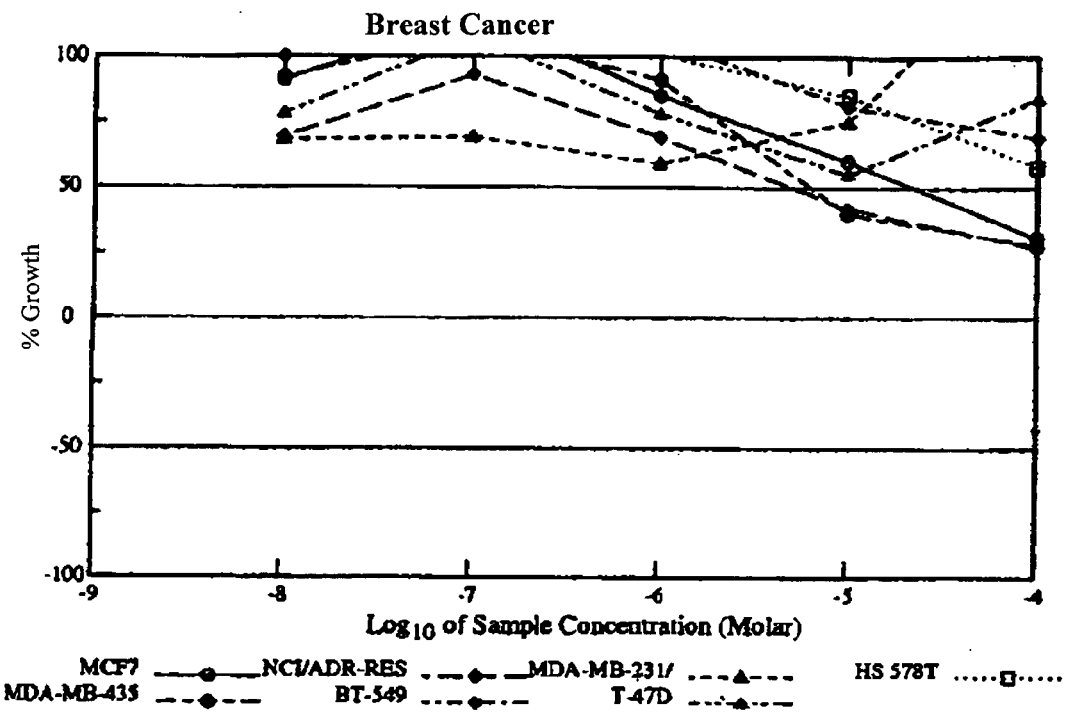
Figure 20G:
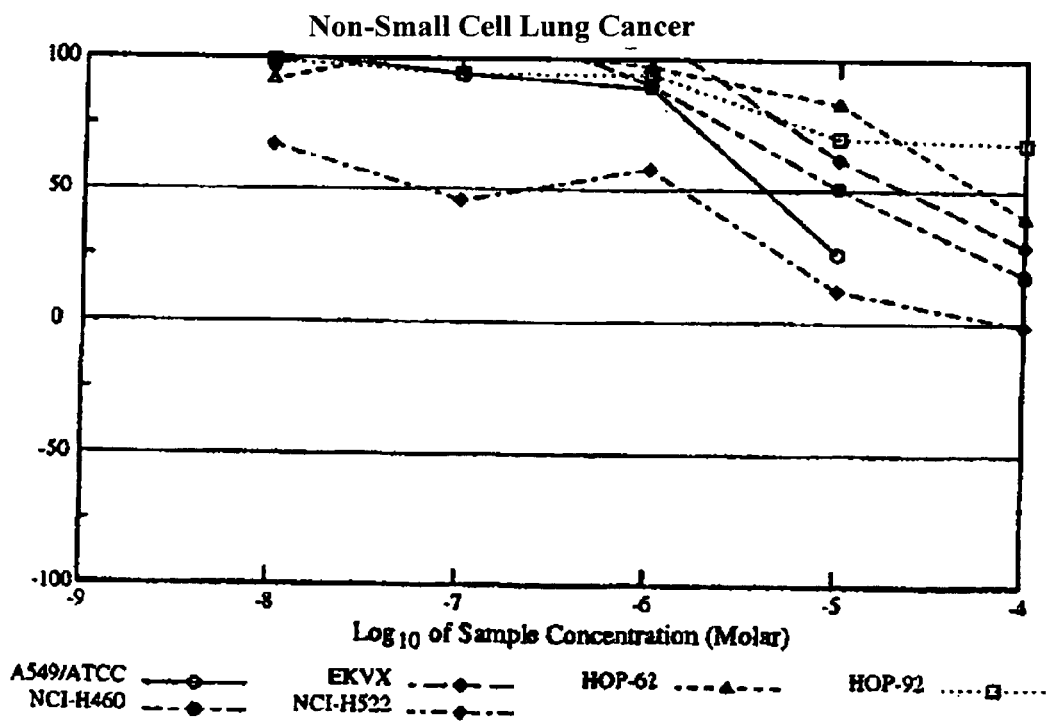
Figure 20H:
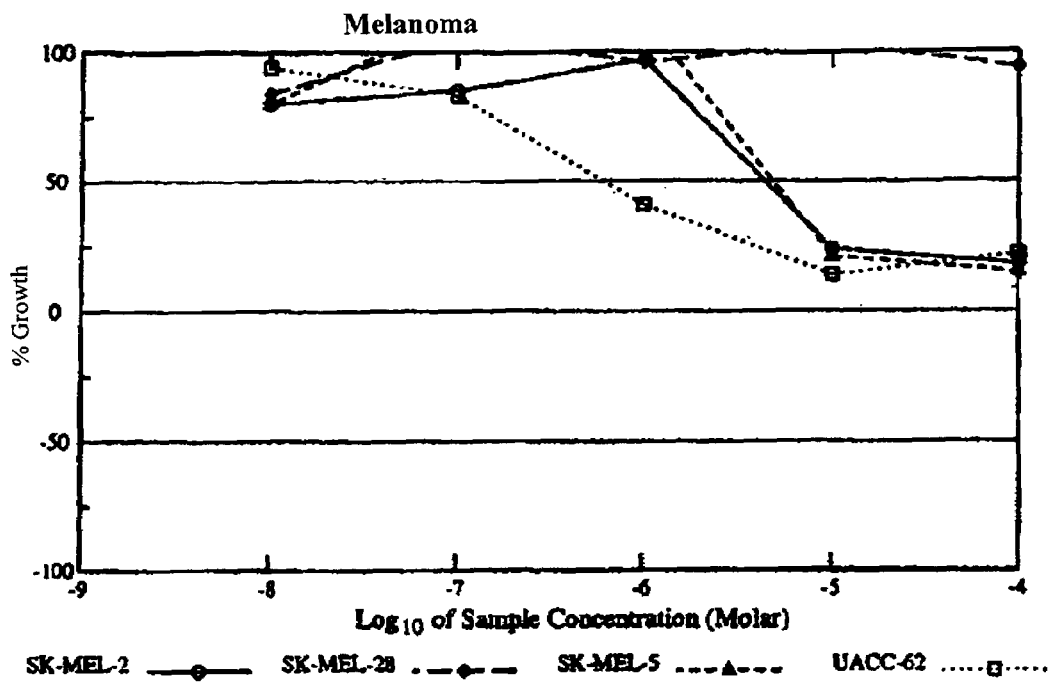
Figure 20J:
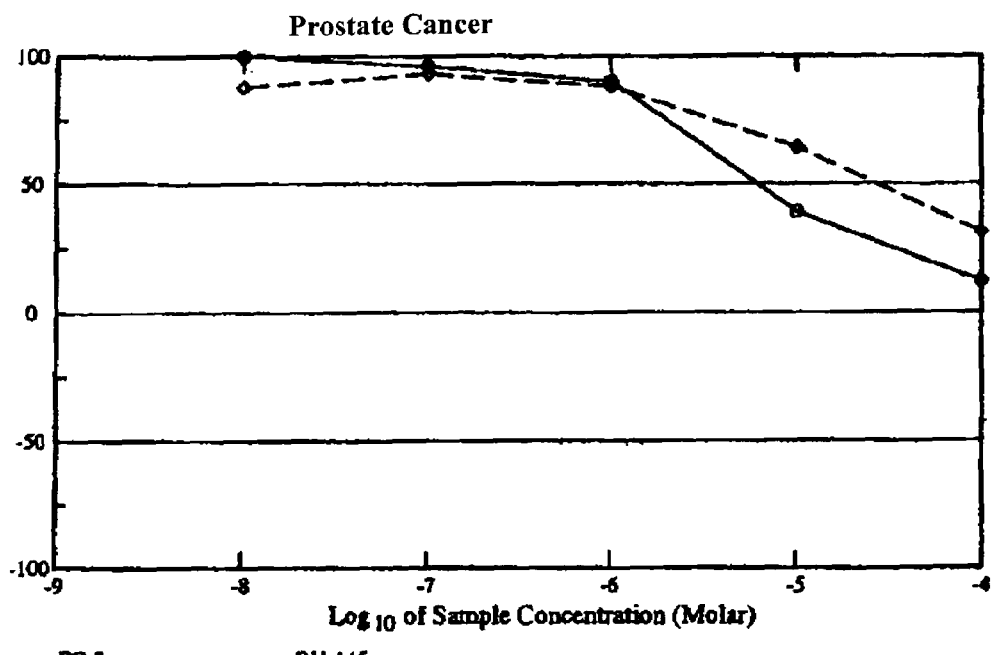
Figure 18:
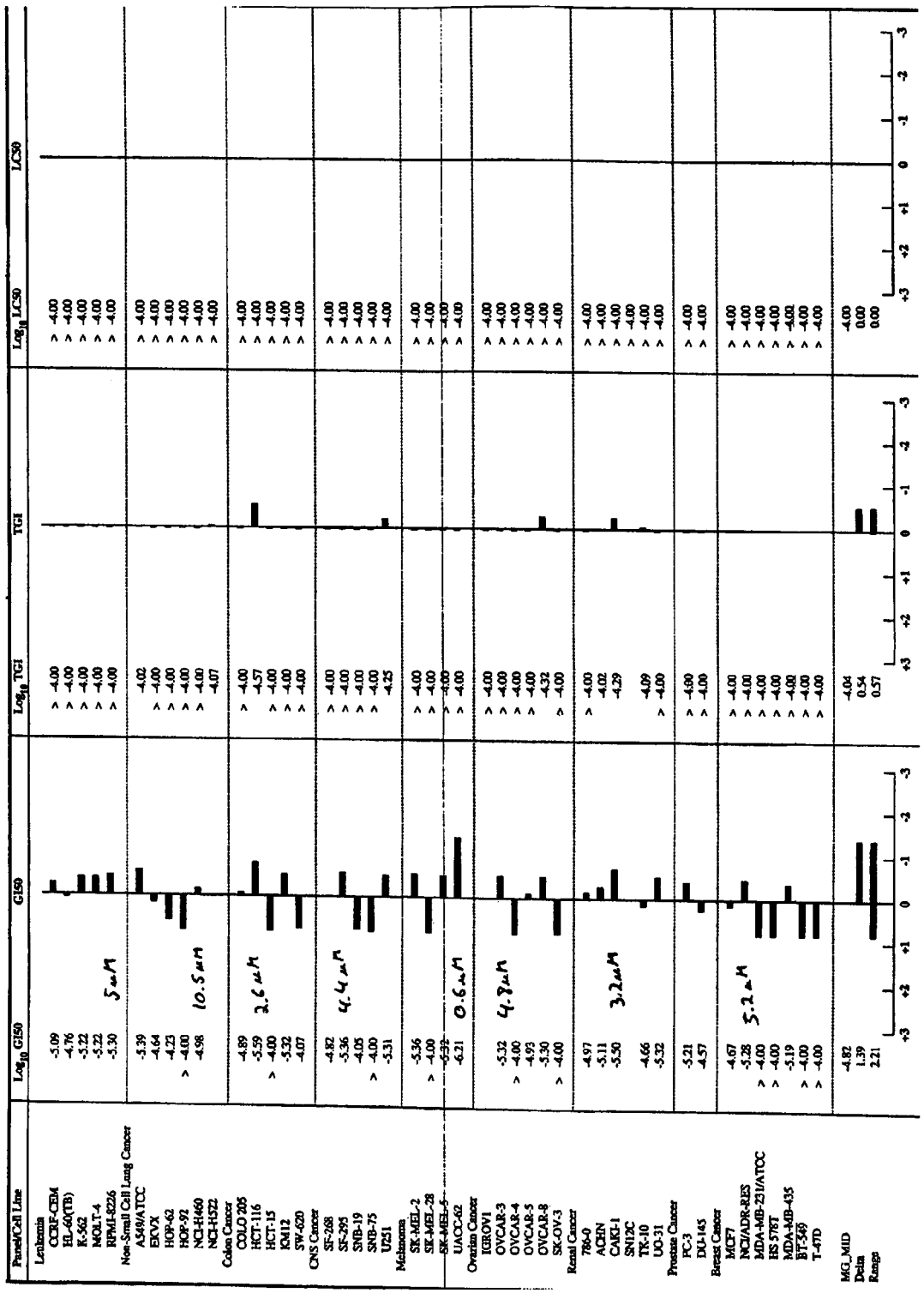
FIG. 18 illustrates results for compound Z3 using the NCI panel and shows mean graphs for GI50, TGI, and LC50 values.
Figure 19:
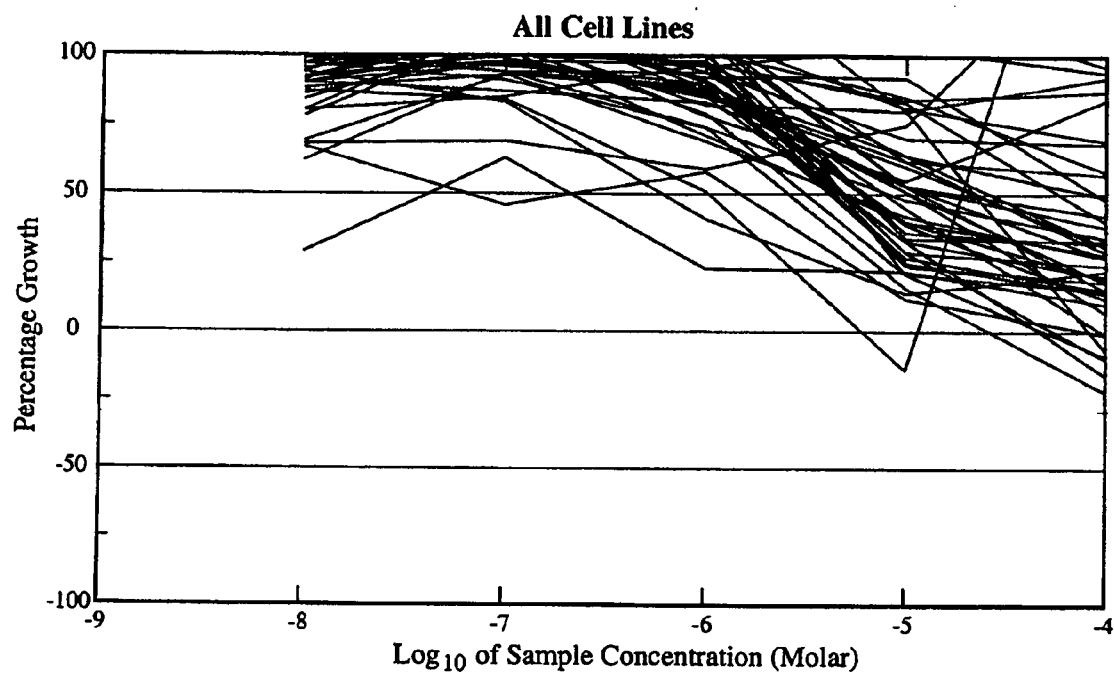
FIG. 19 illustrates results for compound Z3 using the NCI panel and shows dose response curves for all cell lines (percentage growth versus $log_{10}$ of sample concentration).

Further data relating to the cancer cell panel screen are shown in FIG. 15, FIG. 16, and FIG. 17 (results for compound Z2) and in FIG. 18, FIG. 19, and FIG. 20 (results for compound Z3).

Example 4

Cancer Screening Using Cell Panel

Potential anti-cancer agents are screened, and in certain instances were screened, using a screening system provided and performed by the National Cancer Institute (NCI). See http://dtp.nci.nih.gov/docs/misc/common_files/submit_compounds.html. The Developmental Therapeutics Program (DTP) of NCI operates an anti-cancer screening program. The program accepts both natural and synthetic compounds. For screening of natural products extracts, the Natural Products Branch can be contacted.

DTP Human Tumor Cell Line Screen. Process:

The operation of this screen utilizes 60 different human tumor cell lines, representing leukemia, melanoma and cancers of the lung, colon, brain, ovary, breast, prostate, and kidney. The aim is to prioritize for further evaluation, synthetic compounds or natural product samples showing selective growth inhibition or cell killing of particular tumor cell lines. This screen is unique in that the complexity of a 60 cell line dose response produced by a given compound results in a biological response pattern which can be utilized in pattern recognition algorithms. Using these algorithms, it is possible to assign a putative mechanism of action to a test compound, or to determine that the response pattern is unique and not similar to that of any of the standard prototype compounds included in the NCI database (see DTP Overview tab). In addition, following characterization of various cellular molecular targets in the 60 cell lines, it may be possible to select compounds most likely to interact with a specific molecular target.

Methodology of the In Vitro Cancer Screen

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

Three Cell Line Prescreen

The three cell line, one-dose prescreen identifies a large proportion of the compounds that would be inactive in multi-dose 60 cell line screening. Computer modeling indicates that approximately 50% of compounds can be eliminated by this prescreen without a significant decrease in the ability to identify active agents, while increasing the throughput and efficiency of the main cancer screen with limited loss of information. The current assay utilizes a 384 well plate format and fluorescent staining technologies resulting in greater screening capacity for testing of synthetic samples.

Cell Lines: The cell lines are grown in the same manner as for the 60 cell line screen (see above). The cells are plated a densities of 5000 cells/well (MCF7), 1000 cells/well (NCI-H460), and 7500 cells/well (SF-268) to allow for varying doubling time of the cell lines. Each plate contains all three cell lines, a series of dilutions of standard agents, total kill wells and appropriate controls. Plates are incubated under standard conditions for 24 hours prior to addition of experimental compounds or extracts.

Addition of Experimental Agents (Pure Compounds)

Experimental compounds are solubilized in dimethyl sulfoxide (DMSO) at 400-times the desired maximum test concentration (maximum final DMSO concentration of 0.25%) and stored frozen. Compounds are then diluted with complete media with 0.1% gentamicin sulfate (5 µl of test sample in 100% DMSO is added to 565 µl of complete medium). 20 µl of this solution is then dispensed into test wells containing 50 µl of cell suspension to yield a test concentration of 1.00E-04M.

Two standard drugs, meaning that their activities against the cell lines are well documented, are tested against each cell line: NSC 19893 (5-FU) and NSC 123127 (Adriamycin).

Endpoint Measurement: After compound addition, plates are incubated at standard conditions for 48 hours, 10 µl/well Alamar Blue is added and the plates are incubated for an additional 4 hours. Fluorescence is measured using an excitation wavelength of 530 nm and an emission wavelength of 590 nm.

Calculation of Percent Test Cell Growth/Control (untreated) Cell Growth (T/C). Percent growth is calculated on a plate-by-plate basis for test wells relative to control wells. Percent Growth is expressed as the ratio of fluorescence of the test well to the average fluorescence of the control wells*100.

Criteria for Activity. Compounds which inhibit the growth of any of the 3 cell lines to 32% or less than control growth are automatically forwarded for testing in the 60 cell line assay. To validate the selection of 32% as the cutoff point for activity, 208 compounds that produced T/Cs of 32% to 50% in any one cell line in the 3 cell line assay were forwarded to the 60 cell line assay. Of those 208, 17% were considered sufficiently active to warrant a confirmatory 60 cell line experiment. Six percent of the 208 demonstrated confirmed activity upon retest in the 60 cell line screen and were reviewed for possible in vivo testing. Less than 1% of the original 208 were actually selected for follow-up in vivo hollow fiber testing.

Modifications to Screen for Natural Product Extracts. Cell Lines: Cells are harvested as above and plated onto a 96-Well flat-bottom, polystyrene plate in 180 µl standard RPMI-1640 media, at densities of 10,000 cells/well (MCF7), 7500 cells/well (NCI-H460), and 15,000 cells/well (SF-268). Each cell line is plated on duplicate plates: one time-zero plate, and one drug background plate is made with media only added.

Addition of Extracts: Extracts are prepared in DMSO at 400-times the desired maximum test concentration and stored frozen. Extracts are diluted in complete media with 0.1% Gentamicin sulfate and dispensed into wells in a volume of 20

µl to yield a test concentration of 100 µg/ml. NSC 123127 (Adriamycin) is used as the standard and is included on each plate.

Endpoint Measurement: Cells are fixed in situ by the addition of cold TCA (final concentration 10% TCA) and incubated for 60 minutes at 4° C. The supernatant is discarded, plates washed five times with tap water and air-dried. SRB at a 0.4% (w/v) in 1% acetic acid is added to each well and the plates are incubated for 10 minutes at room temperature. Unbound dye is removed by washing six times with 1% acetic acid and the plates are air-dried. Bound SRB is solubilized with 10 mM trizma base and the absorbance is measured at a wavelength of 515 mm.

Calculation of Percent T/C: Percent growth is calculated from six control wells, time zero wells and one test well for each cell line. % Growth is calculated by the same method used in the 60-cell line primary screen.

Screening Services—Cell Lines In The In Vitro Screen: See http://dtp.nci.nih.gov/docs/misc/common_files/cell_list.html. Cell lines for the prescreen and full screen are shown in Table 9 and Table 10.

TABLE 9

Prescreen cell lines.

| Cell Line | Tumor Type |
| --- | --- |
| MCF7 | Breast |
| NCI-H460 | Lung |
| SF-268 | CNS |

TABLE 10

List of the 60 human cancer cell lines related to the NCI screen.

| Item | Cell Line Name | Panel Name |
| --- | --- | --- |
| 1 | CCRF-CEM | Leukemia |
| 2 | HL-60(TB) | Leukemia |
| 3 | K-562 | Leukemia |
| 4 | MOLT-4 | Leukemia |
| 5 | RPMI-8226 | Leukemia |
| 6 | SR | Leukemia |
| 7 | A549/ATCC | Non-Small Cell Lung |
| 8 | EKVX | Non-Small Cell Lung |
| 9 | HOP-62 | Non-Small Cell Lung |
| 10 | HOP-92 | Non-Small Cell Lung |
| 11 | NCI-H226 | Non-Small Cell Lung |
| 12 | NCI-H23 | Non-Small Cell Lung |
| 13 | NCI-H322M | Non-Small Cell Lung |
| 14 | NCI-H460 | Non-Small Cell Lung |
| 15 | NCI-H522 | Non-Small Cell Lung |
| 16 | COLO 205 | Colon |
| 17 | HCC-2998 | Colon |
| 18 | HCT-116 | Colon |
| 19 | HCT-15 | Colon |
| 20 | HT29 | Colon |
| 21 | KM12 | Colon |
| 22 | SW-620 | Colon |
| 23 | SF-268 | CNS |
| 24 | SF-295 | CNS |
| 25 | SF-539 | CNS |
| 26 | SNB-19 | CNS |
| 27 | SNB-75 | CNS |
| 28 | U251 | CNS |
| 29 | LOX IMVI | Melanoma |
| 30 | MALME-3M | Melanoma |
| 31 | M14 | Melanoma |
| 32 | SK-MEL-2 | Melanoma |
| 33 | SK-MEL-28 | Melanoma |
| 34 | SK-MEL-5 | Melanoma |
| 35 | UACC-257 | Melanoma |
| 36 | UACC-62 | Melanoma |
| 37 | IGR-OV1 | Ovarian |
| 38 | OVCAR-3 | Ovarian |
| 39 | OVCAR-4 | Ovarian |
| 40 | OVCAR-5 | Ovarian |
| 41 | OVCAR-8 | Ovarian |
| 42 | SK-OV-3 | Ovarian |
| 43 | 786-0 | Renal |
| 44 | A498 | Renal |
| 45 | ACHN | Renal |
| 46 | CAKI-1 | Renal |
| 47 | RXF 393 | Renal |
| 48 | SN12C | Renal |
| 49 | TK-10 | Renal |
| 50 | UO-31 | Renal |
| 51 | PC-3 | Prostate |
| 52 | DU-145 | Prostate |
| 53 | MCF7 | Breast |
| 54 | NCI/ADR-RES | Breast |
| 55 | MDA-MB-231/ATCC | Breast |
| 56 | HS 578T | Breast |
| 57 | MDA-MB-435 | Breast |
| 58 | MDA-N | Breast |
| 59 | BT-549 | Breast |
| 60 | T-47D | Breast |

Example 5

Synthesis and Identification of Small Molecules that Potently Induce Apoptosis in Melanoma Cells Through G1 Cell Cycle Arrest A common trait of most cancers is the ability to evade the natural cell death process. (1) Although healthy cells have tightly regulated mechanisms for apoptosis, or programmed cell death, cancerous cells often have multiple means by which they shut down this pathway and achieve immortality. Indeed, virtually every point on the apoptotic cascade has been exploited by cancer, from the p53 tumor suppressor that senses DNA damage and is inactivated in >50% of human cancers, to caspases that normally execute the apoptotic program and are mutated in certain circumstances. Thus a goal of many anti-cancer treatments is the restoration of proper apoptosis, and a significant number of anti-cancer drugs function by inducing apoptotic cell death.

The cell cycle is divided into four phases, G1, S (DNA synthesis), G2, and M (mitosis). Anti-cancer agents typically target the propensity of cancer cells to rapidly replicate their DNA and divide, and thus arrest cell growth in the synthesis (S) or mitosis (M) phase of the cell cycle. For instance, cisplatin, doxorubicin, and cyclophosphamide cause DNA damage and S phase arrest, while etoposide, taxol, and cholchicine all target operations that affect mitosis and ultimately result in G2/M arrest.

Currently, 75% of cancer deaths are due to epithelial cancers; (2) some of these forms of cancer, such as advanced malignant melanoma, are largely incurable. The lethality of melanoma is due to the intrinsic resistance of malignant melanocytes to mechanisms of apoptotic death as induced by common anti-cancer drugs. The five-year survival rates for disseminated melanoma is <5% (3) with an average survival time of 6 to 10 months. (4) The lack of sensitivity of melanoma to chemotherapy has been well documented. (5, 6) Common anti-cancer drugs such as taxol, cisplatin, etoposide, doxorubicin and other several others showed no efficacy in large randomized trials, (7) and even popular combination therapies have provided little benefits in melanoma patients. (8) This lack of clinical efficacy is supported by in vitro studies testing drugs against melanoma cell lines. (9) In fact, only one single-entity drug, dacarbazine (DTIC), has been approved by the FDA for treatment of melanoma, and this medicine provides complete remission in only 2% of patients. (6, 10) Thus, as common anti-cancer drugs are profoundly ineffective in the treatment of disseminated melanoma there is a clear need for compounds that are efficient killers of these cells and that act through non-standard anti-cancer mechanisms. Some urgency is needed in this regard as the lifetime risk for melanoma is increasing and now estimated at 1 in 75. (4)

In their natural role as a protectant from the harmful effects the sun, melanocytes are bombarded with UV light, a potent DNA damaging agent. Thus, it is not surprising that melanoma cells are exquisitely resistant to therapies targeting DNA synthesis and replication such as radiation and alkylating agents; indeed, some lines of evidence indicate that such treatments cause melanoma cells to proliferate instead of die. (11) Examination of apoptotic and cell checkpoint proteins has explored how melanoma cells evade cell death and continue to proliferate. Certain melanomas have a methylation-inactivated Apaf-1 signaling complex, (12) and/or upregulation of the caspase-inhibiting survivin protein. (13) In addition, a common chromosomal defect in melanoma cells is a deletion in the 9p21 region, resulting in the inactivation of the G1/S checkpoint through ablation of the p16INK4A protein. (14, 15)

Numerous trials have demonstrated that melanoma cells are resistant to anti-cancer drugs that arrest cellular growth in the S or M phase of the cell cycle. We identify compounds that are significantly potent against cancer cells in culture. Without wishing to be bound by a particular theory, it is believed that the compounds can act though a mechanism that arrests cell development in the G1 phase of the cell cycle. We considered that such compounds can be effective against melanoma because, unlike S- and M-phase disruptors, melanoma cells may have no intrinsic resistance to G1 phase arrestors. In addition, a compound that arrests growth in the G1 phase would have a potential advantage in being able to attack cells before they reach the critical G1/S checkpoint that is disrupted via mutation in melanoma cells. A compound or method herein can be effective without necessarily acting according to a particular theoretical or actual mechanism.

Herein we report the synthesis of a library of potential apoptotic inducers, and the screening and identification of compounds that arrest cell growth in the G1 phase of the cell cycle and cause apoptosis. This compound screening and cell cycle analysis led to the synthesis of a second set of 122 small molecules, within which five compounds with powerful pro-apoptotic activity in several melanoma cell lines and G1-arresting capacity were identified. Given the poor long-term survival prospects for late stage melanoma cancers and the lack of any effective treatments, compounds discovered through this strategy can provide important chemotherapeutic agents and further insights into combating melanoma and other cancers.

Results and Discussion

Synthesis and screening of first generation library. The building blocks used to construct the first generation library are depicted in Scheme 1. To form the amide bond, the carboxylic acids were first converted to the acid chloride and then treated in parallel with the amines (1.05 equivalent) and base. All reactions were run on a 0.035 mmol scale such that approximately 10 mg of pure product would be obtained (assuming 100% yield for a compound of 500 MW). After the amidation reaction, all compounds were purified through a small plug of silica gel. This protocol provided highly pure compounds; all 100 compounds were assessed by HPLC-MS and judged to be >90% pure, with an average purity of 95%. Exact weights were obtained for each individual compound; this allowed for each to be prepared at an exact micromolar concentration for biological testing.

Figure 21:
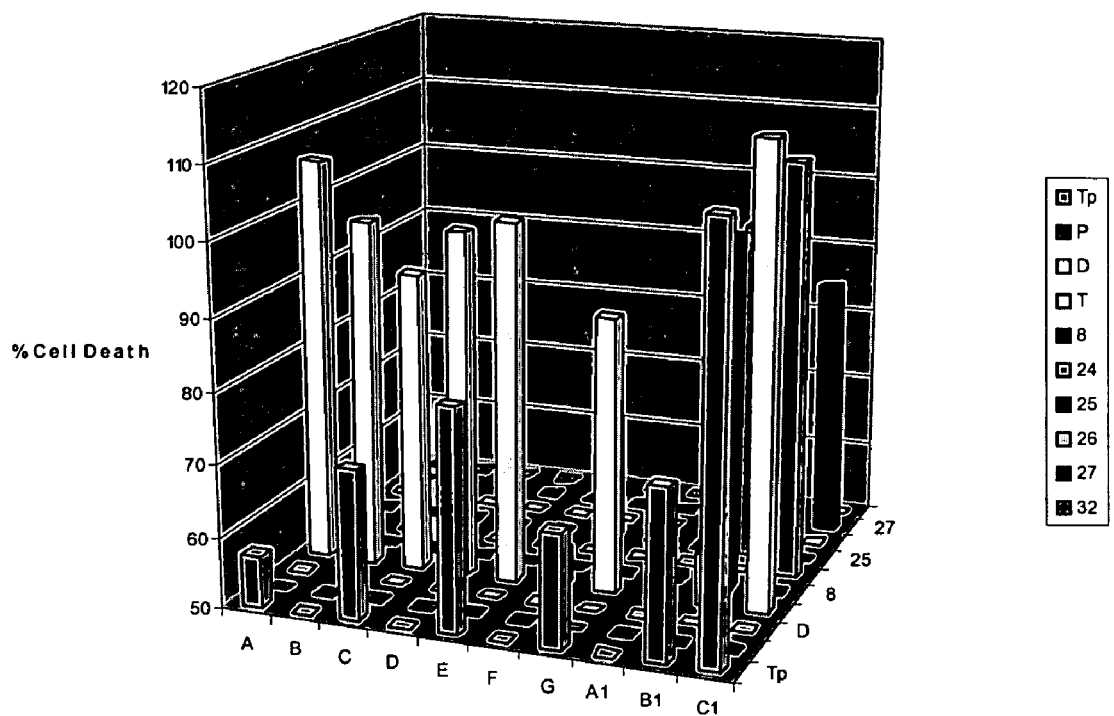
FIG. 21 illustrates the percent of cell death induced by the amide products of the first-generation combinatorial library. All compounds were evaluated at 50 μM.

The ability of the 100 amides thus produced to induce death in cancer cells was assessed by an assay based on the reduction of the MTS (3-(4,5-dimethylthiazol-2-yl)-5-(3-carboxymethoxyphenyl)-2-(4-sulfophenyl)-2H-tetrazolium, inner salt) dye. This tetrazolium dye is rapidly converted to the formazan product by living cells, and therefore provides a sensitive readout of cell life or death that can be monitored at 490 nm. As shown by the results in FIG. 21, several of the compounds rapidly (within 24 hours) and potently induced death in the U-937 cell line; this lymphoma cell line was used during this initial screening stage. Data on the dose dependence of death inducing activity was gathered for the most active compounds as identified through this high-throughput screen. As shown in Table 11, multiple compounds induced cell death with $IC_{50}$ values in the low micromolar range.

TABLE 11

Potency of death induction by hit compounds identified in the high-throughput screen, and the position where they induce cell cycle arrest.

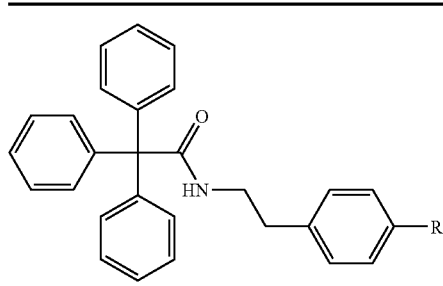

|  | $IC_{50}$ Value-U-937 cells | cell cycle arrest |
|---|---|---|
| R = CH$_3$ | 12.6 μM | G1 |
| R = H | 8.0 μM | G1 |

TABLE 11-continued

Potency of death induction by hit compounds identified in the high-throughput screen, and the position where they induce cell cycle arrest.

| | $IC_{50}$ Value-U-937 cells | cell cycle arrest |
|---|---|---|
| $R_1 = H, R_2 = OCH_3, R_3 = H$ | 14.5 μM | G1 |
| $R_1 = OCH_3, R_2 = H, R_3 = H$ | 15.7 μM | G1 |
| $R_1 = H, R_2 = OCH_3, R_3 = OCH_3$ | 18.3 μM | G1 |
| | 8.0 μM | G2/M |
| | 3.1 μM | |
| | 7.1 uM | |

Figure 22:
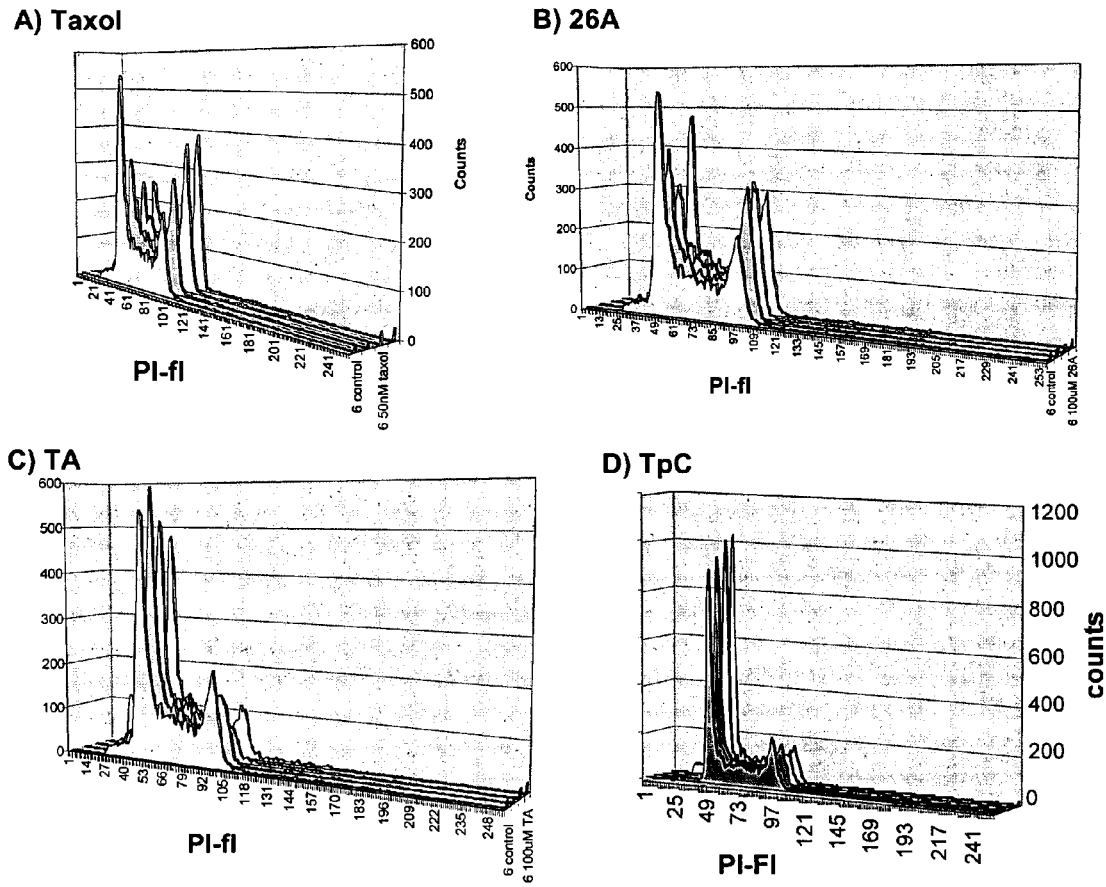
FIG. 22 illustrates an analysis of cell populations show that compounds containing the TPP and TPA building blocks give arrest in the G1-phase of the cell cycle (A and B), while compounds such as x cause arrest in the G2/M phase, similar to taxol. Compounds containing the triphenylacetic acid and triphenylpropionic acid building blocks all arrest growth in the G1 phase (C and D).

Cell cycle analysis and NCl screen. The data in FIG. 21 and Table 11 show potential structure-activity trends. Several amides derived from the triphenylacetic acid (TPA) and triphenylpropionic acid (TPP) building blocks induced a high degree of cell death in this assay. Experiments were conducted to determine the position on the cell cycle at which these compounds arrest cell growth. This is typically determined by assessing the DNA content as measured flow cytometry analysis of cells stained by propidium iodide. Flow cytometry data is presented in FIG. 22, along with control data. Compounds known to induce mitotic (M) phase arrest (such as Taxol) show a pronounced shift in the cell populations that shows 4n DNA (FIG. 22A). One of the active apoptotic inducers identified from this combinatorial library that was not derived from the TPA or TPP building blocks (x) also arrests cell growth in the G2/M phase as indicated by the data in FIG. 22B. However, compounds containing the triphenylacetic acid and triphenylpropionic acid building blocks all arrest cell growth in the G1 phase (FIG. 22C and FIG. 22D). Here compounds x and y correspond to compounds Z2 and Z3.

Given the interesting and somewhat unusual trait of G1 arrest, compounds x and y were tested for their ability to induce death in two melanoma cell lines: UACC-62 (human), and B16-F10 (mouse). These triphenylamides indeed showed excellent activity in the melanoma cell lines, with $IC_{50}$ values ranging from 400-1300 nM (Table 12). Compounds x and y were also submitted for testing in the NCl 60-cell line assay. The NCl data revealed that the compounds are quite active against a broad spectrum of cancers, and confirmed the $IC_{50}$ of 600 nM against the UACC-62 melanoma cell line. The triphenylamides (TPAs) induce apoptosis in these melanoma cell lines.

TABLE 2

| Structure | BF16-F10 | UACC-62 |
|---|---|---|
| (TA) triphenylacetamide N-phenethyl | 0.42 μM | 0.49 μM |
| (TpC) 3,3,3-triphenylpropanamide N-(3-methoxyphenethyl) | 0.85 μM | 1.34 μM |
| (34-CH) triphenylacetamide N-adamantyl | 15.65 uM | 2.4 uM |

Second generation library. Because multiple compounds containing the triphenylacetic- and triphenylpropionic amides were active against several melanoma cell lines and were shown to induce apoptosis by arresting the cell cycle in the G1 phase, a second library was made using only the triphenylacetic acid and triphenyl propionic acid building blocks. The acid chlorides derived from the two acids were treated in parallel with 61 different amines to provide 122 amide products; this reaction scheme and the various building blocks are shown in Scheme 2. Again, all of these final products were made on a 0.035 mmol scale and purified via filtration through a short plug of silica. Analysis of the compounds by HPLC and mass spectrometry once again showed that the compounds were highly pure. 110 of the compounds had a purity of >90%, and the average purity of the entire library was 92%.

All 122 amides thus produced are evaluated in the leukemia (HL-60) and lymphoma (U-937) cell lines, in addition to two different melanoma cell lines (UACC-62, CRL-1782) originally isolated from a human melanoma patients; a full description of each can be found via the website of the American Type Culture Collection or the National Cancer Institute. Compounds with activity in these assays are shown in Table 12.

Figure 3A:
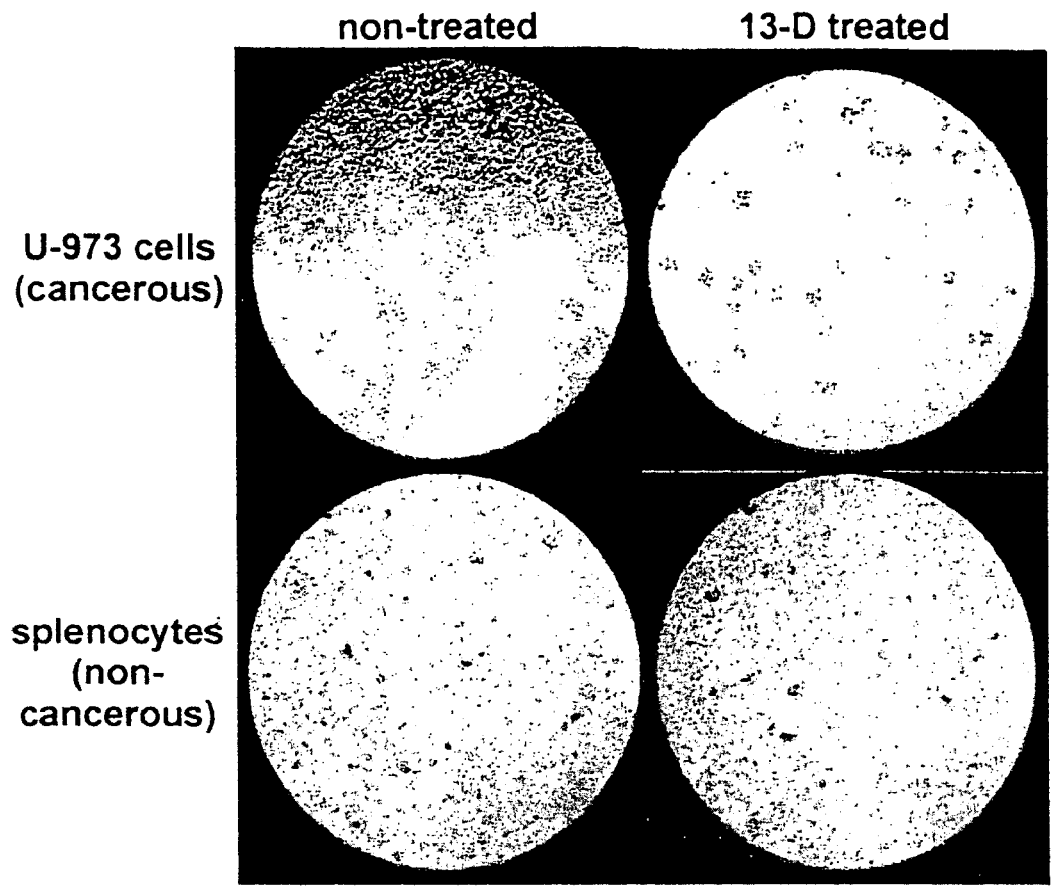
FIG. 3 illustrates the effects of treatment of cancerous and non-cancerous cells with compound 13D. Cancerous U-937 cells are almost completely killed by 13-D, whereas non-cancerous white blood cells show virtually no death. Cells were treated with 500 μM 13-D for 72 h. The IC50 of 13-D for U-937 cells is 44 μM, whereas it is greater than 1000 μM for the splenocytes.
Figure 3B:
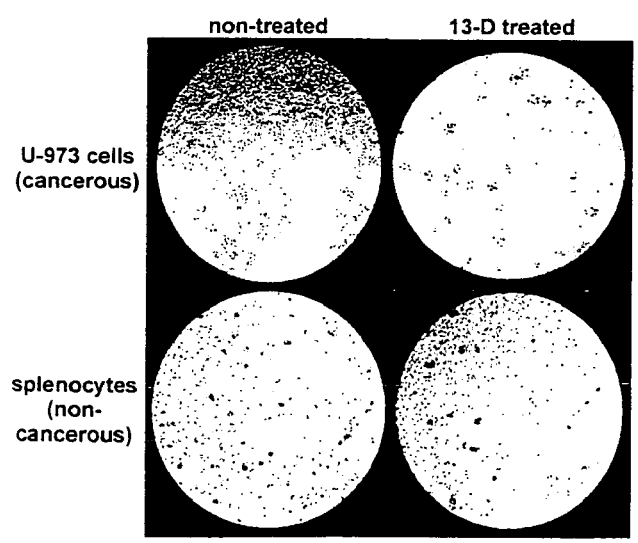

Apoptotic assays. To determine whether the observed death was due to apoptosis or necrosis, several apoptotic hallmarks were examined. Thus early stage (mitochondrial membrane depolarization), middle stage (caspase-3 like activation, PARP-1 cleavage) and late stage (chromatin condensation, phosphatidylserine exposure, membrane blebbing) biochemical events were monitored. The depolarization of mitochondrial membranes facilitates the release of pro-apoptotic proteins such as cytochrome c and AIF (apoptosis inducing factor) from the mitochondria into the cytosol. Several dyes, including JC-9, have been developed that provide a sensitive readout on this process. As shown in FIG. 3A, compound x shifts the fluorescence of this dye, consistent with mitochondrial membrane depolarization. The release of pro-apoptotic stimuli from the mitochondria initiates a cascade of events that ultimately results in the activation of the "executioner" caspases, typically caspase-3 and caspase-7. The caspase-3-like activity of the cells can be monitored with peptidic substrates. As shown in FIG. 3B, compound x induces strong caspase-3-like activity in U-937 cells after a 24 h treatment. PARP-1 cleavage. A final event in apoptosis is the exposure of phosphatidylserine on the outer leaflet of the cell membrane; this event allows for recognition of apoptotic cells by phagocytes, ultimately leading to the engulfment of the apoptotic cell and the recycling of the various cellular components. Phosphatidylserine exposure can be detected with fluorescently-labeled Annexin-V. As shown in FIG. 3C, compound x induces apoptosis as measured by Annexin-V staining and flow-cytometry.

Specificity for cancer cells. The vast majority of anti-cancer drugs are toxic to all rapidly dividing cell types, often leading to deleterious side effects and a reduced therapeutic window. For instance, hematopoietic bone marrow is responsible for the production of red and white blood cells, and the anemia observed upon treatment with certain chemotherapy agents is in a large part due to the toxicity of the anti-cancer drugs on cells in the human bone marrow. Thus, to determine the relative effect of the triphenylamides on melanoma versus normal cells, cells derived from the human bone marrow of a healthy donor were used; measurement of the effect on healthy bone marrow cells can assist in assessing the toxicity of putative anti-cancer agents. (17-20) These cells were treated with increasing concentrations of the compounds shown in Table 13, and cell viability was evaluated after 72 hours using the MTS bioreduction assay. The data in Table 13 indicate that several of the triphenyl amides have selective toxicity to melanoma cells versus the human bone marrow cells.

TABLE 13
Potent apoptotic inducers in melanoma cell lines.
| | U-937 | HL-60 | UACC-62 | B16F10 | Bone marrow |
|---|---|---|---|---|---|
| 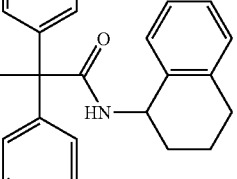 (34-AF) | 1.25 | 2.21 | 1.77 | 0.98 | 0.50 |
| 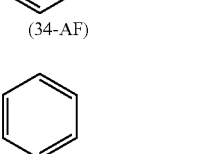 (34-BU) | 0.49 | 0.92 | 15.26 | 7.41 | 0.32 |
| 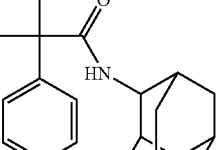 (34-CH) | 0.48 | 0.85 | 2.41 | 15.66 | 0.59 |
| 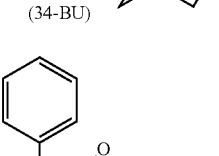 (35-BR) | 0.93 | 1.39 | 0.70 | 1.61 | 0.68 |
| 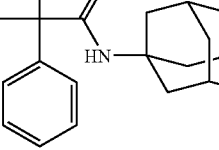 (34 AN) | 8.16 | 10.49 | 0.69 | 0.60 | 4.77 |

TABLE 13-continued

Potent apoptotic inducers in melanoma cell lines.

| | U-937 | HL-60 | UACC-62 | B16F10 | Bone marrow |
|---|---|---|---|---|---|
| 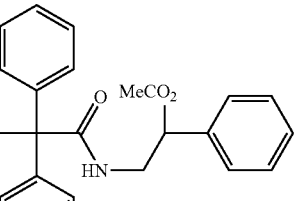 (34 BI) | 10.81 | 16.22 | 0.62 | 0.80 | 4.00 |
| 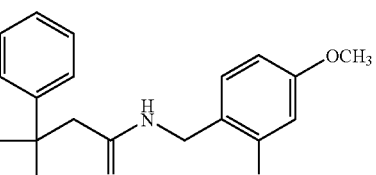 (35-AG) | 7.17 | 2.26 | 0.52 | 0.55 | 1.87 |
| 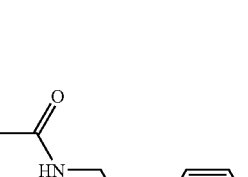 (TA minus one) | | | | | |
| Cyclophosphamide | | | | >100 | >100 |
| Prednisone | | | | >100 | >100 |
| Etoposide | | | | >100 | >100 |

There is currently no standard therapy for disseminated melanoma, and this cancer is resistant to both radiation treatment and chemotherapy. As a consequence, the five-year survival rates for patients with advanced melanoma approaches zero. It is becoming increasingly clear that melanoma may differ significantly at a molecular level from other forms of cancer. For instance, while a significantly high percentage of cancers have a mutation in the p53 gene, which encodes for the p53 transcription factor, less than 5% of melanomas have this mutation. (21) Melanoma cells may have defects elsewhere in the apoptotoic machinery. (7) Certain melanomas have a methylation-inactivated Apaf-1 signaling complex, (12) and/or upregulation of the caspase-inhibiting survivin protein. (13)

Late-stage malignant melanoma is essentially almost untreatable with existing chemotherapeutic agents. We have disclosed several triphenylamides that show significant in vitro potency against multiple melanoma cell lines through G1 phase cell cycle arrest and apoptosis. These cell lines have previously been shown to be resistant to common anti-cancer agents, and have defects in their apoptotic cascade. (12) Additionally, certain of the triphenylamides described herein have useful potencies in melanoma cell lines relative to their toxicity to bone-marrow cells derived from healthy human donors. Without wishing to be bound by a particular theory, this research may indicate that compounds that arrest cellular growth in the G1 phase of the cell cycle may be effective anti-melanoma agents. The present efforts can help address melanoma as a particularly devastating form of cancer in addition to other cancers.

REFERENCES FOR THIS EXAMPLE

1) Hanahan, D.; Weinberg, R. A. "The hallmarks of cancer" *Cell* 2000, 100, 57-70.
2) Adjei, A. A.; Rowinsky, E. K. "Novel anticancer agents in clinical development" *Cancer Biol. Ther.* 2003, S1, S5-S15.
3) McGovern, V. J.; Balch, C. M.; Wilton, G. W. E.; Lippincott, J. B., Ed.; Cutaneous melnoma: clinical management and treatment results worldwide: Philadelphia, 1985, pp 29-42.
4) Jemal, A.; Thomas, A.; Murray, T.; Thun, M. CA Cancer *J. Clin.* 2002, 52, 23-47.

5) Helmbach, H.; Rossmann, E.; Kern, M. A.; Schadendorf, D. "Drug-resistance in human melanoma" *Int. J. Cancer* 2001, 93, 617-622.
6) Serrone, L.; Zeuli, M.; Sega, F. M.; Cognetti, F. "Dacarbazine-based chemotherapy for metastatic melanoma: thirty-year experience overview." *J. Exp. Clin. Cancer Res.* 2000, 19, 21-34.
7) Soengas, M. S.; Lowe, S. W. "Apoptosis and melanoma chemoresistance" *Oncogene* 2003, 22, 3138-3151.
8) Middleton, M. R.; Lorigan, P.; Owen, J.; Ashcroft, L.; Lee, S. M.; Harper, P.; al, e. "A randomized phase III study comparing dacarbazine, BCNU, cisplatin and tamoxifen with dacarbazine and inerferon in advanced melanoma" *Br. J. Cancer* 2000, 82, 1158-1162.
9) Schadendorf, D.; Worm, M.; Algermissen, B.; Kohlmus, C. M.; Czarnetzki, B. M. "Chemosensitivity testing of human malignant melanoma. A retrospective analysis of clinical response and in vitro drug sensitivity" *Cancer* 1994, 73, 103-108.
10) Anderson, C.; Buzaid, A.; Legha, S. "Systemic treatment for advanced cutaneous melanoma" *Oncology* 1995, 9, 1149-1154.
11) Lev, D. C.; Onn, A.; Melinkova, V. O.; Miller, C.; Stone, V.; Ruiz, M. "Exposure of melanoma cells to dacarbazine results in enhanced tumor growth and metastasis in vivo" *J. Clin. Oncol.* 2004, 22, 2092-2100.
12) Soengas, M. S.; Capodieci, P.; Polsky, D.; Mora, J.; Esteller, M.; Opitz-Araya, X.; McCombie, R.; Herman, J. G.; Gerald, W. L.; Lazebnik, Y. A.; Cordon-Cardo, C.; Lowe, S. W. "Inactivation of the apoptosis effector Apaf-1 in malignant melanoma" *Nature* 2001, 409, 207-211.
13) Grossman, D.; McNiff, J. M.; Li, F.; Altieri, D. C. "Expression and targeting of the apoptosis inhibitor, survivin, in human melanoma" *J. Invest Dermatol.* 1999, 113, 1076-1081.
14) Cannon-Albright, L. A.; Goldgar, D. E.; Meyer, L. J.; Lewis, C. M.; Anderson, D. E.; Fountain, J. W.; Hegi, M. E.; Wiseman, R. W.; Petty, E. M.; Bale, A. E. "Assignment of a locus for familial melanoma, MLM, to chromosome 9p13-p22" *Science* 1992, 258, 1148-1152.
15) Fountain, J. W.; Karayiorgou, M.; Ernstoff, M. S.; Kirkwood, J. M.; Vlock, D. R.; Titus-Ernstoff, L.; Bouchard, B.; Vijayasaradhi, S.; Houghton, A. N.; Lahti, J. "Homozygous deletions within human chromosome band 9p21 in melanoma" *Proc. Natl. Acad. Sci.* 1992, 89, 10557-10561.
16) Nesterenko, V.; Putt, K. S.; Hergenrother, P. J. "Identification from a combinatorial library of a small molecule that selectively induces apoptosis in cancer cells" *J. Am. Chem. Soc.* 2003, 125(48): 14672-14673; December 3.
17) Konstantinov, S. M.; Topashka-Ancheva, M.; Benner, A.; Berger, M. R. "Alkylphosphocholines: Effects on human leukemic cell lines and normal bone marrow cells" *Int. J. Cancer* 1998, 77, 778-786.
18) de Graaff, M.; Maliepaard, M.; Pluim, D.; Floot, B. J.; Slaper-Cortenbach, I. C.; Schellens, J. H. "In vitro antagonistic cytotoxic interactions between platinum drugs and taxanes on bone marrow progenitor cell CFU-GM" *Anticancer Drugs* 1999, 10, 213-218.
19) LoRusso, P. M.; al., e. "Preclinical antitumor activity of XK469 (NSC 656889)" *Invest. New Drugs* 1999, 16, 287-296.
20) Oredipe, O. A.; Furbert-Harris, P. M.; Laniyan, I.; Griffin, W. M.; Sridhar, R. "Limits of stimulation of proliferation and differentiation of bone marrow cells of mice treated with swainsonine" *Internation. Immunopharm.* 2003, 3, 1537-1547.
21) Satyamoorthy, K.; Bogenrieder, T.; Herlyn, M. "No longer a molecular black box—new clues to apoptosis and drug resistance in melanoma" *Trends Mol. Med.* 2001, 7, 191-194.

STATEMENTS REGARDING INCORPORATION BY REFERENCE AND VARIATIONS

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. It is not intended, however, for any claim herein to specifically encompass any precise embodiment existing and legally qualifying as prior art for novelty; a claim purportedly encompassing such an embodiment is intended to be of scope so as to just exclude any such precise embodiment.

Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES

U.S. Provisional Application Ser. No. 60/516,566 by Hergenrother et al., filed Oct. 30, 2003; U.S. Provisional Patent Application Ser. No. 60/603,246 by Hergenrother et al., filed Aug. 20, 2004.

Nesterenko, V.; Byers, J. T.; Hergenrother, P. J. Org. Lett. 2003, 5, 281-284.

Monks A.; Scudiero D.; Johnson G.; Paull K.; Sausville E.; Mini-review. The NCl anti-cancer drug screen: a smart screen to identify effectors of novel targets; Anti-Cancer Drug Design October 1997, vol. 12, no. 7, pp. 533-541(9).

Alley, M. C., Scudiero, D. A., Monks, P. A., Hursey, M. L., Czerwinski, M. J., Fine, D. L., Abbott, B. J., Mayo, J. G., Shoemaker, R. H., and Boyd, M. R. Feasibility of Drug Screening with Panels of Human Tumor Cell Lines Using a Microculture Tetrazolium Assay. Cancer Research 48: 589-601, 1988.

Grever, M. R., Schepartz, S. A., and Chabner, B. A. The National Cancer Institute: Cancer Drug Discovery and Development Program. Seminars in Oncology, Vol. 19, No. 6, pp 622-638, 1992.

Boyd, M. R., and Paull, K. D. Some Practical Considerations and Applications of the National Cancer Institute In Vitro Anticancer Drug Discovery Screen. Drug Development Research 34: 91-109, 1995.

The invention is further described and set forth by the following claims:

1. A compound having formula:

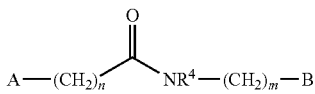

and salts thereof;
where:
n is 0 or I and m is 2;
$R^4$ of the —$NR^4$— group is hydrogen;
one of the $CH_2$ groups of the —$(CH_2)_n$— or —$(CH_2)_m$— groups that is not linked to —CO— or —$NR^4$— can be replaced with an oxygen atom;
one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— groups where each $R^4$ group therein is, independently, a hydrogen or an alkyl group;
A is an optionally substituted triphenyl methyl group; and
B is an optionally substituted phenyl ring, wherein the phenyl rings of A and B are optionally substituted with one or more halogens, one or more alkyl groups having 1 to 3 carbon atoms, one or more alkoxy groups having from 1 to 3 carbon atoms or combinations of such substituents.

2. The compound of claim 1 wherein n is 1.

3. The compound of claim 1 wherein A is an unsubstituted triphenyl methyl group.

4. The compound of claim 3 wherein B is a phenyl ring substituted with one or more alkoxy groups.

5. The compound of claim 1 having the structure of Compound Z2:

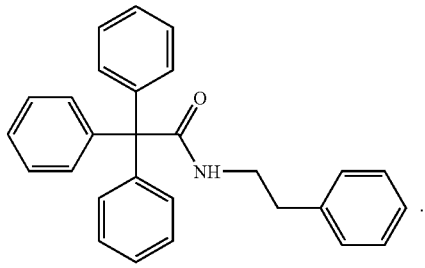

6. The compound of claim 1 having the structure of Compound Z3:

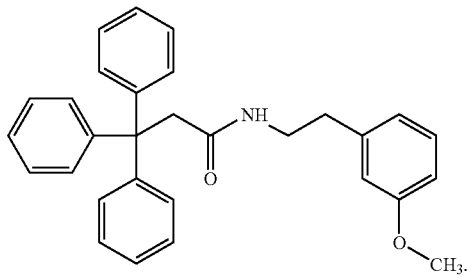

7. A pharmaceutical composition comprising an effective amount of a compound of claim 1 and a pharmaceutically acceptable carrier.

8. A compound having formula:

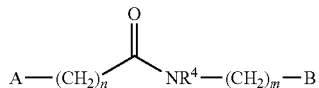

and salts thereof;
where:
n and m, independently, are integers ranging from 1 to 6;
$R^4$ of the —$NR^4$— group is a hydrogen or an alkyl group;
a —$CH_2$—$CH_2$— group of one or both of the —$(CH_2)_n$— or —$(CH_2)_m$— groups is replaced with a —$CR^4$=$CR^4$— group, where each $R^4$ group therein is, independently, a hydrogen or an alkyl group having 1-3 carbon atoms;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents;

D is an optionally substituted aromatic group having one or two carbon rings which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl and alkoxyl groups may be substituted with one or more halogens; and
wherein only one of A or B can be C.

9. A compound having formula:

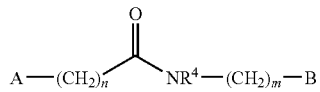

and salts thereof;
where:
n and m, independently, are integers ranging from 1 to 6;
$R^4$ of the —$NR^4$— group is a hydrogen or an alkyl group;
a —$CH_2$—$CH_2$— group of one or both of the —$(CH_2)_n$— or —$(CH_2)_m$— groups is replaced with a -$CR^4$=$CR^4$— group, where each $R^4$ group therein is, independently, a hydrogen or an alkyl group having 1-3 carbon atoms;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents;
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl and alkoxyl groups may be substituted with one or more halogens;
wherein only one of A or B can be C; and
wherein the $R^4$ group of the —$CR^4$=$CR^4$— group is hydrogen.

10. The compound of claim 9 wherein the $R^4$ group of the —$NR^4$— group is hydrogen.

11. The compound of claim 10 wherein m and n are 2.

12. The compound of claim 11 wherein —$(CH_2)_n$— is replaced with —CH=CH—.

13. The compound of claim 12 wherein A and B are D.

14. The compound of claim 11 wherein one or more of the carbons of the —$(CH_2)_m$— are substituted with one or two non-hydrogen substituents selected from halogens, alkyl groups having 1 to 3 carbon atoms, or alkoxy groups having from 1 to 3 carbon atoms.

15. The compound of claim 14 wherein —$(CH_2)_n$— is replaced with —CH=CH—.

16. The compound of claim 15 wherein A and B are D.

17. The compound of claim 12 wherein D is a substituted aromatic group having one carbon ring, wherein one or more carbons of the ring are substituted with one or more halogens, one or more alkyl groups having from 1 to 3 carbon atoms or one or more alkoxy groups having from 1 to 3 carbons, wherein the alkyl and alkoxy groups are optionally substituted with one or more halogens.

18. The compound of claim 17 wherein A is an aromatic group having one carbon ring optionally substituted with one or more halogens.

19. The compound of claim 17 wherein B is an aromatic group having one carbon ring substituted with one or more alkoxy groups having from 1 to 3 carbons, wherein the alkoxy groups are optionally substituted with one or more halogens.

20. The compound of claim 19 wherein A is an aromatic group having one carbon ring optionally substituted with one or more halogens.

21. The compound of claim 18 wherein one or more of the carbons of the —$(CH_2)_m$— group are substituted with one or two non-hydrogen substituents selected from halogens, alkyl groups having 1 to 3 carbon atoms, or alkoxy groups having from 1 to 3 carbon atoms.

22. The compound of claim 19 wherein one or more of the carbons of the —$(CH_2)_m$— group are substituted with one or two non-hydrogen substituents selected from halogens, alkyl groups having 1 to 3 carbon atoms, or alkoxy groups having from 1 to 3 carbon atoms.

23. A pharmaceutical composition comprising a pharmaceutically acceptable carrier and an effective amount of a compound having formula:

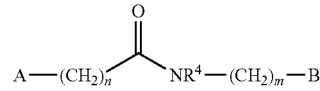

and salts thereof;
where:
n and m, independently, are zeroes or integers ranging from 1 to 6;
$R^4$ of the —$NR^4$— group is an alkyl group;
one of the $CH_2$ groups of the —$(CH_2)_n$— or —$(CH_2)_m$— groups that is not linked to —CO—, or —$NR^4$— can be replaced with an oxygen atom;
one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— group, where each $R^4$ group therein is, independently, a hydrogen or an alkyl group;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents;
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms or one or more alkoxy groups having from 1 to 3 carbons, wherein the alkyl and alkoxy groups may be substituted with one or more halogens; and wherein only one of A or B can be C.

24. A pharmaceutical composition comprising a pharmaceutically acceptable carrier and an effective amount of a compound having formula:

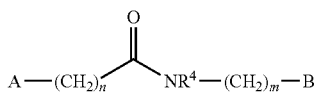

and salts thereof;
where:
n and m, independently, are zeroes or integers ranging from 1 to 6;
$R^4$ of the —$NR^4$— group is an alkyl group;
a —$CH_2$—$CH_2$— group of either or both of the —$(CH_2)_n$— or —$(CH_2)_m$— groups is optionally replaced with a —$CR^4$=$CR^4$— group, where each $R^4$ group therein is, independently, a hydrogen or an alkyl group;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms or combinations of such substituents;
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl or alkoxy groups may be substituted with one or more halogens; and
wherein only one of A or B can be C.

25. A pharmaceutical composition comprising an effective amount of a compound of claim 8 and a pharmaceutically acceptable carrier.

26. A pharmaceutical composition comprising a pharmaceutically acceptable carrier and an effective amount of a compound having formula:

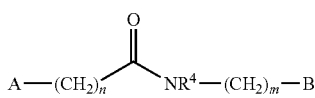

and salts thereof;
where:
m and n are 2;
$R^4$ is a hydrogen or an alkyl group;
one of the $CH_2$ groups of the —$(CH_2)_n$— or —$(CH_2)_m$— groups that is not linked to —CO, or can be replaced with an oxygen atom;

one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— group, where each $R^4$ group therein is independently, a hydrogen or an alkyl group;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms or combinations of such substituents;
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl and alkoxy groups may be substituted with one or more halogens; and
wherein only one of A or B can be C.

27. A compound having formula:

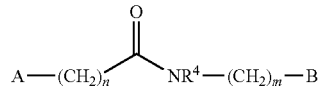

and salts thereof;
where:
n and m, independently, are zeroes or integers ranging from 1 to 6;
$R^4$ of the —$NR^4$— group is an alkyl group;
one of the $CH_2$ groups of the —$(CH_2)_n$— or —$(CH_2)_m$— groups that is not linked to —CO, or —$NR^4$— can be replaced with an oxygen atom;
one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— group, where each $R^4$ group therein is, independently, a hydrogen or an alkyl group;
A and B, independently, are selected from C or D where:
C is a straight-chain alkyl group substituted with one or more optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents; or
C is an alkyl group substituted with one, two or three optionally substituted phenyl rings, wherein the phenyl rings are optionally substituted with one or more halogens, one or more alkyl groups having 1 to 3 carbon atoms, one or more alkoxy groups having from 1 to 3 carbon atoms, or combinations of such substituents;

D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl and alkoxy groups may be substituted with one or more halogens;

wherein only one of A or B can be C; and wherein the $R^4$ group of —$NR^4$— or the $R^4$ group of —$CR^4$=$CR^4$— is an alkyl group having 1-3 carbon atoms.

28. The compound of claim 1 wherein n is 0.

29. A compound having formula:

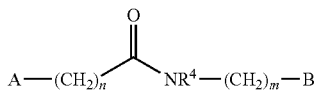

and salts thereof;
where:
n and m, independently, are zeroes or integers ranging from 1 to 6;
$R^4$ of the —$NR^4$— group is an alkyl group;
one of the $CH_2$ groups of the —$(CH_2)_n$— or —$(CH_2)_m$— groups that is not linked to —CO, or —$NR^4$— can be replaced with an oxygen atom;
one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— group, where each $R^4$ group therein is, independently, a hydrogen or an alkyl group;
A and B, independently, are selected from C or D where:
C is a triphenyl methyl group; and
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms or one or more alkoxy groups having from 1 to 3 carbons, wherein the alkyl and alkoxy groups may be substituted with one or more halogens; and
wherein only one of A or B can be C.

30. A compound having formula:

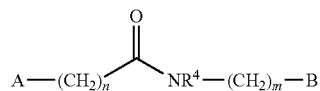

and salts thereof;
where:
n and m, independently, are zeroes or integers ranging from 1 to 6;
$R^4$ of the —$NR^4$— group is an alkyl group;
one of the $CH_2$ groups of the —$(CH_2)_n$— or —$(CH_2)_m$— groups that is not linked to —CO, or —$NR^4$— can be replaced with an oxygen atom;
one or more of the carbons of the —$(CH_2)_n$— or —$(CH_2)_m$— groups can be substituted with one or two non-hydrogen substituents selected from halogens, alkyl groups having 1 to 3 carbon atoms, or alkoxy groups having from 1 to 3 carbon atoms;
a —$CH_2$—$CH_2$— group of either or both of the —$(CH_2)_n$— or —$(CH_2)_m$— groups can be replaced with a —$CR^4$=$CR^4$— group, where each $R^4$ group therein is, independently, a hydrogen or an alkyl group;
A is a triphenyl methyl group and B is D, where
D is an optionally substituted aromatic group having one or two carbon rings, which may be fused aromatic rings, wherein one or more carbons of the one or two aromatic rings are optionally substituted with one or more halogens, one or more alkyl groups having from 1 to 3 carbon atoms, or one or more alkoxy groups having from 1 to 3 carbons, wherein the alkyl and alkoxy groups may be substituted with one or more halogens.

31. A pharmaceutical composition comprising an effective amount of a compound of claim 30 and a pharmaceutically acceptable carrier.

32. A pharmaceutical composition comprising an effective amount of a compound of claim 30 and a pharmaceutically acceptable carrier.

33. A pharmaceutical composition comprising an effective amount of a compound of claim 9 and a pharmaceutically acceptable carrier.

34. A pharmaceutical composition comprising an effective amount of a compound of claim 27 and a pharmaceutically acceptable carrier.

* * * * *

UNITED STATES PATENT AND TRADEMARK OFFICE
CERTIFICATE OF CORRECTION

PATENT NO. : 7,632,972 B2  Page 1 of 1
APPLICATION NO. : 10/976186
DATED : December 15, 2009
INVENTOR(S) : Hergenrother et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Twenty-first Day of December, 2010

David J. Kappos
*Director of the United States Patent and Trademark Office*